United States Patent
Morrison et al.

(10) Patent No.: US 9,139,634 B2
(45) Date of Patent: Sep. 22, 2015

(54) INTERFERON-ANTIBODY FUSION PROTEINS DEMONSTRATING POTENT APOPTOTIC AND ANTI-TUMOR ACTIVITIES

(75) Inventors: Sherie L. Morrison, Los Angeles, CA (US); Tzu-Hsuan Huang, Houston, TX (US); Caiyun Xuan, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 215 days.

(21) Appl. No.: 12/678,981

(22) PCT Filed: Sep. 19, 2008

(86) PCT No.: PCT/US2008/077074
§ 371 (c)(1),
(2), (4) Date: Aug. 11, 2010

(87) PCT Pub. No.: WO2009/039409
PCT Pub. Date: Mar. 26, 2009

(65) Prior Publication Data
US 2010/0297076 A1    Nov. 25, 2010

Related U.S. Application Data

(60) Provisional application No. 60/994,717, filed on Sep. 21, 2007.

(51) Int. Cl.
| | | |
|---|---|---|
| A61K 38/21 | (2006.01) |
| A61K 39/395 | (2006.01) |
| C07K 14/56 | (2006.01) |
| C07K 14/565 | (2006.01) |
| C07K 16/32 | (2006.01) |
| C07K 16/30 | (2006.01) |
| C07K 16/46 | (2006.01) |
| A61K 47/48 | (2006.01) |
| C07K 14/555 | (2006.01) |
| C07K 16/28 | (2006.01) |
| A61K 39/00 | (2006.01) |

(52) U.S. Cl.
CPC .............. *C07K 14/56* (2013.01); *A61K 38/212* (2013.01); *A61K 38/215* (2013.01); *A61K 47/48423* (2013.01); *A61K 47/48569* (2013.01); *A61K 47/48584* (2013.01); *A61K 47/48661* (2013.01); *C07K 14/555* (2013.01); *C07K 14/565* (2013.01); *C07K 16/2863* (2013.01); *C07K 16/2887* (2013.01); *C07K 16/32* (2013.01); *A61K 2039/505* (2013.01); *C07K 2317/622* (2013.01); *C07K 2319/33* (2013.01)

(58) Field of Classification Search
CPC . A61K 38/212; A61K 38/215; C07K 14/555; C07K 14/56; C07K 14/565; C07K 2319/00; C07K 16/32; C07K 16/2887
See application file for complete search history.

(56) References Cited

U.S. PATENT DOCUMENTS

| | | | |
|---|---|---|---|
| 5,696,237 A | 12/1997 | Fitzgerald et al. | |
| 5,824,782 A | 10/1998 | Holzer et al. | |
| 5,980,895 A * | 11/1999 | Pastan et al. ............... | 424/178.1 |
| 6,428,788 B1 | 8/2002 | Debinski et al. | |
| 6,800,735 B2 | 10/2004 | Whitty et al. | |
| 6,893,625 B1 | 5/2005 | Robinson et al. | |
| 7,005,498 B1 | 2/2006 | Steinaa et al. | |
| 7,151,164 B2 | 12/2006 | Hansen et al. | |
| 8,258,263 B2 | 9/2012 | Morrison et al. | |
| 8,563,692 B2 | 10/2013 | Morrison et al. | |
| 2002/0193569 A1 | 12/2002 | Hanna | |
| 2003/0219433 A1* | 11/2003 | Hansen et al. ............. | 424/141.1 |
| 2004/0005647 A1 | 1/2004 | Denardo et al. | |
| 2005/0008649 A1* | 1/2005 | Shin et al. .................. | 424/178.1 |
| 2005/0079154 A1 | 4/2005 | Yarkoni et al. | |
| 2005/0232931 A1 | 10/2005 | Ma et al. | |
| 2006/0228300 A1* | 10/2006 | Chang et al. ................. | 424/1.49 |
| 2006/0263368 A1 | 11/2006 | Rosenblum et al. | |
| 2006/0287509 A1 | 12/2006 | Marks et al. | |
| 2010/0172868 A1 | 7/2010 | Morrison et al. | |
| 2010/0297076 A1 | 11/2010 | Morrison et al. | |
| 2011/0104112 A1 | 5/2011 | Morrison et al. | |
| 2011/0165122 A1 | 7/2011 | Shahangian et al. | |
| 2014/0079668 A1 | 3/2014 | Morrison et al. | |

FOREIGN PATENT DOCUMENTS

| | | |
|---|---|---|
| JP | 2003-535908 | 2/2003 |
| JP | 2004-528014 | 9/2004 |
| JP | 2005-520853 | 7/2005 |
| JP | 2006-500904 | 1/2006 |

(Continued)

OTHER PUBLICATIONS

Goldstein, D., et al. The role of interferon in cancer therapy: A current perspective. CA Cancer J. Clin., 1988, vol. 38, p. 258-277.*
Zaidi, M.R., et al. The two faces of interferon-gamma in cancer. Clin. Cancer Res., 2011, vol. 17, No. 19, p. 1-7.*
US Office Action dated Feb. 1, 2011 issued in U.S. Appl. No. 12/650,329.
Mizokami et al. (2003) "Chimeric TNT-3 Antibody/Murine Interferon-γ Fusion Protein for the Immunotherapy of Solid Malignancies" *Hybridoma and Hybridomics* 22(4):197-207.
Portlock et al. (2006) "Pegylated interferon plus rituximab in advanced stage, indolent lymphoma: is there CD20 antigen uprcgulation?" *Leukemia & Lymphoma* 47(7):1260-1264.
Scharma et al. (2006) "Antibody targeted drugs as cancer therapeutics.", *Nature Reviews Drug Discovery* 5: 147-159.
PCT International Search Report and Written Opinion dated Jan. 12, 2009 issued in PCT/US08/77074 (WO2009/039409).

(Continued)

*Primary Examiner* — Robert Landsman
*Assistant Examiner* — Bruce D Hissong
(74) *Attorney, Agent, or Firm* — Tom Hunter; Weaver Austin Villeneuve & Sampson LLP

(57) ABSTRACT

This invention provides novel chimeric moieties that show significant efficacy against cancers. In certain embodiments the chimeric moieties comprise a targeting moiety attached to an interferon. In certain embodiments, the chimeric moieties comprise fusion proteins where an antibody that specifically binds to a cancer marker is fused to interferon alpha (IFN-α).

16 Claims, 41 Drawing Sheets

(56) References Cited

FOREIGN PATENT DOCUMENTS

| JP | 2008-505174 | 2/2008 |
|---|---|---|
| JP | 2009-511495 | 3/2009 |
| WO | WO 01/97844 | 12/2001 |
| WO | WO 03/080106 | 10/2003 |
| WO | WO 2006/019447 | 2/2006 |
| WO | WO 2007/027106 | 3/2007 |
| WO | WO 2007/044616 | 4/2007 |
| WO | WO 2009/039409 | 3/2009 |

OTHER PUBLICATIONS

PCT International Preliminary Report on Patentability dated Mar. 24, 2010 issued in PCT/US08/77074 (WO2009/039409).
Bird el al. (1988) "Single-Chain Antigen-Binding Proteins", *Science*, 242:423-426.
Flannery el al. (1984) "Immunomodulation: NK cells activated by interferon-conjugated monoclonal antibody against human osteosarcoma.", *Eur J Cancer Clin Oncol.*, 20(6):791-8.
Huston et al. (1988) "Protein engineering of antibody binding sites: Recovery of specific activity in an anti-digoxin single-chain Fv analogue produced in *Escherichia coli*.", *Proc. Natl. Acad. Sci.*, 85:5879-5883.
Marshall et al. (2001) "Engineering and Characterization of a Novel Fusion Protein Incorporating B7.2 and an Anti-ErbB-2 Single-Chain Antibody Fragment for the Activation of Jurkat T Cells", *J. Immunotherapy*, 24(1): 27-36.
Ozzello et al. (1998) "Conjugation of interferon alpha to a humanized monoclonal antibody (HuBrE-3v1) enhances the selective localization and antitumor effects of interferon in breast cancer xenografts.", *Breast Cancer Res Treat.*, 48(2):135-47.
Rossi et al. (2009) "CD20-targeted tetrameric interferon-, a novel and potent immunocytokine for the therapy of B-cell lymphomas" *Blood*, 114:3864-3871.
Xuan et al. (2010) "Targeted delivery of interferon-alpha via fusion to anti-CD20 results in potent antitumor activity against B-cell lymphoma." *Blood*, 115(14):2864-71.
US Office Action dated Aug. 8, 2011 issued in U.S. Appl. No. 12/650,329.
Alfthan et al. (1995) "Properties of a single-chain antibody containing different linker peptides" *Protein Engineering* 8(7):725-731.
Cheng et al. (2008) "Antibody-fused interferons as an effective approach to enhance target specificity and antiviral efficacy of type I interferons" *Cell Research* 18: 1230-32.
Curtis et al. (1991) "Enhanced hematopoietic activity of a human granulocyte/macrophage colony-stimulating factor-interleukin 3 fusion protein", *Proc. Natl. Acad. Sci. USA* 88: 5809-5813.
Dela Cruz et al. (2004) "Antibody-cytokine fusion proteins: innovative weapons in the war against cancer" *Clin Exp Med* 4: 57-64.
Ebbinghaus et al. (2004) "An Antibody-Interferon Gamma Fusion Protein for Cancer Therapy" *A dissertation submitted to the Swiss Federal Institute of Technology Zurich for the degree of Doctor of Natural Sciences* pp. 1-137.
Ebbinghaus et al. (2005) "Engineered vascular-targeting antibody-interferon-γ fusion protein for cancer therapy" *Int. J. Cancer* 116: 304-313.
Frey et al. (2011) "Antibody-Based Targeting of Tumor Vasculature and Stoma" *The Tumor Microenvironment* 4 Part VI Chapter 22: 419-450.
Frey et al. (2011) "Antibody-based targeting of interferon-alpha to the tumor neovasculature: a critical evaluation" *Integr. Biol.* 3: 468-478.
Heuser et al. (2003) "ANTI-CD30-IL-12 Antibody-Cytokine Fusion Protein That Induces IFN-Γ Secretion of T Cells And NK Cell-Mediated Lysis Of Hodgkin's Lymphoma-Derived Tumor Cells" *Int. J. Cancer* 106: 545-552.
Kaspar et al. (2007) "The Antibody-Mediated Targeted Delivery of Interleukin-15 and GM-CSF to the Tumor Neovasculature Inhibits Tumor Growth and Metastasis" *Cancer Res* 67(10): 4940-4948.
Klimka et al. (2003) "Construction of proteolysis resistant human interleukin-2 by fusion to its protective single chain antibody" *Cytokine* 22: 134-141.
McCarron et al. (2005) "Antibody Conjufates and Therapeutic Strategies" *Molecular Interventions* 5(6): 368-380.
Chinese Office Action dated May 2, 2012 issued in CN200880117225.8.
EP Extended Search Report and Written Opinion dated Apr. 26, 2012 issued in EP08831632.8.
Israeli Office Action dated Apr. 5, 2012 issued in IL-204644.
US Final Office Action dated Apr. 30, 2012 issued in U.S. Appl. No. 12/650,329.
US Notice of Allowance dated Jun. 18, 2012 issued in U.S. Appl. No. 12/650,329.
US Office Action dated Jul. 6, 2012 issued in U.S. Appl. No. 12/985,122.
Berger et al. (2002) "Licensure of Gemtuzumab Ozogamicin for the Treatment of Selected Patients 60 Years of Age or Older with Acute Myeloid Leukemia in First Relapse" *Invest. New Drugs* 20(4):395-406.
Bosly et al. (2004) "Role of anti-CD20 monoclonal antibody in association with immunomodulatory agents", *Pathologie Biologie* 52: 39-42 [English Abstract].
Helguera et al. (2006) "Cytokines fused to antibodies and their combinations as therapeutic agents against different peritoneal HER2/neu expressing tumors", *Molecular Cancer Therapeutics, American Association Of Cancer Research* 5(4): 1029-1040.
Huang et al. (2006) "Fusion of anti- HER2/ neu with inflammatory cytokines IFN- alpha and TNF- alpha results in molecules that elicit an anti- tumor response or potentiate wound healing" *Dissertation* pp. 1-120 XP009158273.
Huang et al. (2007) "Targeting IFN-alpha to B cell lymphoma by a tumor-specific antibody elicits potent antitumor activities." *Journal of Immunology* 179(10): 6881-6888.
Jain et al. (2007) "Engineering antibodies for clinical applications", *Trends in Biotechnology* 25(7): 307-316.
Peng et al. (1999) "A Single-Chain IL-12 IgG3 Antibody Fusion Protein Retains Antibody Specificity and IL-12 Bioactivity and Demonstrates Antitumor Activity" *J. Immunol.* 163: 250-258.
Rossi et al. (2010) "A Bispecific Antibody-IFNα2b Immunocytokine Targeting CD20 and HLA-DR Is Highly Toxic to Human Lymphoma and Multiple Myeloma Cells" *Cancer Res.* 70: 7600-7609.
Song et al. (2007) "Construction of Expression Vector of Anti-HBsAg dsFv and Alpha-IFN Fusion Gene", *Chinese Journal of Public Health* 23(9): 1096-1099 [English Abstract].
Australian Office Action dated Feb. 26, 2013 issued in 2008302111.
Chinese Office Action dated Feb. 4, 2013 issued in CN200880117225.8 [with English Translation].
Chinese Office Action dated Jul. 15, 2013 issued in CN200880117225.8.
EP Office Action dated Feb. 8, 2013 issued in EP08831632.8.
Israeli Office Action dated Apr. 17, 2013 issued in IL-204644 [with English Translation].
Japanese Office Action dated Jan. 29, 2013 issued in JP 2010-526011 [with English Translation].
Mexican Office Action dated May 7, 2013 issued in MX/A/2010/003099.
US Final Office Action dated Apr. 2, 2013 issued in U.S. Appl. No. 12/985,122.
US Notice of Allowance dated Aug. 9, 2013 issued in U.S. Appl. No. 12/985,122.
Wei et al. (1998) "Clone and expression of a fusion protein consisting of anti-HBsAg Fab fragment and interferon—α in *E.coli*" *Chinese Journal of Hepatology* 6(4): 229-231. [Abstract Only].
Chinese Final Rejection dated Jan. 6, 2014 issued in CN200880117225.8.
Japanese Final Office Action dated Mar. 10, 2014 issued in JP 2010-526011.
Mexican Office Action dated Feb. 12, 2014 issued in MX/A/2010/003099.

\* cited by examiner

Anti-HER2/neu IgG3 heavy chain-IFNα

MGWSWVMHLSPVSNCGVHSQVQLVQSGAEVKKPGE
SLKISCKGSGYSFTSYWIAWVRQMPGKGLEYMGLIY
PGDSDTKYSPSFQGQVTISVDKSVSTAYLQWSSLKP
SDSAVYFCARHDVGYCTDRTCAKWPEYFQHWGQGT
LVTVSSASTKGPSVFPLAPCSRSTSGGTAALGCLVK
DYFPEPVTVSWNSGALTSGVHTFPAVLQSSGLYSLS
SVVTVPSSSLGTQTYTCNVNHKPSNTKVDKRVELKT
PLGDTTHTCPRCPEPKSCDTPPPCPRCPEPKSCDTP
PPCPRCPEPKSCDTPPPCPRCPAPELLGGPSVFLFP
PKPKDTLMISRTPEVTCVVVDVSHEDPEVQFKWYVD
GVEVHNAKTKLREEQYNSTFRVVSVLTVLHQDWLNG
KEYKCKVSNKALPAPIEKTISKAKGQPREPQVYTLP
PSREEMTKNQVSLTCLVKGFYPSDIAVEWESNGQPE
NNYNTTPPMLDSDGSFFLYSKLTVDKSRWQQGNIFS
CSVMHEALHNHYTQKSLSLPGK<u>SGGGGSGGGGSG
GGGS</u>CDLPQTHNLRNKRALTLLVQMRRLSPLSCLKD
RKDFGFPQEKVDAQQIKKAQAIPVLSELTQQILNIFT
SKDSSAAWNATLLDSFCNDLHQQLNDLQGCLMQQV
GVQEFPLTQEDALLAVRKYFHRITVYLREKKHSPCA
WEVVRAEVWRALSSSANVLGRLREEK

Anti-HER2/neu IgG3-IFNα light chain sequence

MEWSCVMLFLLSVTAGVHSDIQMTQSPSSLSASVGD
RVTITCRASQDVNTAVAWYQQKPGKAPKLLIYSASF
LYSGVPSRFSGSRSGTDFTLTISSLQPEDFATYYCQ
QHYTTPPTFGQGTKVEIKRTVAAPSVFIFPPSDEQLK
SGTASVVCLLNNFYPREAKVQWKVDNALQSGNSQE
SVTEQDSKDSTYSLSSTLTLSKADYEKHKVYACEVT
HQGLSSPVTKSFNRGEC

*Fig. 1A*

αCD20 light chain - nucleic acid sequence

ATGAAGTTGCCTGTTAGGCTGTTGGTGCTGATGTTCTGGATTCCTGCTTCCAGCAGTCAAA
TTGTTCTCTCCCAGTCTCCAGCAATCCTGTCTGCATCTCCAGGGGAGAAGGTCACAATGAC
TTGCAGGGCCAGCTCAAGTGTAAGTTACATCCACTGGTTCCAGCAGAAGCCAGGATCCTCC
CCCAAACCCTGGATTTATGCCACATCCAACCTGGCTTCTGGAGTCCCTGTTCGCTTCAGTG
GCAGTGGGTCTGGGACTTCTTACTCTCTCACAATCAGCAGAGTGGAGGCTGAAGATGCTGC
CACTTATTACTGCCAGCAGTGGACTAGTAACCCACCCACGTTCGGAGGGGGGACCAAGCTG
GAAATCAAACGTAAGTCGACTTTCTCATCTTTTTTATGTGTAAGACACAGGTTTTCATGT
TAGGAGTTAAAGTCAGTTCAGAAAATCTTGAGAAAATGGAGAGGGCTCATTATCAGTTGAC
GTGGCATACAGTGTCAGATTTTCTGTTTATCAAGCTAGTGAGATTAGGGGCAAAAGAGGC
TTTAGTTGA

αCD20 light chain - amino acid sequence

MKLPVRLLVLMFWIPASSSQIVLSQSPAILSASPGEKVTMTCRASSSVSYIHWFQQKPGSS
PKPWIYATSNLASGVPVRFSGSGSGTSYSLTISRVEAEDAATYYCQQWTSNPPTFGGGTKL
EIKRKSTFSSFFMCKTQVFMLGVKVSSENLEKMERAHYQLTWHTVSDFLFIKLVRLGAKRG
FS

*Fig. 1B*

αCD20-IgG3-muIFNα Gly₄Ser linker - nucleic acid sequence

ATGTACTTGGGACTGAACTGTGTAATCATAGTTTTTCTCTTAAAAGGTGTCCAGAGTCAGG
TACAACTGCAGCAGCCTGGGGCTGAGCTGGTGAAGCCTGGGGCCTCAGTGAAGATGTCCTG
CAAGGCTTCTGGCTACACATTTACCAGTTACAATATGCACTGGGTAAAACAGACACCTGGT
CGGGGCCTGGAATGGATTGGAGCTATTTATCCCGGAAATGGTGATACTTCCTACAATCAGA
AGTTCAAAGGCAAGGCCACATTGACTGCAGACAAATCCTCCAGCACAGCCTACATGCAGCT
CAGCAGCCTGACATCTGAGGACTCTGCGGTCTATTACTGTGCAAGATCGACTTACTACGGC
GGTGACTGGTACTTCAATGTCTGGGGCGCAGGGACCACGGTCACCGTCTCTGCAGCTAGCA
CCAAGGGCCCATCGGTCTTCCCCCTGGCGCCCTGCTCCAGGAGCACCTCTGGGGGCACAGC
GGCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACACCTGCAA
CGTGAATCACAAGCCCAGCAACACCAAGGTGGACAAGAGAGTTGGTGAGAGGCCAGCGCAG
GGAGGGAGGGTGTCTGCTGGAAGCCAGGCTCAGCCCTCCTGCCTGGACGCATCCGGCTGT
GCAGTCCCAGCCCAGGGCACCAAGGCAGGCCCCGTCTGACTCCTCACCCGGAGGCCTCTGC
CCGCCCCACTCATGCTCAGGGAGAGGGTCTTCTGGCTTTTTCCACCAGGCTCCGGGCAGGC
ACAGGCTGGATGCCCCTACCCCAGGCCCTTCACACACAGGGGCAGGTGCTGCGCTCAGAGC
TGCCAAGAGCCATATCCAGGAGGACCCTGCCCCTGACCGAGCTCAAAACCCCACTTGGTGA
CACAACTCACACATGCCCACGGTGCCCAGAGCCCAAATCTTGTGACACACCTCCCCCGTGC
CCAAGGTGCCCAGAGCCCAAATCTTGTGACACACCTCCCCGTGCCCAAGGTGCCCAGAGC
CCAAATCTTGTGACACACCTCCCCGTGCCCAAGGTGCCCATGATTTCCCGGACCCCTGAG
GTCACGTGCGTGGTGGTGGACGTGAGCCACGAAGACCCCGAGGTCCAGTTCAAGTGGTACG
TGGACGGCGTGGAGGTGCATAATGCCAAGACAAAGCTGCGGGAGGAGCAGTACAACAGCAC
GTTCCGTGTGGTCAGCGTCCTCACCGTCCTGCACCAGGACTGGCTGAACGGCAAGGAGTAC
AAGTGCAAGGTCTCCAACAAAGCCCTCCCAGCCCCCATCGAGAAACCATCTCCAAAGCCAA
AATGACCAAGAACCAGGTCAGCCTGACCTGCCTGGTCAAAGGCTTCTACCCCAGCGACATC
GCCGTGGAGTGGGAGAGCAATGGGCAGCCGGAGAACAACTACAACACCACGCCTCCCATGC
TGGACTCCGACGGCTCCTTCTTCCTCTACAGCAAGCTCACCGTGGACAAGAGCAGGTGGCA
GCAGGGGAACATCTTCTCATGCTCCGTGATGCATGAGGCTCTGCACAACCACTACACGCAG
AAGAGCCTCTCCCTGTCTCCGGGTAAATCTGGTGGCGGTGGATCCTGTGACCTGCCTCAGA
CTCATAACCTCAGGAACAAGAGAGCCTTGACACTCCTGGTACAAATGAGGAGACTCTCCCC
TCTCTCCTGCCTGAAGGACAGGAAGGACTTTGGATTCCCGCAGGAGAAGGTGGATGCCCAG
CAGATCAAGAAGGCTCAAGCCATCCCTGTCCTGAGTGAGCTGACCCAGCAGATCCTGAACA
TCTTCACATCAAAGGACTCATCTGCTGCTTGGAATGCAACCCTCCTAGACTCATTCTGCAA
TGACCTCCACCAGCAGCTCAATGACCTGCAAGGTTGTCTGATGCAGCAGGTGGGGGTGCAG
GAATTTCCCCTGACCCAGGAAGATGCCCTGCTGGCTGTGAGGAAATACTTCCACAGGATCA
CTGTGTACCTGAGAGAGAAGAAACACAGCCCTGTGCCTGGGAGGTGGTCAGAGCAGAAGT
CTGGAGAGCCCTGTCTTCCTCTGCCAATGTGCTGGGAAGACTGAGAGAAGAGAAATGA

*Fig. 1C*

αCD20-IgG3-muIFNα Gly₄Ser linker - Amino acid sequence

MYLGLNCVIIVFLLKGVQSQVQLQQPGAELVKPGASVKMSCKASGYTFTSYNMHWVKQTPG
RGLEWIGAIYPGNGDTSYNQFKGKATLTADKSSSTAYMQLSSLTSEDSAVYYCARSTYYG
GDWYFNVWGAGTTVTVSAASTKGPSVFPLAPCSRSTSGGTAALGCLVKDYFPEPVTVSWNS
GALTSGVHTFPAVLQSSGLYSLSSVVTVPSSSLGTQTYTCNVNHKPSNTKVDKRVGERPAQ
GGRVSAGSQAQPSCLDASRLCSPSPGHQGRPRLTPHPEASARPTHAQGEGLLAFSTRLRAG
TGWMPLPQALHTQGQVLRSELPRAISRRTLPLTELKTPLGDTTHTCPRCPEPKSCDTPPPC
PRCPEPKSCDTPPPCPRCPEPKSCDTPPPCPRCPMISRTPEVTCVVVDVSHEDPEVQFKWY
VDGVEVHNAKTKLREEQYNSTFRVVSVLTVLHQDWLNGKEYKCKVSNKALPAPIEKTISKA
KMTKNQVSLTCLVKGFYPSDIAVEWESNGQPENNYNTTPPMLDSDGSFFLYSKLTVDKSRW
QQGNIFSCSVMHEALHNHYTQKSLSLSPGKSGGGGSCDLPQTHNLRNKRALTLLVQMRRLS
PLSCLKDRKDFGFPQEKVDAQQIKKAQAIPVLSELTQQILNIFTSKDSSAAWNATLLDSFC
NDLHQQLNDLQGCLMQQVGVQEFPLTQEDALLAVRKYFHRITVYLREKKHSPCAWEVVRAE
VWRALSSSANVLGRLREEK

Fig. 1C, cont'd.

αCD20-IgG3-muIFNα alpha helical linker - nucleic acid sequence

ATGTACTTGGGACTGAACTGTGTAATCATAGTTTTTCTCTTAAAAGGTGTCCAGAGTCAGG
TACAACTGCAGCAGCCTGGGGCTGAGCTGGTGAAGCCTGGGGCCTCAGTGAAGATGTCCTG
CAAGGCTTCTGGCTACACATTTACCAGTTACAATATGCACTGGGTAAAACAGACACCTGGT
CGGGGCCTGGAATGGATTGGAGCTATTTATCCGGAAATGGTGATACTTCCTACAATCAGA
AGTTCAAAGGCAAGGCCACATTGACTGCAGACAAATCCTCCAGCACAGCCTACATGCAGCT
CAGCAGCCTGACATCTGAGGACTCTGCGGTCTATTACTGTGCAAGATCGACTTACTACGGC
GGTGACTGGTACTTCAATGTCTGGGGCGCAGGGACCACGGTCACCGTCTCTGCAGCTAGCA
CCAAGGGCCCATCGGTCTTCCCCCTGGCGCCCTGCTCCAGGAGCACCTCTGGGGGCACAGC
GGCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACACCTGCAA
CGTGAATCACAAGCCCAGCAACACCAAGGTGGACAAGAGAGTTGGTGAGAGGCCAGCGCAG
GGAGGGAGGGTGTCTGCTGGAAGCCAGGCTCAGCCCTCCTGCCTGGACGCATCCCGGCTGT
GCAGTCCCAGCCCAGGGCACCAAGGCAGGCCCCGTCTGACTCCTCACCCGGAGGCCTCTGC
CCGCCCCACTCATGCTCAGGGAGAGGGTCTTCTGGCTTTTTCCACCAGGCTCCGGGCAGGC
ACAGGCTGGATGCCCCTACCCCAGGCCCTTCACACACAGGGGCAGGTGCTGCGCTCAGAGC
TGCCAAGAGCCATATCCAGGAGGACCCTGCCCCTGACCGAGCTCAAAACCCCACTTGGTGA
CACAACTCACACATGCCCACGGTGCCCAGAGCCCAAATCTTGTGACACACCTCCCCCGTGC
CCAAGGTGCCCAGAGCCCAAATCTTGTGACACACCTCCCCCGTGCCCAAGGTGCCCAGAGC
CCAAATCTTGTGACACACCTCCCCCGTGCCCAAGGTGCCCATGATTTCCCGGACCCCTGAG
GTCACGTGCGTGGTGGTGGACGTGAGCCACGAAGACCCCGAGGTCCAGTTCAAGTGGTACG
TGGACGGCGTGGAGGTGCATAATGCCAAGACAAAGCTGCGGGAGGAGCAGTACAACAGCAC
GTTCCGTGTGGTCAGCGTCCTCACCGTCCTGCACCAGGACTGGCTGAACGGCAAGGAGTAC
AAGTGCAAGGTCTCCAACAAAGCCCTCCCAGCCCCCATCGAGAAAACCATCTCCAAAGCCA
AAATGACCAAGAACCAGGTCAGCCTGACCTGCCTGGTCAAAGGCTTCTACCCCAGCGACAT
CGCCGTGGAGTGGGAGAGCAATGGGCAGCCGGAGAACAACTACAACACCACGCCTCCCATG
CTGGACTCCGACGGCTCCTTCTTCCTCTACAGCAAGCTCACCGTGGACAAGAGCAGGTGGC
AGCAGGGGAACATCTTCTCATGCTCCGTGATGCATGAGGCTCTGCACAACCACTACACGCA
GAAGAGCCTCTCCCTGTCTCCGGGTAAAGCAGAGGCCGCAGCTAAAGAGGCCGCAGCCAAA
GCGGGATCCTGTGACCTGCCTCAGACTCATAACCTCAGGAACAAGAGAGCCTTGACACTCC
TGGTACAAATGAGGAGACTCTCCCCTCTCCTGCCTGAAGGACAGGAAGGACTTTGGATT
CCCGCAGGAGAAGGTGGATGCCCAGCAGATCAAGAAGGCTCAAGCCATCCCTGTCCTGAGT
GAGCTGACCCAGCAGATCCTGAACATCTTCACATCAAAGGACTCATCTGCTGCTTGGAATG
CAACCCTCCTAGACTCATTCTGCAATGACCTCCACCAGCAGCTCAATGACCTGCAAGGTTG
TCTGATGCAGCAGGTGGGGGTGCAGGAATTCCCCTGACCCAGGAAGATGCCCTGCTGGCT
GTGAGGAAATACTTCCACAGGATCACTGTGTACCTGAGAGAGAAGAAACACAGCCCCTGTG
CCTGGGAGGTGGTCAGAGCAGAAGTCTGGAGAGCCCTGTCTTCCTCTGCCAATGTGCTGGG
AAGACTGAGAGAAGAGAAATGA

*Fig. 1D*

αCD20-IgG3-muIFNα alpha helical linker - amino acid sequence

MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASTKGPSVFPLAPCSRSTSGGTAALGCLVKDYFPEPVTVSWNS
GALTSGVHTFPAVLQSSGLYSLSSVVTVPSSSLGTQTYTCNVNHKPSNTKVDKRVGERPAQ
GGRVSAGSQAQPSCLDASRLCSPSPGHQGRPRLTPHPEASARPTHAQGEGLLAFSTRLRAG
TGWMPLPQALHTQGQVLRSELPRAISRRTLPLTELKTPLGDTTHTCPRCPEPKSCDTPPPC
PRCPEPKSCDTPPPCPRCPEPKSCDTPPPCPRCPMISRTPEVTCVVVDVSHEDPEVQFKWY
VDGVEVHNAKTKLREEQYNSTFRVVSVLTVLHQDWLNGKEYKCKVSNKALPAPIEKTISKA
KMTKNQVSLTCLVKGFYPSDIAVEWESNGQPENNYNTTPPMLDSDGSFFLYSKLTVDKSRW
QQGNIFSCSVMHEALHNHYTQKSLSLSPGKAEAAAKEAAAKAGSCDLPQTHNLRNKRALTL
LVQMRRLSPLSCLKDRKDFGFPQEKVDAQQIKKAQAIPVLSELTQQILNIFTSKDSSAAWN
ATLLDSFCNDLHQQLNDLQGCLMQQVGVQEFPLTQEDALLAVRKYFHRITVYLREKKHSPC
AWEVVRAEVWRALSSSANVLGRLREEK

*Fig. 1D, cont'd.*

αCD20-IgG3-huIFNα Gly₄Ser linker - nucleic acid sequence

```
ATGTACTTGGGACTGAACTGTGTAATCATAGTTTTTCTCTTAAAAGGTGTCCAGAGTCAGG
TACAACTGCAGCAGCCTGGGGCTGAGCTGGTGAAGCCTGGGGCCTCAGTGAAGATGTCCTG
CAAGGCTTCTGGCTACACATTTACCAGTTACAATATGCACTGGGTAAAACAGACACCTGGT
CGGGGCCTGGAATGGATTGGAGCTATTTATCCCGGAAATGGTGATACTTCCTACAATCAGA
AGTTCAAAGGCAAGGCCACATTGACTGCAGACAAATCCTCCAGCACAGCCTACATGCAGCT
CAGCAGCCTGACATCTGAGGACTCTGCGGTCTATTACTGTGCAAGATCGACTTACTACGGC
GGTGACTGGTACTTCAATGTCTGGGGCGCAGGGACCACGGTCACCGTCTCTGCAGCTAGCA
CCAAGGGCCCATCGGTCTTCCCCCTGGCGCCCTGCTCCAGGAGCACCTCTGGGGGCACAGC
GGCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACACCTGCAA
CGTGAATCACAAGCCCAGCAACACCAAGGTGGACAAGAGAGTTGGTGAGAGGCCAGCGCAG
GGAGGGAGGGTGTCTGCTGGAAGCCAGGCTCAGCCCTCCTGCCTGGACGCATCCGGCTGT
GCAGTCCCAGCCCAGGGCACCAAGGCAGGCCCCGTCTGACTCCTCACCCGGAGGCCTCTGC
CCGCCCCACTCATGCTCAGGGAGAGGGTCTTCTGGCTTTTTCCACCAGGCTCCGGGCAGGC
ACAGGCTGGATGCCCCTACCCCAGGCCCTTCACACACAGGGGCAGGTGCTGCGCTCAGAGC
TGCCAAGAGCCATATCCAGGAGGACCCTGCCCCTGACCGAGCTCAAAACCCCACTTGGTGA
CACAACTCACACATGCCCACGGTGCCCAGAGCCCAAATCTTGTGACACACCTCCCCGTGC
CCAAGGTGCCCAGAGCCCAAATCTTGTGACACACCTCCCCGTGCCCAAGGTGCCCAGAGC
CCAAATCTTGTGACACACCTCCCCGTGCCCAAGGTGCCCATGATTTCCCGGACCCCTGAG
GTCACGTGCGTGGTGGTGGACGTGAGCCACGAAGACCCCGAGGTCCAGTTCAAGTGGTACG
TGGACGGCGTGGAGGTGCATAATGCCAAGACAAAGCTGCGGGAGGAGCAGTACAACAGCAC
GTTCCGTGTGGTCAGCGTCCTCACCGTCCTGCACCAGGACTGGCTGAACGGCAAGGAGTAC
AAGTGCAAGGTCTCCAACAAAGCCCTCCCAGCCCCCATCGAGAAACCATCTCCAAAGCCAA
AATGACCAAGAACCAGGTCAGCCTGACCTGCCTGGTCAAAGGCTTCTACCCCAGCGACATC
GCCGTGGAGTGGGAGAGCAATGGGCAGCCGGAGAACAACTACAACACCACGCCTCCCATGC
TGGACTCCGACGGCTCCTTCTTCCTCTACAGCAAGCTCACCGTGGACAAGAGCAGGTGGCA
GCAGGGGAACATCTTCTCATGCTCCGTGATGCATGAGGCTCTGCACAACCACTACACGCAG
AAGAGCCTCTCCCTGTCTCCGGGTAAATCTGGTGGCGGTGGATCCTGTGATCTGCCTCAAA
CCCACAGCCTGGGTAGCAGGAGGACCTTGATGCTCCTGGCACAGATGAGGAGAATCTCTCT
TTTCTCCTGCTTGAAGGACAGACATGACTTTGGATTTCCCAGGAGGAGTTTGGCAACCAG
TTCCAAAAGGCTGAAACCATCCCTGTCCTCCATGAGATGATCCAGCAGATCTTCAATCTCT
TCAGCACAAAGGACTCATCTGCTGCTTGGGATGAGACCCTCCTAGACAAATTCTACACTGA
ACTCTACCAGCAGCTGAATGACCTGGAAGCCTGTGTGATACAGGGGGTGGGGGTGACAGAG
ACTCCCCTGATGAAGGAGGACTCCATTCTGGCTGTGAGGAAATACTTCCAAAGAATCACTC
TCTATCTGAAAGAGAAGAAATACAGCCCTTGTGCCTGGGAGGTTGTCAGAGCAGAAATCAT
GAGATCTTTTCTTTGTCAACAAACTTGCAAGAAAGTTTAAGAAGTAAGGAATGA
```

*Fig. 1E*

αCD20-IgG3-huIFNα Gly₄Ser linker - amino acid sequence

MYLGLNCVTIVFLLKGVQSQVQLQQPGAELVRPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASTKGPSVFPLAPCSRSTSGGTAALGCLVKDYFPEPVTVSWNS
GALTSGVHTFPAVLQSSGLYSLSSVVTVPSSSLGTQTYTCNVNHKPSNTKVDKRVGERPAQ
GGRVSAGSQAQPSCLDASRLCSPSPGHQGRPRLTPHPEASARPTHAQGEGLLAFSTRLRAG
TGWMPLPQALHTQGQVLRSELPRAISRRTLPLTELKTPLGDTTHTCPRCPEPKSCDTPPPC
PRCPEPKSCDTPPPCPRCPEPKSCDTPPPCPRCPMISRTPEVTCVVVDVSHEDPEVQFKWY
VDGVEVHNAKTKLREEQYNSTFRVVSVLTVLHQDWLNGKEYKCKVSNKALPAPIEKTISKA
KMTKNQVSLTCLVKGFYPSDIAVEWESNGQPENNYNTTPPMLDSDGSFFLYSKLTVDKSRW
QQGNIFSCSVMHEALHNHYTQKSLSLSPGKSGGGGSCDLPQTHSLGSRRTLMLLAQMRRIS
LFSCLKDRHDFGFPQEEFGNQFQKAETIPVLHEMIQQIFNLFSTKDSSAAWDETLLDKFYT
ELYQQLNDLEACVIQGVGVTETPLMKEDSILAVRKYFQRITLYLKEKKYSPCAWEVVRAEI
MRSFSLSTNLQESLRSKE

Fig. 1E, cont'd.

αCD20-IgG3-huIFNα alpha helical linker - nucleic acid sequence

```
ATGTACTTGGGACTGAACTGTGTAATCATAGTTTTTCTCTTAAAAGGTGTCCAGAGTCAGG
TACAACTGCAGCAGCCTGGGGCTGAGCTGGTGAAGCCTGGGGCCTCAGTGAAGATGTCCTG
CAAGGCTTCTGGCTACACATTTACCAGTACAATATGCACTGGGTAAAACAGACACCTGGT
CGGGGCCTGGAATGGATTGGAGCTATTTATCCGGAAATGGTGATACTTCCTACAATCAGA
AGTTCAAAGGCAAGGCCACATTGACTGCAGACAAATCCTCCAGCACAGCCTACATGCAGCT
CAGCAGCCTGACATCTGAGGACTCTGCGGTCTATTACTGTGCAAGATCGACTTACTACGGC
GGTGACTGGTACTTCAATGTCTGGGGCGCAGGGACCACGGTCACCGTCTCTGCAGCTAGCA
CCAAGGGCCCATCGGTCTTCCCCCTGGCGCCCTGCTCCAGGAGCACCTCTGGGGGCACAGC
GGCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACACCTGCAA
CGTGAATCACAAGCCCAGCAACACCAAGGTGGACAAGAGAGTTGGTGAGAGGCCAGCGCAG
GGAGGGAGGGTGTCTGCTGGAAGCCAGGCTCAGCCCTCCTGCCTGGACGCATCCGGCTGT
GCAGTCCCAGCCCAGGGCACCAAGGCAGGCCCCGTCTGACTCCTCACCGGAGGCCTCTGC
CCGCCCCACTCATGCTCAGGGAGAGGGTCTTCTGGCTTTTTCCACCAGGCTCCGGGCAGGC
ACAGGCTGGATGCCCCTACCCCAGGCCCTTCACACACAGGGGCAGGTGCTGCGCTCAGAGC
TGCCAAGAGCCATATCCAGGAGGACCCTGCCCCTGACCGAGCTCAAAACCCCACTTGGTGA
CACAACTCACACATGCCCACGGTGCCCAGAGCCCAAATCTTGTGACACACCTCCCCCGTGC
CCAAGGTGCCCAGAGCCCAAATCTTGTGACACACCTCCCCCGTGCCCAAGGTGCCCAGAGC
CCAAATCTTGTGACACACCTCCCCCGTGCCCAAGGTGCCCATGATTTCCCGGACCCCTGAG
GTCACGTGCGTGGTGGTGGACGTGAGCCACGAAGACCCCGAGGTCCAGTTCAAGTGGTACG
TGGACGGCGTGGAGGTGCATAATGCCAAGACAAAGCTGCGGGAGGAGCAGTACAACAGCAC
GTTCCGTGTGGTCAGCGTCCTCACCGTCCTGCACCAGGACTGGCTGAACGGCAAGGAGTAC
AAGTGCAAGGTCTCCAACAAAGCCCTCCCAGCCCCCATCGAGAAAACCATCTCCAAAGCCA
AAATGACCAAGAACCAGGTCAGCCTGACCTGCCTGGTCAAAGGCTTCTACCCCAGCGACAT
CGCCGTGGAGTGGGAGAGCAATGGGCAGCCGGAGAACAACTACAACACCACGCCTCCCATG
CTGGACTCCGACGGCTCCTTCTTCCTCTACAGCAAGCTCACCGTGGACAAGAGCAGGTGGC
AGCAGGGGAACATCTTCTCATGCTCCGTGATGCATGAGGCTCTGCACAACCACTACACGCA
GAAGAGCCTCTCCCTGTCTCCGGGTAAATCTGGTGGCGGTGGATCCTGTGATCTGCCTCAA
ACCCACAGCCTGGGTAGCAGGAGGACCTTGATGCTCCTGGCACAGATGAGGAGAATCTCTC
TTTTCTCCTGCTTGAAGGACAGACATGACTTTGGATTTCCCCAGGAGGAGTTTGGCAACCA
GTTCCAAAAGGCTGAAACCATCCCTGTCCTCCATGAGATGATCCAGCAGATCTTCAATCTC
TTCAGCACAAAGGACTCATCTGCTGCTTGGGATGAGACCCTCCTAGACAAATTCTACACTG
AACTCTACCAGCAGCTGAATGACCTGGAAGCCTGTGTGATACAGGGGGTGGGGGTGACAGA
GACTCCCCTGATGAAGGAGGACTCCATTCTGGCTGTGAGGAAATACTTCCAAAGAATCACT
CTCTATCTGAAAGAGAAGAAATACAGCCCTTGTGCCTGGGAGGTTGTCAGAGCAGAAATCA
TGAGATCTTTTCTTTGTCAACAAACTTGCAAGAAAGTTTAAGAAGTAAGGAATGA
```

*Fig. 1F*

αCD20-IgG3-huIFNα alpha helical linker - amino acid sequence

MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASTKGPSVFPLAPCSRSTSGGTAALGCLVKDYFPEPVTVSWNS
GALTSGVHTFPAVLQSSGLYSLSSVVTVPSSSLGTQTYTCNVNHKPSNTKVDKRVGERPAQ
GGRVSAGSQAQPSCLDASRLCSPSPGHQGRPRLTPHPEASARPTHAQGEGLLAFSTRLRAG
TGWMPLPQALHTQGQVLRSELPRAISRRTLPLTELKTPLGDTTHTCPRCPEPKSCDTPPPC
PRCPEPKSCDTPPPCPRCPEPKSCDTPPPCPRCPMISRTPEVTCVVVDVSHEDPEVQFKWY
VDGVEVHNAKTKLREEQYNSTFRVVSVLTVLHQDWLNGKEYKCKVSNKALPAPIEKTISKA
KMTKNQVSLTCLVKGFYPSDIAVEWESNGQPENNYNTTPPMLDSDGSFFLYSKLTVDKSRW
QQGNIFSCSVMHEALHNHYTQKSLSLSPGKSAEAAAKEAAAKACDLPQTHSLGSRRTLMLL
AQMRRISLFSCLKDRHDFGFPQEEFGNQFQKAETIPVLHEMIQQIFNLFSTKDSSAAWDET
LLDKFYTELYQQLNDLEACVIQGVGVTETPLMKEDSILAVRKYFQRITLYLKEKKYSPCAW
EVVRAEIMRSFSLSTNLQESLRSKE

*Fig. 1F, cont'd.*

αCD20-IgG1-muIFNα Gly₄Ser linker - nucleic acid sequence

```
ATGTACTTGGGACTGAACTGTGTAATCATAGTTTTTCTCTTAAAAGGTGTCCAGAGTCAGGTACAAC
TGCAGCAGCCTGGGGCTGAGCTGGTGAAGCCTGGGGCCTCAGTGAAGATGTCCTGCAAGGCTTCTGG
CTACACATTTACCAGTTACAATATGCACTGGGTAAAACAGACACCTGGTCGGGGCCTGGAATGGATT
GGAGCTATTTATCCCGGAAATGGTGATACTTCCTACAATCAGAAGTTCAAAGGCAAGGCCACATTGA
CTGCAGACAAATCCTCCAGCACAGCCTACATGCAGCTCAGCAGCCTGACATCTGAGGACTCTGCGGT
CTATTACTGTGCAAGATCGACTTACTACGGCGGTGACTGGTACTTCAATGTCTGGGGCGCAGGGACC
ACGGTCACCGTCTCTGCAGCTAGCCAACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGGAGCC
CAAATCTTGTGACAAAACTCACACATGCCCACCGTGCCCAATGATCTCCCGGACCCCTGAGGTCACA
TGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGGGTGGTCAGCGT
CCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGTGGGACCCGTGGGGTGCGAGGGCCAC
ATGGACAGAGGCCGGCTCGGCCCACCCTCTGCCCTGAGAGTGACCGCTGTACCAACCTCTGTCCTAC
AGGGCAGCCCCGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAGAGCAATG
GGCAGCCGGAGAACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATCTGGTGGCGGTG
GATCCTGTGACCTGCCTCAGACTCATAACCTCAGGAACAAGAGAGCCTTGACACTCCTGGTACAAAT
GAGGAGACTCTCCCCTCTCCTGCCTGAAGGACAGGAAGGACTTTGGATTCCCGCAGGAGAAGGTG
GATGCCCAGCAGATCAAGAAGGCTCAAGCCATCCCTGTCCTGAGTGAGCTGACCCAGCAGATCCTGA
ACATCTTCACATCAAAGGACTCATCTGCTGCTTGGAATGCAACCCTCCTAGACTCATTCTGCAATGA
CCTCCACCAGCAGCTCAATGACCTGCAAGGTTGTCTGATGCAGCAGGTGGGGGTGCAGGAATTTCCC
CTGACCCAGGAAGATGCCCTGCTGGCTGTGAGGAAATACTTCCACAGGATCACTGTGTACCTGAGAG
AGAAGAAACACAGCCCCTGTGCCTGGGAGGTGGTCAGAGCAGAAGTCTGGAGAGCCCTGTCTTCCTC
TGCCAATGTGCTGGGAAGACTGAGAGAAGAGAAATGA
```

αCD20-IgG1-muIFNα Gly₄Ser linker - amino acid sequence

```
MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASQPRAHRSSPWHPPPRAPLGAQRPWAAWSRTTSPNREPKSCD
KTHTCPPCPMISRTPEVTCVVVDVSHEDPEVKFNWYVDGVEVHNAKTKPREEQYNSTYRVV
SVLTVLHQDWLNGKEYKCKVSNKALPAPIEKTISKAKGGTRGVRGPHGQRPARPTLCPESD
RCTNLCPTGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKSGGGGSC
DLPQTHNLRNKRALTLLVQMRRLSPLSCLKDRKDFGFPQEKVDAQQIKKAQAIPVLSELTQ
QILNIFTSKDSSAAWNATLLDSFCNDLHQQLNDLQGCLMQQVGVQEFPLTQEDALLAVRKY
FHRITVYLREKKHSPCAWEVVRAEVWRALSSSANVLGRLREEK
```

*Fig. 1G*

αCD20-IgG1-muIFNα alpha helical linker - nucleic acid sequence

ATGTACTTGGGACTGAACTGTGTAATCATAGTTTTTCTCTTAAAAGGTGTCCAGAGTCAGGTACAAC
TGCAGCAGCCTGGGGCTGAGCTGGTGAAGCCTGGGGCCTCAGTGAAGATGTCCTGCAAGGCTTCTGG
CTACACATTTACCAGTTACAATATGCACTGGGTAAAACAGACACCTGGTCGGGGCCTGGAATGGATT
GGAGCTATTTATCCCGGAAATGGTGATACTTCCTACAATCAGAAGTTCAAAGGCAAGGCCACATTGA
CTGCAGACAAATCCTCCAGCACAGCCTACATGCAGCTCAGCAGCCTGACATCTGAGGACTCTGCGGT
CTATTACTGTGCAAGATCGACTTACTACGGCGGTGACTGGTACTTCAATGTCTGGGGCGCAGGGACC
ACGGTCACCGTCTCTGCAGCTAGCCAACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGGAGCC
CAAATCTTGTGACAAAACTCACACATGCCCACCGTGCCCAATGATCTCCCGGACCCCTGAGGTCACA
TGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGGGTGGTCAGCGT
CCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGTGGGACCCGTGGGGTGCGAGGGCCAC
ATGGACAGAGGCCGGCTCGGCCCACCCTCTGCCCTGAGAGTGACCGCTGTACCAACCTCTGTCCTAC
AGGGCAGCCCCGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAGAGCAATG
GGCAGCCGGAGAACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATCTGGTGGCGGTG
GATCCTGTGACCTGCCTCAGACTCATAACCTCAGGAACAAGAGAGCCTTGACACTCCTGGTACAAAT
GAGGAGACTCTCCCCTCTCTCCTGCCTGAAGGACAGGAAGGACTTTGGATTCCCGCAGGAGAAGGTG
GATGCCCAGCAGATCAAGAAGGCTCAAGCCATCCCTGTCCTGAGTGAGCTGACCCAGCAGATCCTGA
ACATCTTCACATCAAAGGACTCATCTGCTGCTTGGAATGCAACCCTCCTAGACTCATTCTGCAATGA
CCTCCACCAGCAGCTCAATGACCTGCAAGGTTGTCTGATGCAGCAGGTGGGGGTGCAGGAATTTCCC
CTGACCCAGGAAGATGCCCTGCTGGCTGTGAGGAAATACTTCCACAGGATCACTGTGTACCTGAGAG
AGAAGAAACACAGCCCCTGTGCCTGGGAGGTGGTCAGAGCAGAAGTCTGGAGAGCCCTGTCTTCCTC
TGCCAATGTGCTGGGAAGACTGAGAGAAGAGAAATGA

αCD20-IgG1-muIFNα alpha helical linker - amino acid sequence

MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASQPRAHSSPWHPPPRAPLGAQRPWAAWSRTTSPNREPKSCD
KTHTCPPCPMISRTPEVTCVVVDVSHEDPEVKFNWYVDGVEVHNAKTKPREEQYNSTYRVV
SVLTVLHQDWLNGKEYKCKVSNKALPAPIEKTISKAKGGTRGVRGPHGQRPARPTLCPESD
RCTNLCPTGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKS<u>AEAAAK</u>
<u>EAAAKA</u>CDLPQTHNLRNKRALTLLVQMRRLSPLSCLKDRKDFGFPQEKVDAQQIKKAQAIP
VLSELTQQILNIFTSKDSSAAWNATLLDSFCNDLHQQLNDLQGCLMQQVGVQEFPLTQEDA
LLA

αCD20-IgG1-huIFNα Gly₄Ser linker - nucleic acid sequence

```
ATGTACTTGGGACTGAACTGTGTAATCATAGTTTTTCTCTTAAAAGGTGTCCAGAGTCAGGTACAAC
TGCAGCAGCCTGGGGCTGAGCTGGTGAAGCCTGGGGCTCAGTGAAGATGTCCTGCAAGGCTTCTGG
CTACACATTTACCAGTTACAATATGCACTGGGTAAAACAGACACCTGGTCGGGGCCTGGAATGGATT
GGAGCTATTTATCCCGGAAATGGTGATACTTCCTACAATCAGAAGTTCAAAGGCAAGGCCACATTGA
CTGCAGACAAATCCTCCAGCACAGCCTACATGCAGCTCAGCAGCCTGACATCTGAGGACTCTGCGGT
CTATTACTGTGCAAGATCGACTTACTACGGCGGTGACTGGTACTTCAATGTCTGGGGCGCAGGGACC
ACGGTCACCGTCTCTGCAGCTAGCCAACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGGAGCC
CAAATCTTGTGACAAAACTCACACATGCCCACCGTGCCCAATGATCTCCCGGACCCCTGAGGTCACA
TGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGGGTGGTCAGCGT
CCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGTGGGACCGTGGGGTGCGAGGGCCAC
ATGGACAGAGGCCGGCTCGGCCCACCCTCTGCCCTGAGAGTGACCGCTGTACCAACCTCTGTCCTAC
AGGGCAGCCCTGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAGAGCAATG
GGCAGCCGGAGAACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATCTGGTGGCGGTG
GATCCTGTGATCTGCCTCAAACCCACAGCCTGGGTAGCAGGAGGACCTTGATGCTCCTGGCACAGAT
GAGGAGAATCTCTCTTTTCTCCTGCTTGAAGGACAGACATGACTTTGGATTTCCCCAGGAGGAGTTT
GGCAACCAGTTCCAAAAGGCTGAAACCATCCCTGTCCTCCATGAGATGATCCAGCAGATCTTCAATC
TCTTCAGCACAAAGGACTCATCTGCTGCTTGGGATGAGACCCTCCTAGACAAATTCTACACTGAACT
CTACCAGCAGCTGAATGACCTGGAAGCCTGTGTGATACAGGGGGTGGGGGTGACAGAGACTCCCCTG
ATGAAGGAGGACTCCATTCTGGCTGTGAGGAAATACTTCCAAAGAATCACTCTCTATCTGAAAGAGA
AGAAATACAGCCCTTGTGCCTGGGAGGTTGTCAGAGCAGAAATCATGAGATCTTTTTCTTTGTCAAC
AAACTTGCAAGAAAGTTTAAGAAGTAAGGAATGA
```

αCD20-IgG1-huIFNα Gly₄Ser linker - amino acid sequence

```
MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASQPRAHRSSPWHPPPRAPLGAQRPWAAWSRTTSPNREPKSCD
KTHTCPPCPMISRTPEVTCVVVDVSHEDPEVKFNWYVDGVEVHNAKTKPREEQYNSTYRVV
SVLTVLHQDWLNGKEYKCKVSNKALPAPIEKTISKAKGGTRGVRGPHGQRPARPTLCPESD
RCTNLCPTGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKSGGGGSC
DLPQTHSLGSRRTLMLLAQMRRISLFSCLKDRHDFGFPQEEFGNQFQKAETIPVLHEMIQQ
IFNLFSTKDSSAAWDETLLDKFYTELYQQLNDLEACVIQGVGVTETPLMKEDSILAVRKYF
QRITLYLKEKKYSPCAWEVVRAEIMRSFSLSTNLQESLRSKE
```

*Fig. 1I*

αCD20-IgG1-huIFNα alpha helical linker - nucleic acid sequence

```
ATGTACTTGGGACTGAACTGTGTAATCATAGTTTTTCTCTTAAAAGGTGTCCAGAGTCAGGTACAAC
TGCAGCAGCCTGGGGCTGAGCTGGTGAAGCCTGGGGCTCAGTGAAGATGTCCTGCAAGGCTTCTGG
CTACACATTACCAGTTACAATATGCACTGGGTAAAACAGACACCTGGTCGGGGCCTGGAATGGATT
GGAGCTATTTATCCCGGAAATGGTGATACTTCCTACAATCAGAAGTTCAAAGGCAAGGCCACATTGA
CTGCAGACAAATCCTCCAGCACAGCCTACATGCAGCTCAGCAGCCTGACATCTGAGGACTCTGCGGT
CTATTACTGTGCAAGATCGACTTACTACGGCGGTGACTGGTACTTCAATGTCTGGGGCGCAGGGACC
ACGGTCACCGTCTCTGCAGCTAGCCAACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGGAGCC
CAAATCTTGTGACAAAACTCACACATGCCCACCGTGCCCAATGATCTCCCGGACCCCTGAGGTCACA
TGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGGGTGGTCAGCGT
CCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGTGGGACCCGTGGGGTGCGAGGGCCAC
ATGGACAGAGGCCGGCTCGGCCCACCCTCTGCCCTGAGAGTGACCGCTGTACCAACCTCTGTCCTAC
AGGGCAGCCCCGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAGAGCAATG
GGCAGCCGGAGAACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAAGCAGAGGCCGCAG
CTAAAGAGGCCGCAGCCAAAGCGGGATCCTGTGATCTGCCTCAAACCCACAGCCTGGGTAGCAGGAG
GACCTTGATGCTCCTGGCACAGATGAGGAGAATCTCTCTTTTCTCCTGCTTGAAGGACAGACATGAC
TTGGATTTCCCCAGGAGGAGTTTGGCAACCAGTTCCAAAAGGCTGAAACCATCCCTGTCCTCCATG
AGATGATCCAGCAGATCTTCAATCTCTTCAGCACAAAGGACTCATCTGCTGCTTGGGATGAGACCCT
CCTAGACAAATTCTACACTGAACTCTACCAGCAGCTGAATGACCTGGAAGCCTGTGTGATACAGGGG
GTGGGGGTGACAGAGACTCCCCTGATGAAGGAGGACTCCATTCTGGCTGTGAGGAAATACTTCCAAA
GAATCACTCTCTATCTGAAAGAGAAGAAATACAGCCCTTGTGCCTGGGAGGTTGTCAGAGCAGAAAT
CATGAGATCTTTTCTTTGTCAACAAACTTGCAAGAAAGTTTAAGAAGTAAGGAATGA
```

αCD20-IgG1-huIFNα alpha helical linker - amino acid sequence

```
MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASQPRAHRSSPWHPPPPAPLGAQRPWAAWSRTTSPNREPKSCD
KTHTCPPCPMISRTPEVTCVVVDVSHEDPEVKFNWYVDGVEVHNAKTKPREEQYNSTYRVV
SVLTVLHQDWLNGKEYKCKVSNKALPAPIEKTISKAKGGTRGVRGPHGQPAPPTLCPESD
RCTNLCPTGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK**AEAAAKE
AAAKA**GSCDLPQTHSLGSRRTLMLLAQMRRISLFSCLKDRHDFGFPQEEFGNQFQKAETIP
VLHEMIQQIFNLFSTKDSSAAWDETLLDKFYTELYQQLNDLEACVIQGVGVTETPLMKEDS
ILAVRKYFQRITLYLKEKKYSPCAWEVVRAEIMRSFSLSTNLQESLRSKE
```

*Fig. 1J*

αHer2/neu light chain - nucleic acid sequence

ATGGGATGGAGCTGGGTAATCCTCTTTCTCCTGTCAGTAACTGCAGGTGTCCACTCCCAGT
CTGTGTTGACGCAGCCGCCCTCAGTGTCTGCGGCCCCAGGACAGAAGGTCACCATCTCCTG
CTCTGGAAGCAGCTCCAACATTGGGAATAATTATGTATCCTGGTACCAGCAGCTCCCAGGA
ACAGCCCCCAAACTCCTCATCTATGATCACACCAATCGGCCCGCAGGGGTCCCTGACCGAT
TCTCTGGCTCCAAGTCTGGCACCTCAGCCTCCCTGGCCATCAGTGGGTTCCGGTCCGAGGA
TGAGGCTGATTATTACTGTGCCTCCTGGGACTACACCCTCTCGGGCTGGGTGTTCGGAGGA
GGGACCAAGGTCACCGTCCTAGGTGAG

αHer2/neu light chain - Amino acid sequence

MGWSWVILFLLSVTAGVHSQSVLTQPPSVSAAPGQKVTISCSGSSSNIGNNYVSWYQQLPG
TAPKLLIYDHTNRPAGVPDRFSGSKSGTSASLAISGFRSEDEADYYCASWDYTLSGWVFGG
GTKVTVLGE

*Fig. 1K*

αHer2/neu-IgG1-muIFNα glyser linker - Nucleic acid sequence

```
ATGGGATGGAGCTGGGTAATGCATCTTTCTCCTGTCAGTAACTGCAGATGCCCGGGAAAGGCCTGGA
GTACATGGGGCTCATCTATCCTGGTGACTCTGACACCAAATACAGCCCGTCCTTCCAAGGCCAGGTC
ACCATCTCAGTCGACAAGTCCGTCAGCACTGCCTACTTGCAATGGAGCAGTCTGAAGCCCTCGGACA
GCGCCGTGTATTTTTGTGCGAGACATGACGTGGGATATTGCACCGACCGGACTTGCGCAAAGTGGCC
TGAATACTTCCAGCATTGGGGCCAGGGCACCCTGGTCACCGTCTCCTCAGCTAGCCAACCAAGGGCC
CATCGGTCTTCCCCCTGGCACCCTCCTCCAAGAGCACCTCTGGGGGCACAGCGGCCCTGGGCTGCCT
GGTCAAGGACTACTTCCCCGAACCGGGAGCCCAAATCTTGTGACAAAACTCACACATGCCCACCGTG
CCCAATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGCGGGAGGAGC
AGTACAACAGCACGTACCGGGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCC
AAAGGTGGGACCCGTGGGGTGCGAGGGCCACATGGACAGAGGCCGGCTCGGCCCACCCTCTGCCCTG
AGAGTGACCGCTGTACCAACCTCTGTCCTACAGGGCAGCCCCGAGAACCACAGGTGTACACCCTGCC
CCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACACGCAGAAGAGCCTC
TCCCTGTCTCCGGGTAAATCTGGTGGCGGTGGATCCTGTGACCTGCCTCAGACTCATAACCTCAGGA
ACAAGAGAGCCTTGACACTCCTGGTACAAATGAGGAGACTCTCCCCTCTCTCCTGCCTGAAGGACAG
GAAGGACTTTGGATTCCCGCAGGAGAAGGTGGATGCCCAGCAGATCAAGAAGGCTCAAGCCATCCCT
GTCCTGAGTGAGCTGACCCAGCAGATCCTGAACATCTTCACATCAAAGGACTCATCTGCTGCTTGGA
ATGCAACCCTCCTAGACTCATTCTGCAATGACCTCCACCAGCAGCTCAATGACCTGCAAGGTTGTCT
GATGCAGCAGGTGGGGGTGCAGGAATTTCCCCTGACCCAGGAAGATGCCCTGCTGGCTGTGAGGAAA
TACTTCCACAGGATCACTGTGTACCTGAGAGAGAAGAAACACAGCCCCTGTGCCTGGGAGGTGGTCA
GAGCAGAAGTCTGGAGAGCCCTGTCTTCCTCTGCCAATGTGCTGGGAAGACTGAGAGAAGAGAAATG
A
```

αHer2/neu-IgG1-muIFNα glyser linker - Amino acid sequence

MGWSWVMHLSPVSNCMPGKGLEYMGLIYPGDSDTKYSPSFQGQVTISVDKSVSTAYLQWSS
LKPSDSAVYFCARHDVGYCTDRTCAKWPEYFQHWGQGTLVTVSSASQPRAHRSSPWHPPPR
APLGAQRPWAAWSRTTSPNREPKSCDKTHTCPPCPMISRTPEVTCVVVDVSHEDPEVKFNW
YVDGVEVHNAKTKPREEQYNSTYRVVSVLTVLHQDWLNGKEYKCKVSNKALPAPIEKTISK
AKGGTRGVRGPHGQRPARPTLCPESDRCTNLCPTGQPREPQVYTLPPSRDELTKNQVSLTC
LVKGFYPSDIAVEWESNGQPENNYKTTPPVLDSDGSFFLYSKLTVDKSRWQQGNVFSCSVM
HEALHNHYTQKSLSLSPGKSGGGGSCDLPQTHNLRNKRALTLLVQMRRLSPLSCLKDRKDF
GFPQEKVDAQQIKKAQAIPVLSELTQQILNIFTSKDSSAAWNATLLDSFCNDLHQQLNDLQ
GCLMQQVGVQEFPLTQEDALLAVRKYFHRITVYLREKKHSPCAWEVVRAEVWRALSSSANV
LGRLREEK

*Fig. 1L*

αHer2/neu-IgG1-muIFNα alpha helical linker - nucleic acid sequence

ATGGGATGGAGCTGGGTAATGCATCTTTCTCCTGTCAGTAACTGCAGATGCCCGGGAAAGGCCTGGA
GTACATGGGGCTCATCTATCCTGGTGACTCTGACACCAAATACAGCCCGTCCTTCCAAGGCCAGGTC
ACCATCTCAGTCGACAAGTCCGTCAGCACTGCCTACTTGCAATGGAGCAGTCTGAAGCCCTCGGACA
GCGCCGTGTATTTTTGTGCGAGACATGACGTGGGATATTGCACCGACCGGACTTGCGCAAAGTGGCC
TGAATACTTCCAGCATTGGGGCCAGGGCACCCTGGTCACCGTCTCCTCAGCTAGCCAACCAAGGGCC
CATCGGTCTTCCCCCTGGCACCCTCCTCCAAGAGCACCTCTGGGGGCACAGCGGCCCTGGGCTGCCT
GGTCAAGGACTACTTCCCCGAACCGGGAGCCCAAATCTTGTGACAAAACTCACACATGCCCACCGTG
CCCAATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGCGGGAGGAGC
AGTACAACAGCACGTACCGGGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCC
AAAGGTGGGACCCGTGGGGTGCGAGGGCCACATGGACAGAGGCCGGCTCGGCCCACCCTCTGCCCTG
AGAGTGACCGCTGTACCAACCTCTGTCCTACAGGGCAGCCCCGAGAACCACAGGTGTACACCCTGCC
CCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACACGCAGAAGAGCCTC
TCCCTGTCTCCGGGTAAAGCAGAGGCCGCAGCTAAAGAGGCCGCAGCCAAAGCGGGATCCTGTGACC
TGCCTCAGACTCATAACCTCAGGAACAAGAGAGCCTTGACACTCCTGGTACAAATGAGGAGACTCTC
CCCTCTCTCCTGCCTGAAGGACAGGAAGGACTTTGGATTCCCGCAGGAGAAGGTGGATGCCCAGCAG
ATCAAGAAGGCTCAAGCCATCCCTGTCCTGAGTGAGCTGACCCAGCAGATCCTGAACATCTTCACAT
CAAAGGACTCATCTGCTGCTTGGAATGCAACCCTCCTAGACTCATTCTGCAATGACCTCCACCAGCA
GCTCAATGACCTGCAAGGTTGTCTGATGCAGCAGGTGGGGGTGCAGGAATTTCCCCTGACCCAGGAA
GATGCCCTGCTGGCTGTGAGGAAATACTTCCACAGGATCACTGTGTACCTGAGAGAGAAGAAACACA
GCCCCTGTGCCTGGGAGGTGGTCAGAGCAGAAGTCTGGAGAGCCCTGTCTTCCTCTGCCAATGTGCT
GGGAAGACTGAGAGAAGAGAAATGA

αHer2/neu-IgG1-muIFNα alpha helical linker - amino acid sequence

MGWSWVMHLSPVSNCMPGKGLEYMGLIYPGDSDTKYSPSFQGQVTISVDKSVSTAYLQWSS
LKPSDSAVYFCARHDVGYCTDRTCAKWPEYFQHWGQGTLVTVSSASQPRAHRSSPWHPPPR
APLGAQRPWAAWSRTTSPNREPKSCDKTHTCPPCPMISRTPEVTCVVVDVSHEDPEVKFNW
YVDGVEVHNAKTKPREEQYNSTYRVVSVLTVLHQDWLNGKEYKCKVSNKALPAPIEKTISK
AKGGTRGVRGPHGQRPARPTLCPESDRCTNLCPTGQPREPQVYTLPPSRDELTKNQVSLTC
LVKGFYPSDIAVEWESNGQPENNYKTTPPVLDSDGSFFLYSKLTVDKSRWQQGNVFSCSVM
HEALHNHYTQKSLSLSPGKSAEAAAKEAAAKACDLPQTHNLRNKRALTLLVQMRRLSPLSC
LKDRKDFGFPQEKVDAQQIKKAQAIPVLSELQQILNIFTSKDSSAAWNATLLDSFCNDLH
QQLNDLQGCLMQQVGVQEFPLTQEDALLAVRKYFHRITVYLREKKHSPCAWEVVRAEVWRA
LSSSANVLGRLREEK

*Fig. 1M*

αHer2/neu-IgG1-huIFNα glyser linker - nucleic acid sequence

```
ATGGGATGGAGCTGGGTAATGCATCTTTCTCCTGTCAGTAACTGCAGATGCCCGGGAAAGGCCTGGA
GTACATGGGGCTCATCTATCCTGGTGACTCTGACACCAAATACAGCCCGTCCTTCCAAGGCCAGGTC
ACCATCTCAGTCGACAAGTCCGTCAGCACTGCCTACTTGCAATGGAGCAGTCTGAAGCCCTCGGACA
GCGCCGTGTATTTTGTGCGAGACATGACGTGGGATATTGCACCGACCGGACTTGCGCAAAGTGGCC
TGAATACTTCCAGCATTGGGGCCAGGGCACCCTGGTCACCGTCTCCTCAGCTAGCCAACCAAGGGCC
CATCGGTCTTCCCCCTGGCACCCTCCTCCAAGAGCACCTCTGGGGGCACAGCGGCCCTGGGCTGCCT
GGTCAAGGACTACTTCCCCGAACCGGGAGCCCAAATCTTGTGACAAAACTCACACATGCCCACCGTG
CCCAATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGCGGGAGGAGC
AGTACAACAGCACGTACCGGGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCC
AAAGGTGGGACCCGTGGGGTGCGAGGGCCACATGGACAGAGGCCGGCTCGGCCCACCCTCTGCCCTG
AGAGTGACCGCTGTACCAACCTCTGTCCTACAGGGCAGCCCCGAGAACCACAGGTGTACACCCTGCC
CCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACACGCAGAAGAGCCTC
TCCCTGTCTCCGGGTAAATCTGGTGGCGGTGGATCCTGTGATCTGCCTCAAACCCACAGCCTGGGTA
GCAGGAGGACCTTGATGCTCCTGGCACAGATGAGGAGAATCTCTCTTTTCTCCTGCTTGAAGGACAG
ACATGACTTTGGATTTCCCCAGGAGGAGTTTGGCAACCAGTTCCAAAAGGCTGAAACCATCCCTGTC
CTCCATGAGATGATCCAGCAGATCTTCAATCTCTTCAGCACAAAGGACTCATCTGCTGCTTGGGATG
AGACCCTCCTAGACAAATTCTACACTGAACTCTACCAGCAGCTGAATGACCTGGAAGCCTGTGTGAT
ACAGGGGGTGGGGGTGACAGAGACTCCCCTGATGAAGGAGGACTCCATTCTGGCTGTGAGGAAATAC
TTCCAAAGAATCACTCTCTATCTGAAAGAGAAGAAATACAGCCCTTGTGCCTGGGAGGTTGTCAGAG
CAGAAATCATGAGATCTTTTCTTTGTCAACAAACTTGCAAGAAAGTTTAAGAAGTAAGGAATGA
```

αHer2/neu-IgG1-huIFNα glyser linker - nucleic acid sequence

```
MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASQPRAHRSSPWHPPPRAPLGAQRPWAAWSRTTSPNREPKSCD
KTHTCPPCPMISRTPEVTCVVVDVSHEDPEVKFNWYVDGVEVHNAKTKPREEQYNSTYRVV
SVLTVLHQDWLNGKEYKCKVSNKALPAPIEKTISKAKGGTRGVRGPHGQRPARPTLCPESD
RCTNLCPTGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKSGGGGSC
DLPQTHSLGSRRTLMLLAQMRRISLFSCLKDRHDFGFPQEEFGNQFQKAETIPVLHEMIQQ
IFNLFSTKDSSAAWDETLLDKFYTELYQQLNDLEACVIQGVGVTETPLMKEDSILAVRKYF
QRITLYLKEKKYSPCAWEVVRAEIMRSFSLSTNLQESLRSKE
```

*Fig. 1N*

αHer2/neu-IgG1-huIFNα alpha helical linker - nucleic acid sequence

ATGGGATGGAGCTGGGTAATGCATCTTTCTCCTGTCAGTAACTGCAGATGCCCGGGAAAGGCCTGGA
GTACATGGGGCTCATCTATCCTGGTGACTCTGACACCAAATACAGCCCGTCCTTCCAAGGCCAGGTC
ACCATCTCAGTCGACAAGTCCGTCAGCACTGCCTACTTGCAATGGAGCAGTCTGAAGCCCTCGGACA
GCGCCGTGTATTTTGTGCGAGACATGACGTGGATATTGCACCGACCGGACTTGCGCAAAGTGGCC
TGAATACTTCCAGCATTGGGGCCAGGGCACCCTGGTCACCGTCTCCTCAGCTAGCCAACCAAGGGCC
CATCGGTCTTCCCCCTGGCACCCTCCTCCAAGAGCACCTCTGGGGGCACAGCGGCCCTGGGCTGCCT
GGTCAAGGACTACTTCCCCGAACCGGGAGCCCAAATCTTGTGACAAAACTCACACATGCCCACCGTG
CCCAATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGCGGGAGGAGC
AGTACAACAGCACGTACCGGGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCC
AAAGGTGGGACCCGTGGGGTGCGAGGGCCACATGGACAGAGGCCGGCTCGGCCCACCCTCTGCCCTG
AGAGTGACCGCTGTACCAACCTCTGTCCTACAGGGCAGCCCCGAGAACCACAGGTGTACACCCTGCC
CCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACACGCAGAAGAGCCTC
TCCCTGTCTCCGGGTAAAGCAGAGGCCGCAGCTAAAGAGGCCGCAGCCAAAGCGGGATCCTGTGATC
TGCCTCAAACCCACAGCCTGGGTAGCAGGAGGACCTTGATGCTCCTGGCACAGATGAGGAGAATCTC
TCTTTTCTCCTGCTTGAAGGACAGACATGACTTTGGATTTCCCCAGGAGGAGTTTGGCAACCAGTTC
CAAAAGGCTGAAACCATCCCTGTCCTCCATGAGATGATCCAGCAGATCTTCAATCTCTTCAGCACAA
AGGACTCATCTGCTGCTTGGGATGAGACCCTCCTAGACAAATTCTACACTGAACTCTACCAGCAGCT
GAATGACCTGGAAGCCTGTGTGATACAGGGGGTGGGGGTGACAGAGACTCCCCTGATGAAGGAGGAC
TCCATTCTGGCTGTGAGGAAATACTTCCAAAGAATCACTCTCTATCTGAAAGAGAAGAAATACAGCC
CTTGTGCCTGGGAGGTTGTCAGAGCAGAAATCATGAGATCTTTTCTTTGTCAACAAACTTGCAAGA
AAGTTTAAGAAGTAAGGAATGA

αHer2/neu-IgG1-huIFNα alpha helical linker - amino acid sequence

MYLGLNCVIIVFLLKGVQSQVQLQQPGAELVKPGASVKMSCKASGYTFTSYNMHWVKQTPG
RGLEWIGAIYPGNGDTSYNQKFKGKATLTADKSSSTAYMQLSSLTSEDSAVYYCARSTYYG
GDWYFNVWGAGTTVTVSAASQPRAHRSSPWHPPPRAPLGAQRPWAAWSRTTSPNREPKSCD
KTHTCPPCPMISRTPEVTCVVVDVSHEDPEVKFNWYVDGVEVHNAKTKPREEQYNSTYRVV
SVLTVLHQDWLNGKEYKCKVSNKALPAPIEKTISKAKGGTRGVRGPHGQRPARPTLCPESD
RCTNLCPTGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKSAEAAAK
EAAAKACDLPQTHSLGSRRTLMLLAQMRRISLFSCLKDRHDFGFPQEEFGNQFQKAETIPV
LHEMIQQIFNLFSTKDSSAAWDETLLDKFYTELYQQLNDLEACVIQGVGVTETPLMKEDSI
LAVRKYFQRITLYLKEKKYSPCAWEVVRAEIMRSFSLSTNLQESLRSKE

*Fig. 1o*

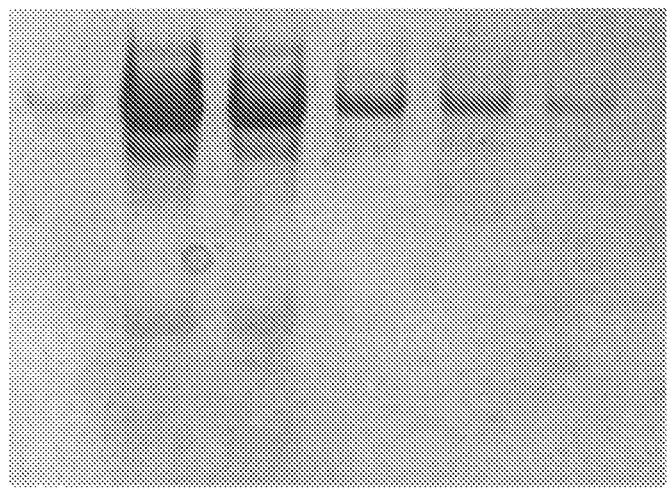
phosphate gel (non-reducing)
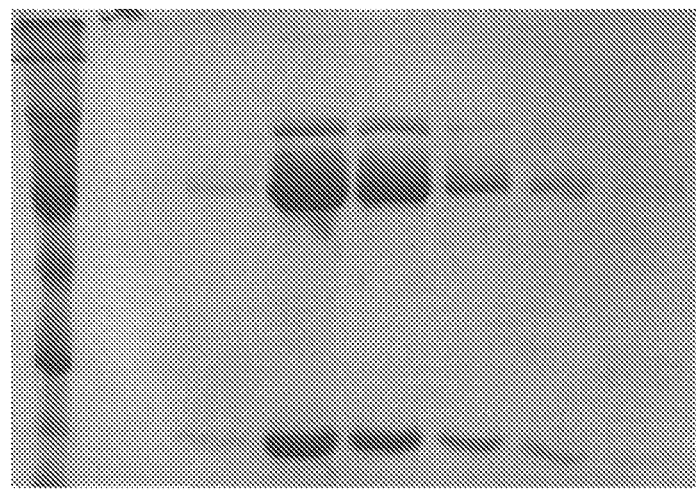
tris-glycine gel (reducing)
*Fig. 10*

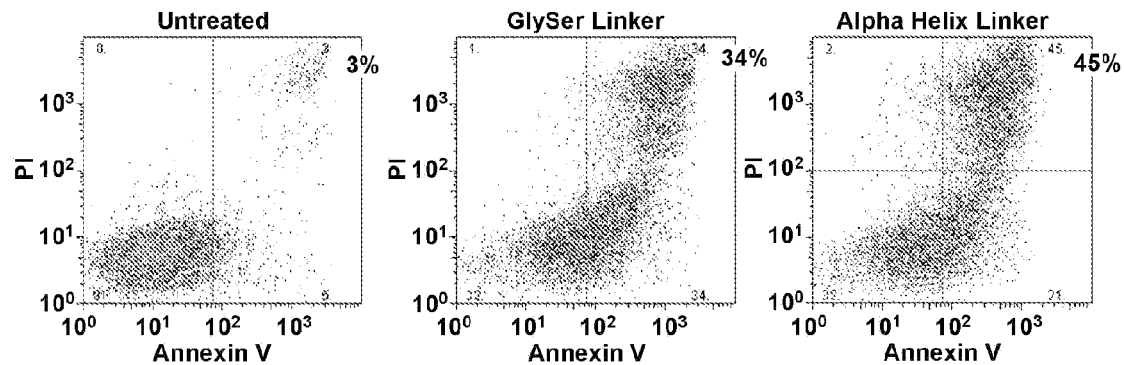

*Fig. 21*

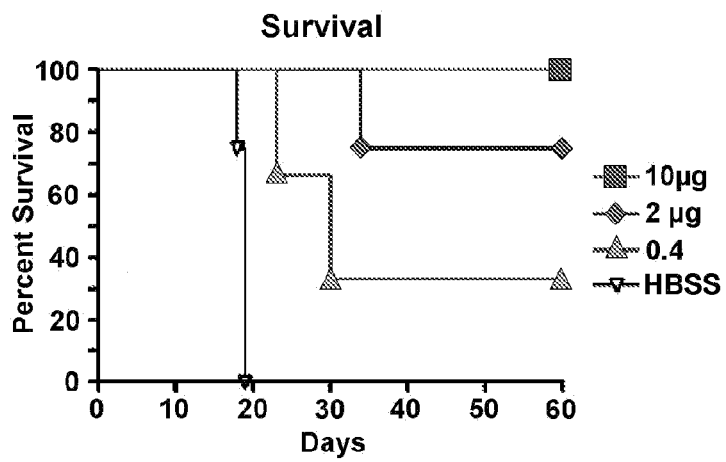

| Comparison of Survival curves | HBSS vs 10 ug | Comparison of Survival curves | HBSS vs 2 ug |
|---|---|---|---|
| Logrank Test | | Logrank Test | |
| Chi square | 6.628 | Chi square | 6.628 |
| df | 1 | df | 1 |
| P value | 0.0100 | P value | 0.0100 |
| P value summary | * | P value summary | * |
| Are the survival curves different? | yes | Are the survival curves different? | yes |
| Comparison of Survival curves | HBSS vs 0.4 ug | Comparison of Survival curves | 0.4 ug vs 2 ug |
| Logrank Test | | Logrank Test | |
| Chi square | 6.352 | Chi square | 3.282 |
| df | 1 | df | 1 |
| P value | 0.0207 | P value | 0.0701 |
| P value summary | * | P value summary | ns |
| Are the survival curves different? | yes | Are the survival curves different? | no |

*Fig. 22*

SEQUENCE LISTING

```
<160> NUMBER OF SEQ ID NOS: 63

<210> SEQ ID NO 1
<211> LENGTH: 707
<212> TYPE: PRT
<213> ORGANISM: artificial
<220> FEATURE:
<223> OTHER INFORMATION: Fusion protein.

<400> SEQUENCE: 1

Met Gly Trp Ser Trp Val Met His Leu Ser Pro Val Ser Asn Cys Gly
1               5                   10                  15

Val His Ser Gln Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Ala Trp Val Arg Gln Met Pro Gly Lys Gly Leu
    50                  55                  60

Glu Tyr Met Gly Leu Ile Tyr Pro Gly Asp Ser Asp Thr Lys Tyr Ser
65                  70                  75                  80

Pro Ser Phe Gln Gly Gln Val Thr Ile Ser Val Asp Lys Ser Val Ser
                85                  90                  95

Thr Ala Tyr Leu Gln Trp Ser Ser Leu Lys Pro Ser Asp Ser Ala Val
            100                 105                 110

Tyr Phe Cys Ala Arg His Asp Val Gly Tyr Cys Thr Asp Arg Thr Cys
        115                 120                 125

Ala Lys Trp Pro Glu Tyr Phe Gln His Trp Gly Gln Gly Thr Leu Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Thr Cys Asn Val Asn His Lys Pro Ser Asn Thr
225                 230                 235                 240

Lys Val Asp Lys Arg Val Glu Leu Lys Thr Pro Leu Gly Asp Thr Thr
                245                 250                 255

His Thr Cys Pro Arg Cys Pro Glu Pro Lys Ser Cys Asp Thr Pro Pro
            260                 265                 270

Pro Cys Pro Arg Cys Pro Glu Pro Lys Ser Cys Asp Thr Pro Pro Pro
        275                 280                 285

Cys Pro Arg Cys Pro Glu Pro Lys Ser Cys Asp Thr Pro Pro Pro Cys
    290                 295                 300
```

```
Pro Arg Cys Pro Ala Pro Glu Leu Leu Gly Gly Pro Ser Val Phe Leu
305                 310                 315                 320

Phe Pro Pro Lys Pro Lys Asp Thr Leu Met Ile Ser Arg Thr Pro Glu
            325                 330                 335

Val Thr Cys Val Val Val Asp Val Ser His Glu Asp Pro Glu Val Gln
            340                 345                 350

Phe Lys Trp Tyr Val Asp Gly Val Glu Val His Asn Ala Lys Thr Lys
            355                 360                 365

Leu Arg Glu Glu Gln Tyr Asn Ser Thr Phe Arg Val Val Ser Val Leu
        370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Pro Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Glu Glu Met Thr Lys Asn Gln Val Ser Leu Thr Cys Leu Val Lys
            435                 440                 445

Gly Phe Tyr Pro Ser Asp Ile Ala Val Glu Trp Glu Ser Asn Gly Gln
450                 455                 460

Pro Glu Asn Asn Tyr Asn Thr Thr Pro Pro Met Leu Asp Ser Asp Gly
465                 470                 475                 480

Ser Phe Phe Leu Tyr Ser Lys Leu Thr Val Asp Lys Ser Arg Trp Gln
                485                 490                 495

Gln Gly Asn Ile Phe Ser Cys Ser Val Met His Glu Ala Leu His Asn
                500                 505                 510

His Tyr Thr Gln Lys Ser Leu Ser Leu Ser Pro Gly Lys Ser Gly Gly
            515                 520                 525

Gly Gly Ser Gly Gly Gly Ser Gly Gly Gly Ser Cys Asp Leu
            530                 535                 540

Pro Gln Thr His Asn Leu Arg Asn Lys Arg Ala Leu Thr Leu Leu Val
545                 550                 555                 560

Gln Met Arg Arg Leu Ser Pro Leu Ser Cys Leu Lys Asp Arg Lys Asp
                565                 570                 575

Phe Gly Phe Pro Gln Glu Lys Val Asp Ala Gln Gln Ile Lys Lys Ala
            580                 585                 590

Gln Ala Ile Pro Val Leu Ser Glu Leu Thr Gln Gln Ile Leu Asn Ile
            595                 600                 605

Phe Thr Ser Lys Asp Ser Ser Ala Ala Trp Asn Ala Thr Leu Leu Asp
            610                 615                 620

Ser Phe Cys Asn Asp Leu His Gln Gln Leu Asn Asp Leu Gln Gly Cys
625                 630                 635                 640

Leu Met Gln Gln Val Gly Val Gln Glu Phe Pro Leu Thr Gln Glu Asp
                645                 650                 655

Ala Leu Leu Ala Val Arg Lys Tyr Phe His Arg Ile Thr Val Tyr Leu
            660                 665                 670

Arg Glu Lys Lys His Ser Pro Cys Ala Trp Glu Val Val Arg Ala Glu
            675                 680                 685

Val Trp Arg Ala Leu Ser Ser Ser Ala Asn Val Leu Gly Arg Leu Arg
            690                 695                 700

Glu Glu Lys
705
```

<210> SEQ ID NO 2
<211> LENGTH: 233
<212> TYPE: PRT
<213> ORGANISM: artificial
<220> FEATURE:
<223> OTHER INFORMATION: Fusion protein.

<400> SEQUENCE: 2

```
Met Glu Trp Ser Cys Val Met Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 3
<211> LENGTH: 558
<212> TYPE: DNA
<213> ORGANISM: Artificial
<220> FEATURE:
<223> OTHER INFORMATION: Nucleic acid encoding fusion protein.

<400> SEQUENCE: 3

```
atgaagttgc ctgttaggct gttggtgctg atgttctgga ttcctgcttc cagcagtcaa      60
attgttctct cccagtctcc agcaatcctg tctgcatctc caggggagaa ggtcacaatg     120
acttgcaggg ccagctcaag tgtaagttac atccactggt tccagcagaa gccaggatcc     180
tcccccaaac cctggattta tgccacatcc aactgggctt ctggagtccc tgttcgcttc     240
agtggcagtg ggtctgggac ttcttactct ctcacaatca gcagagtgga ggctgaagat     300
gctgccactt attactgcca gcagtggact agtaacccac ccacgttcgg agggggacc     360 aagctggaaa tcaaacgtaa gtcgactttc tcatcttttt ttatgtgtaa gacacaggtt     420
```

```
ttcatgttag gagttaaagt cagttcagaa aatcttgaga aaatggagag ggctcattat    480
cagttgacgt ggcatacagt gtcagatttt ctgtttatca agctagtgag attaggggca    540
aaaagaggct ttagttga                                                  558

<210> SEQ ID NO 4
<211> LENGTH: 185
<212> TYPE: PRT
<213> ORGANISM: Artificial
<220> FEATURE:
<223> OTHER INFORMATION: Fusion protein.

<400> SEQUENCE: 4

Met Lys Leu Pro Val Arg Leu Leu Val Leu Met Phe Trp Ile Pro Ala
1               5                   10                  15

Ser Ser Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Lys Ser
        115                 120                 125

Thr Phe Ser Ser Phe Phe Met Cys Lys Thr Gln Val Phe Met Leu Gly
    130                 135                 140

Val Lys Val Ser Ser Glu Asn Leu Glu Lys Met Glu Arg Ala His Tyr
145                 150                 155                 160

Gln Leu Thr Trp His Thr Val Ser Asp Phe Leu Phe Ile Lys Leu Val
                165                 170                 175

Arg Leu Gly Ala Lys Arg Gly Phe Ser
            180                 185

<210> SEQ ID NO 5
<211> LENGTH: 2254
<212> TYPE: DNA
<213> ORGANISM: Artificial
<220> FEATURE:
<223> OTHER INFORMATION: Nucleic acid encoding fusion protein.

<400> SEQUENCE: 5
atgtacttgg gactgaactg tgtaatcata gttttttctct taaaaggtgt ccagagtcag    60
gtacaactgc agcagcctgg ggctgagctg gtgaagcctg ggcctcagt gaagatgtcc    120 tgcaaggctt ctggctacac atttaccagt tacaatatgc actgggtaaa acagacacct    180
ggtcggggcc tggaatggat tggagctatt tatcccggaa atggtgatac ttcctacaat    240
cagaagttca aggcaaggc cacattgact gcagacaaat cctccagcac agcctacatg    300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcgccct gctccaggag cacctctggg    480
ggcacagcgg ccctgggctg cctggtcaag gactacttcc ccgaaccggt gacggtgtcg    540
```

-continued

```
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacacctgca acgtgaatca caagcccagc aacaccaagg tggacaagag agttggtgag      720
aggccagcgc agggagggag ggtgtctgct ggaagccagg ctcagccctc ctgcctggac      780
gcatcccggc tgtgcagtcc cagcccaggg caccaaggca ggccccgtct gactcctcac      840
ccggaggcct ctgcccgccc cactcatgct caggagaggg tcttctggc ttttccacc       900
aggctccggg caggcacagg ctggatgccc ctaccccagg cccttcacac acaggggcag      960
gtgctgcgct cagagctgcc aagagccata tccaggagga ccctgcccct gaccgagctc     1020
aaaaccccac ttggtgacac aactcacaca tgcccacggt gcccagagcc caaatcttgt     1080
gacacacctc ccccgtgccc aaggtgccca gagcccaaat cttgtgacac acctcccccg     1140
tgcccaaggt gcccagagcc caaatcttgt gacacacctc ccccgtgccc aaggtgccca     1200
tgatttcccg gacccctgag gtcacgtgcg tggtggtgga cgtgagccac gaagaccccg     1260
aggtccagtt caagtggtac gtggacggcg tggaggtgca taatgccaag acaaagctgc     1320
gggaggagca gtacaacagc acgttccgtg tggtcagcgt cctcaccgtc ctgcaccagg     1380
actggctgaa cggcaaggag tacaagtgca aggtctccaa caaagccctc ccagccccca     1440
tcgagaaacc atctccaaag ccaaaatgac caagaaccag gtcagcctga cctgcctggt     1500
caaaggcttc taccccagcg acatcgccgt ggagtgggag agcaatgggc agccggagaa     1560
caactacaac accacgcctc ccatgctgga ctccgacggc tccttcttcc tctacagcaa     1620
gctcaccgtg gacaagagca ggtggcagca ggggaacatc ttctcatgct ccgtgatgca     1680
tgaggctctg cacaaccact acacgcagaa gagcctctcc ctgtctccgg gtaaatctgg     1740
tggcggtgga tcctgtgacc tgcctcagac tcataaccte aggaacaaga gagccttgac     1800
actcctggta caaatgagga gactctcccc tctctcctgc ctgaaggaca ggaaggactt     1860
tggattcccg caggagaagg tggatgccca gcagatcaag aaggctcaag ccatccctgt     1920
cctgagtgag ctgacccagc agatcctgaa catcttcaca tcaaaggact catctgctgc     1980
ttggaatgca accctcctag actcattctg caatgacctc caccagcagc tcaatgacct     2040
gcaaggttgt ctgatgcagc aggtgggggt gcaggaattt cccctgaccc aggaagatgc     2100
cctgctggct gtgaggaaat acttccacag gatcactgtg tacctgagag agaagaaaca     2160
cagcccctgt gcctgggagg tggtcagagc agaagtctgg agagccctgt cttcctctgc     2220
caatgtgctg ggaagactga gagaagagaa atga                                2254
```

<210> SEQ ID NO 6
<211> LENGTH: 751
<212> TYPE: PRT
<213> ORGANISM: Artificial
<220> FEATURE:
<223> OTHER INFORMATION: Fusion protein.

<400> SEQUENCE: 6

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
```

```
                50                  55                  60
Glu Trp Ile Gly Ala Ile Tyr Pro Gly Asn Gly Asp Thr Ser Tyr Asn
 65                  70                  75                  80
Gln Lys Phe Lys Gly Lys Ala Thr Leu Thr Ala Asp Lys Ser Ser Ser
                     85                  90                  95
Thr Ala Tyr Met Gln Leu Ser Ser Leu Thr Ser Glu Asp Ser Ala Val
                100                 105                 110
Tyr Tyr Cys Ala Arg Ser Thr Tyr Tyr Gly Gly Asp Trp Tyr Phe Asn
                115                 120                 125
Val Trp Gly Ala Gly Thr Thr Val Thr Val Ser Ala Ala Ser Thr Lys
130                 135                 140
Gly Pro Ser Val Phe Pro Leu Ala Pro Cys Ser Arg Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
                195                 200                 205
Val Thr Val Pro Ser Ser Ser Leu Gly Thr Gln Thr Tyr Thr Cys Asn
                210                 215                 220
Val Asn His Lys Pro Ser Asn Thr Lys Val Asp Lys Arg Val Gly Glu
225                 230                 235                 240
Arg Pro Ala Gln Gly Gly Arg Val Ser Ala Gly Ser Gln Ala Gln Pro
                245                 250                 255
Ser Cys Leu Asp Ala Ser Arg Leu Cys Ser Pro Ser Pro Gly His Gln
                260                 265                 270
Gly Arg Pro Arg Leu Thr Pro His Pro Glu Ala Ser Ala Arg Pro Thr
                275                 280                 285
His Ala Gln Gly Glu Gly Leu Leu Ala Phe Ser Thr Arg Leu Arg Ala
                290                 295                 300
Gly Thr Gly Trp Met Pro Leu Pro Gln Ala Leu His Thr Gln Gly Gln
305                 310                 315                 320
Val Leu Arg Ser Glu Leu Pro Arg Ala Ile Ser Arg Arg Thr Leu Pro
                325                 330                 335
Leu Thr Glu Leu Lys Thr Pro Leu Gly Asp Thr Thr His Thr Cys Pro
                340                 345                 350
Arg Cys Pro Glu Pro Lys Ser Cys Asp Thr Pro Pro Pro Cys Pro Arg
                355                 360                 365
Cys Pro Glu Pro Lys Ser Cys Asp Thr Pro Pro Pro Cys Pro Arg Cys
                370                 375                 380
Pro Glu Pro Lys Ser Cys Asp Thr Pro Pro Pro Cys Pro Arg Cys Pro
385                 390                 395                 400
Met Ile Ser Arg Thr Pro Glu Val Thr Cys Val Val Val Asp Val Ser
                405                 410                 415
His Glu Asp Pro Glu Val Gln Phe Lys Trp Tyr Val Asp Gly Val Glu
                420                 425                 430
Val His Asn Ala Lys Thr Lys Leu Arg Glu Glu Gln Tyr Asn Ser Thr
                435                 440                 445
Phe Arg Val Val Ser Val Leu Thr Val Leu His Gln Asp Trp Leu Asn
                450                 455                 460
Gly Lys Glu Tyr Lys Cys Lys Val Ser Asn Lys Ala Leu Pro Ala Pro
465                 470                 475                 480
```

Ile Glu Lys Thr Ile Ser Lys Ala Lys Met Thr Lys Asn Gln Val Ser
            485                 490                 495
Leu Thr Cys Leu Val Lys Gly Phe Tyr Pro Ser Asp Ile Ala Val Glu
        500                 505                 510
Trp Glu Ser Asn Gly Gln Pro Glu Asn Asn Tyr Asn Thr Thr Pro Pro
    515                 520                 525
Met Leu Asp Ser Asp Gly Ser Phe Phe Leu Tyr Ser Lys Leu Thr Val
530                 535                 540
Asp Lys Ser Arg Trp Gln Gln Gly Asn Ile Phe Ser Cys Ser Val Met
545                 550                 555                 560
His Glu Ala Leu His Asn His Tyr Thr Gln Lys Ser Leu Ser Leu Ser
                565                 570                 575
Pro Gly Lys Ser Gly Gly Gly Gly Ser Cys Asp Leu Pro Gln Thr His
            580                 585                 590
Asn Leu Arg Asn Lys Arg Ala Leu Thr Leu Leu Val Gln Met Arg Arg
        595                 600                 605
Leu Ser Pro Leu Ser Cys Leu Lys Asp Arg Lys Asp Phe Gly Phe Pro
    610                 615                 620
Gln Glu Lys Val Asp Ala Gln Gln Ile Lys Lys Ala Gln Ala Ile Pro
625                 630                 635                 640
Val Leu Ser Glu Leu Thr Gln Gln Ile Leu Asn Ile Phe Thr Ser Lys
                645                 650                 655
Asp Ser Ser Ala Ala Trp Asn Ala Thr Leu Leu Asp Ser Phe Cys Asn
            660                 665                 670
Asp Leu His Gln Gln Leu Asn Asp Leu Gln Gly Cys Leu Met Gln Gln
        675                 680                 685
Val Gly Val Gln Glu Phe Pro Leu Thr Gln Glu Asp Ala Leu Leu Ala
    690                 695                 700
Val Arg Lys Tyr Phe His Arg Ile Thr Val Tyr Leu Arg Glu Lys Lys
705                 710                 715                 720
His Ser Pro Cys Ala Trp Glu Val Val Arg Ala Glu Val Trp Arg Ala
                725                 730                 735
Leu Ser Ser Ala Asn Val Leu Gly Arg Leu Arg Glu Glu Lys
            740                 745                 750

<210> SEQ ID NO 7
<211> LENGTH: 2279
<212> TYPE: DNA
<213> ORGANISM: Artificial
<220> FEATURE:
<223> OTHER INFORMATION: Nucleic acid encoding fusion protein.

<400> SEQUENCE: 7

```
atgtacttgg gactgaactg tgtaatcata gttttctctc taaaaggtgt ccagagtcag    60
gtacaactgc agcagcctgg ggctgagctg gtgaagcctg ggcctcagt gaagatgtcc    120 tgcaaggctt ctggctacac atttaccagt acaatatgc actgggtaaa acagacacct    180
ggtcggggcc tggaatggat tggagctatt tatcccggaa atggtgatac ttcctacaat    240
cagaagttca aggcaaggc cacattgact gcagacaaat cctccagcac agcctacatg    300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcgccct gctccaggag cacctctggg    480
ggcacagcgg ccctgggctg cctggtcaag gactacttcc ccgaaccggt gacggtgtcg    540
```

-continued

```
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacacctgca acgtgaatca caagcccagc aacaccaagg tggacaagag agttggtgag    720
aggccagcgc agggagggag ggtgtctgct ggaagccagg ctcagccctc ctgcctggac    780
gcatcccggc tgtgcagtcc cagcccaggg caccaaggca ggccccgtct gactcctcac    840
ccggaggcct ctgcccgccc cactcatgct caggagagag tcttctggc ttttcccacc    900
aggctccggg caggcacagg ctggatgccc ctaccccagg cccttcacac acaggggcag    960
gtgctgcgct cagagctgcc aagagccata tccaggagga ccctgcccct gaccgagctc   1020
aaaaccccac ttggtgacac aactcacaca tgcccacggt gcccagagcc caaatcttgt   1080
gacacacctc ccccgtgccc aaggtgccca gagcccaaat cttgtgacac acctcccccg   1140
tgcccaaggt gcccagagcc caaatcttgt gacacacctc ccccgtgccc aaggtgccca   1200
tgatttcccg gaccctgag gtcacgtgcg tggtggtgga cgtgagccac gaagacccg    1260
aggtccagtt caagtggtac gtggacggcg tggaggtgca taatgccaag acaaagctgc   1320
gggaggagca gtacaacagc acgttccgtg tggtcagcgt cctcaccgtc ctgcaccagg   1380
actggctgaa cggcaaggag tacaagtgca aggtctccaa caaagccctc ccagccccca   1440
tcgagaaaac catctccaaa gccaaaatga ccaagaacca ggtcagcctg acctgcctgg   1500
tcaaaggctt ctaccccagc gacatcgccg tggagtggga gagcaatggg cagccggaga   1560
acaactacaa caccacgcct cccatgctgg actccgacgg ctccttcttc ctctacagca   1620
agctcaccgt ggacaagagc aggtggcagc aggggaacat cttctcatgc tccgtgatgc   1680
atgaggctct gcacaaccac tacacgcaga agagcctctc cctgtctccg ggtaaagcag   1740
aggccgcagc taaagaggcc gcagccaaag cgggatcctg tgacctgcct cagactcata   1800
acctcaggaa caagagagcc ttgacactcc tggtacaaat gaggagactc tcccctctct   1860
cctgcctgaa ggacaggaag gactttggat tcccgcagga aaggtggat gcccagcaga   1920
tcaagaaggc tcaagccatc cctgtcctga gtgagctgac ccagcagatc ctgaacatct   1980
tcacatcaaa ggactcatct gctgcttgga atgcaaccct cctagactca ttctgcaatg   2040
acctccacca gcagctcaat gacctgcaag gttgtctgat gcagcaggtg ggggtgcagg   2100
aatttccccct gacccaggaa gatgcccctgc tggctgtgag gaaatacttc cacaggatca   2160
ctgtgtacct gagagagaag aaacacagcc cctgtgcctg ggaggtggtc agagcagaag   2220
tctggagagc cctgtcttcc tctgccaatg tgctgggaag actgagagaa gagaaatga   2279
```

<210> SEQ ID NO 8
<211> LENGTH: 759
<212> TYPE: PRT
<213> ORGANISM: Artificial
<220> FEATURE:
<223> OTHER INFORMATION: Fusion protein.

<400> SEQUENCE: 8

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu

```
            50                  55                  60
Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Thr Cys Asn
            210                 215                 220

Val Asn His Lys Pro Ser Asn Thr Lys Val Asp Lys Arg Val Gly Glu
225                 230                 235                 240

Arg Pro Ala Gln Gly Gly Arg Val Ser Ala Gly Ser Gln Ala Gln Pro
                245                 250                 255

Ser Cys Leu Asp Ala Ser Arg Leu Cys Ser Pro Ser Pro Gly His Gln
            260                 265                 270

Gly Arg Pro Arg Leu Thr Pro His Pro Glu Ala Ser Ala Arg Pro Thr
            275                 280                 285

His Ala Gln Gly Glu Gly Leu Leu Ala Phe Ser Thr Arg Leu Arg Ala
            290                 295                 300

Gly Thr Gly Trp Met Pro Leu Pro Gln Ala Leu His Thr Gln Gly Gln
305                 310                 315                 320

Val Leu Arg Ser Glu Leu Pro Arg Ala Ile Ser Arg Arg Thr Leu Pro
                325                 330                 335

Leu Thr Glu Leu Lys Thr Pro Leu Gly Asp Thr Thr His Thr Cys Pro
            340                 345                 350

Arg Cys Pro Glu Pro Lys Ser Cys Asp Thr Pro Pro Cys Pro Arg
            355                 360                 365

Cys Pro Glu Pro Lys Ser Cys Asp Thr Pro Pro Cys Pro Arg Cys
            370                 375                 380

Pro Glu Pro Lys Ser Cys Asp Thr Pro Pro Cys Pro Arg Cys Pro
385                 390                 395                 400

Met Ile Ser Arg Thr Pro Glu Val Thr Cys Val Val Asp Val Ser
                405                 410                 415

His Glu Asp Pro Glu Val Gln Phe Lys Trp Tyr Val Asp Gly Val Glu
            420                 425                 430

Val His Asn Ala Lys Thr Lys Leu Arg Glu Glu Gln Tyr Asn Ser Thr
            435                 440                 445

Phe Arg Val Val Ser Val Leu Thr Val Leu His Gln Asp Trp Leu Asn
            450                 455                 460

Gly Lys Glu Tyr Lys Cys Lys Val Ser Asn Lys Ala Leu Pro Ala Pro
465                 470                 475                 480
```

```
Ile Glu Lys Thr Ile Ser Lys Ala Lys Met Thr Lys Asn Gln Val Ser
                485                 490                 495
Leu Thr Cys Leu Val Lys Gly Phe Tyr Pro Ser Asp Ile Ala Val Glu
            500                 505                 510
Trp Glu Ser Asn Gly Gln Pro Glu Asn Asn Tyr Asn Thr Thr Pro Pro
        515                 520                 525
Met Leu Asp Ser Asp Gly Ser Phe Phe Leu Tyr Ser Lys Leu Thr Val
    530                 535                 540
Asp Lys Ser Arg Trp Gln Gln Gly Asn Ile Phe Ser Cys Ser Val Met
545                 550                 555                 560
His Glu Ala Leu His Asn His Tyr Thr Gln Lys Ser Leu Ser Leu Ser
                565                 570                 575
Pro Gly Lys Ala Glu Ala Ala Lys Glu Ala Ala Lys Ala Gly
            580                 585                 590
Ser Cys Asp Leu Pro Gln Thr His Asn Leu Arg Asn Lys Arg Ala Leu
        595                 600                 605
Thr Leu Leu Val Gln Met Arg Arg Leu Ser Pro Leu Ser Cys Leu Lys
    610                 615                 620
Asp Arg Lys Asp Phe Gly Phe Pro Gln Glu Lys Val Asp Ala Gln Gln
625                 630                 635                 640
Ile Lys Lys Ala Gln Ala Ile Pro Val Leu Ser Glu Leu Thr Gln Gln
                645                 650                 655
Ile Leu Asn Ile Phe Thr Ser Lys Asp Ser Ser Ala Ala Trp Asn Ala
            660                 665                 670
Thr Leu Leu Asp Ser Phe Cys Asn Asp Leu His Gln Gln Leu Asn Asp
        675                 680                 685
Leu Gln Gly Cys Leu Met Gln Gln Val Gly Val Gln Glu Phe Pro Leu
    690                 695                 700
Thr Gln Glu Asp Ala Leu Leu Ala Val Arg Lys Tyr Phe His Arg Ile
705                 710                 715                 720
Thr Val Tyr Leu Arg Glu Lys Lys His Ser Pro Cys Ala Trp Glu Val
                725                 730                 735
Val Arg Ala Glu Val Trp Arg Ala Leu Ser Ser Ser Ala Asn Val Leu
            740                 745                 750
Gly Arg Leu Arg Glu Glu Lys
        755

<210> SEQ ID NO 9
<211> LENGTH: 2251
<212> TYPE: DNA
<213> ORGANISM: Artificial
<220> FEATURE:
<223> OTHER INFORMATION: Nucleic acid encoding fusion protein.

<400> SEQUENCE: 9
atgtacttgg gactgaactg tgtaatcata gttttttctct taaaaggtgt ccagagtcag    60
gtacaactgc agcagcctgg ggctgagctg gtgaagcctg ggcctcagt gaagatgtcc    120 tgcaaggctt ctggctacac atttaccagt tacaatatgc actgggtaaa acagacacct    180
ggtcggggcc tggaatggat tggagctatt tatcccggaa atggtgatac ttcctacaat    240
cagaagttca aggcaaggc cacattgact gcagacaaat cctccagcac agcctacatg    300
cagctcagca gcctgacatc tgaggactct gcggtctatt actgtgcaag atcgacttac    360
tacggcggtg actggtactt caatgtctgg ggcgcaggga ccacggtcac cgtctctgca    420
```

```
gctagcacca agggcccatc ggtcttcccc ctggcgccct gctccaggag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacacctgca acgtgaatca caagcccagc aacaccaagg tggacaagag agttggtgag      720
aggccagcgc agggagggag ggtgtctgct ggaagccagg ctcagccctc ctgcctggac      780
gcatcccggc tgtgcagtcc cagcccaggg caccaaggca ggccccgtct gactcctcac      840
ccggaggcct ctgcccgccc cactcatgct caggagagg gtcttctggc tttttccacc      900
aggctccggg caggcacagg ctggatgccc ctaccccagg cccttcacac acaggggcag      960
gtgctgcgct cagagctgcc aagagccata tccaggagga ccctgcccct gaccgagctc     1020
aaaaccccac ttggtgacac aactcacaca tgcccacggt gcccagagcc caaatcttgt     1080
gacacacctc ccccgtgccc aaggtgccca gagcccaaat cttgtgacac acctcccccg     1140
tgcccaaggt gcccagagcc caaatcttgt gacacacctc ccccgtgccc aaggtgccca     1200
tgatttcccg gaccctgag gtcacgtgcg tggtggtgga cgtgagccac gaagaccccg     1260
aggtccagtt caagtggtac gtggacggcg tggaggtgca taatgccaag acaaagctgc     1320
gggaggagca gtacaacagc acgttccgtg tggtcagcgt cctcaccgtc ctgcaccagg     1380
actggctgaa cggcaaggag tacaagtgca aggtctccaa caaagccctc ccagccccca     1440
tcgagaaacc atctccaaag ccaaaatgac caagaaccag gtcagcctga cctgcctggt     1500
caaaggcttc taccccagcg acatcgccgt ggagtgggag agcaatgggc agccggagaa     1560
caactacaac accacgcctc ccatgctgga ctccgacggc tccttcttcc tctacagcaa     1620
gctcaccgtg gacaagagca ggtggcagca ggggaacatc ttctcatgct ccgtgatgca     1680
tgaggctctg cacaaccact acacgcagaa gagcctctcc ctgtctccgg gtaaatctgg     1740
tggcggtgga tcctgtgatc tgcctcaaac ccacagcctg ggtagcagga ggaccttgat     1800
gctcctggca cagatgagga gaatctctct tttctcctgc ttgaaggaca gacatgactt     1860
tggatttccc caggaggagt ttggcaacca gttccaaaag gctgaaacca tccctgtcct     1920
ccatgagatg atccagcaga tcttcaatct cttcagcaca aaggactcat ctgctgcttg     1980
ggatgagacc ctcctagaca aattctacac tgaactctac cagcagctga atgacctgga     2040
agcctgtgtg atacaggggg tgggggtgac agagactccc ctgatgaagg aggactccat     2100
tctggctgtg aggaaatact tccaaagaat cactctctat ctgaaagaga gaaatacag     2160
cccttgtgcc tgggaggttg tcagagcaga aatcatgaga tctttttctt tgtcaacaaa     2220
cttgcaagaa agtttaagaa gtaaggaatg a                                    2251
```

<210> SEQ ID NO 10
<211> LENGTH: 750
<212> TYPE: PRT
<213> ORGANISM: Artificial
<220> FEATURE:
<223> OTHER INFORMATION: Fusion protein.

<400> SEQUENCE: 10

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe

```
                35                  40                  45
Thr Ser Tyr Asn Met His Trp Val Lys Gln Thr Pro Gly Arg Gly Leu
 50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
                115                 120                 125

Val Trp Gly Ala Gly Thr Thr Val Thr Val Ser Ala Ala Ser Thr Lys
                130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Leu Gly Thr Gln Thr Tyr Thr Cys Asn
                210                 215                 220

Val Asn His Lys Pro Ser Asn Thr Lys Val Asp Lys Arg Val Glu
225                 230                 235                 240

Arg Pro Ala Gln Gly Gly Arg Val Ser Ala Gly Ser Gln Ala Gln Pro
                245                 250                 255

Ser Cys Leu Asp Ala Ser Arg Leu Cys Ser Pro Ser Pro Gly His Gln
                260                 265                 270

Gly Arg Pro Arg Leu Thr Pro His Pro Glu Ala Ser Ala Arg Pro Thr
                275                 280                 285

His Ala Gln Gly Glu Gly Leu Leu Ala Phe Ser Thr Arg Leu Arg Ala
                290                 295                 300

Gly Thr Gly Trp Met Pro Leu Pro Gln Ala Leu His Thr Gln Gly Gln
305                 310                 315                 320

Val Leu Arg Ser Glu Leu Pro Arg Ala Ile Ser Arg Arg Thr Leu Pro
                325                 330                 335

Leu Thr Glu Leu Lys Thr Pro Leu Gly Asp Thr Thr His Thr Cys Pro
                340                 345                 350

Arg Cys Pro Glu Pro Lys Ser Cys Asp Thr Pro Pro Cys Pro Arg
                355                 360                 365

Cys Pro Glu Pro Lys Ser Cys Asp Thr Pro Pro Cys Pro Arg Cys
                370                 375                 380

Pro Glu Pro Lys Ser Cys Asp Thr Pro Pro Cys Pro Arg Cys Pro
385                 390                 395                 400

Met Ile Ser Arg Thr Pro Glu Val Thr Cys Val Val Asp Val Ser
                405                 410                 415

His Glu Asp Pro Glu Val Gln Phe Lys Trp Tyr Val Asp Gly Val Glu
                420                 425                 430

Val His Asn Ala Lys Thr Lys Leu Arg Glu Glu Gln Tyr Asn Ser Thr
                435                 440                 445

Phe Arg Val Val Ser Val Leu Thr Val Leu His Gln Asp Trp Leu Asn
450                 455                 460
```

```
Gly Lys Glu Tyr Lys Cys Lys Val Ser Asn Lys Ala Leu Pro Ala Pro
465                 470                 475                 480

Ile Glu Lys Thr Ile Ser Lys Ala Lys Met Thr Lys Asn Gln Val Ser
            485                 490                 495

Leu Thr Cys Leu Val Lys Gly Phe Tyr Pro Ser Asp Ile Ala Val Glu
        500                 505                 510

Trp Glu Ser Asn Gly Gln Pro Glu Asn Asn Tyr Asn Thr Thr Pro Pro
    515                 520                 525

Met Leu Asp Ser Asp Gly Ser Phe Phe Leu Tyr Ser Lys Leu Thr Val
530                 535                 540

Asp Lys Ser Arg Trp Gln Gln Gly Asn Ile Phe Ser Cys Ser Val Met
545                 550                 555                 560

His Glu Ala Leu His Asn His Tyr Thr Gln Lys Ser Leu Ser Leu Ser
            565                 570                 575

Pro Gly Lys Ser Gly Gly Gly Ser Cys Asp Leu Pro Gln Thr His
        580                 585                 590

Ser Leu Gly Ser Arg Arg Thr Leu Met Leu Leu Ala Gln Met Arg Arg
    595                 600                 605

Ile Ser Leu Phe Ser Cys Leu Lys Asp Arg His Asp Phe Gly Phe Pro
610                 615                 620

Gln Glu Glu Phe Gly Asn Gln Phe Gln Lys Ala Glu Thr Ile Pro Val
625                 630                 635                 640

Leu His Glu Met Ile Gln Gln Ile Phe Asn Leu Phe Ser Thr Lys Asp
            645                 650                 655

Ser Ser Ala Ala Trp Asp Glu Thr Leu Leu Asp Lys Phe Tyr Thr Glu
        660                 665                 670

Leu Tyr Gln Gln Leu Asn Asp Leu Glu Ala Cys Val Ile Gln Gly Val
    675                 680                 685

Gly Val Thr Glu Thr Pro Leu Met Lys Glu Asp Ser Ile Leu Ala Val
690                 695                 700

Arg Lys Tyr Phe Gln Arg Ile Thr Leu Tyr Leu Lys Glu Lys Lys Tyr
705                 710                 715                 720

Ser Pro Cys Ala Trp Glu Val Val Arg Ala Glu Ile Met Arg Ser Phe
            725                 730                 735

Ser Leu Ser Thr Asn Leu Gln Glu Ser Leu Arg Ser Lys Glu
        740                 745                 750

<210> SEQ ID NO 11
<211> LENGTH: 2252
<212> TYPE: DNA
<213> ORGANISM: Artificial
<220> FEATURE:
<223> OTHER INFORMATION: Nucleic acid encoding fusion protein.

<400> SEQUENCE: 11
atgtacttgg gactgaactg tgtaatcata gttttctct taaaaggtgt ccagagtcag      60
gtacaactgc agcagcctgg ggctgagctg gtgaagcctg ggcctcagt gaagatgtcc     120 tgcaaggctt ctggctacac atttaccagt tacaatatgc actgggtaaa acagacacct     180
ggtcggggcc tggaatggat tggagctatt tatcccggaa atggtgatac ttcctacaat     240
cagaagttca aggcaaggc acattgact gcagacaaat cctccagcac agcctacatg      300
cagctcagca gcctgacatc tgaggactct gcggtctatt actgtgcaag atcgacttac     360
tacggcggtg actggtactt caatgtctgg ggcgcaggga ccacggtcac cgtctctgca     420
```

```
gctagcacca agggcccatc ggtcttcccc ctggcgccct gctccaggag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacacctgca acgtgaatca caagcccagc aacaccaagg tggacaagag agttggtgag      720
aggccagcgc agggagggag ggtgtctgct ggaagccagg ctcagccctc ctgcctggac      780
gcatcccggc tgtgcagtcc cagcccaggg caccaaggca ggccccgtct gactcctcac      840
ccggaggcct ctgcccgccc cactcatgct caggagagg gtcttctggc ttttccacc       900
aggctccggg caggcacagg ctggatgccc ctaccccagg cccttcacac acaggggcag      960
gtgctgcgct cagagctgcc aagagccata tccaggagga ccctgcccct gaccgagctc     1020
aaaacccac ttggtgacac aactcacaca tgcccacggt gcccagagcc caaatcttgt     1080
gacacacctc ccccgtgccc aaggtgccca gagcccaaat cttgtgacac acctcccccg     1140
tgcccaaggt gcccagagcc caaatcttgt gacacacctc ccccgtgccc aaggtgccca     1200
tgatttcccg gaccctgag gtcacgtgcg tggtggtgga cgtgagccac gaagaccccg      1260
aggtccagtt caagtggtac gtggacggcg tggaggtgca taatgccaag acaaagctgc     1320
gggaggagca gtacaacagc acgttccgtg tggtcagcgt cctcaccgtc ctgcaccagg     1380
actggctgaa cggcaaggag tacaagtgca aggtctccaa caaagccctc ccagccccca     1440
tcgagaaaac catctcccaaa gccaaaatga ccaagaacca ggtcagcctg acctgcctgg     1500
tcaaaggctt ctaccccagc gacatcgccg tggagtggga gagcaatggg cagccggaga     1560
acaactacaa caccacgcct cccatgctgg actccgacgg ctccttcttc ctctacagca     1620
agctcaccgt ggacaagagc aggtggcagc aggggaacat cttctcatgc tccgtgatgc     1680
atgaggctct gcacaaccac tacacgcaga agagcctctc cctgtctccg ggtaaatctg     1740
gtggcggtgg atcctgtgat ctgcctcaaa cccacagcct gggtagcagg aggaccttga     1800
tgctcctggc acagatgagg agaatctctc ttttctcctg cttgaaggac agacatgact     1860
ttggatttcc ccaggaggag tttggcaacc agttccaaaa ggctgaaacc atccctgtcc     1920
tccatgagat gatccagcag atcttcaatc tcttcagcac aaaggactca tctgctgctt     1980
gggatgagac cctcctagac aaattctaca ctgaactcta ccagcagctg aatgacctgg     2040
aagcctgtgt gatacagggg gtgggggtga cagagactcc cctgatgaag gaggactcca     2100
ttctggctgt gaggaaatac ttccaaagaa tcactctcta tctgaaagag aagaaataca     2160
gcccttgtgc ctgggaggtt gtcagagcag aaatcatgag atcttttct ttgtcaacaa     2220
acttgcaaga aagtttaaga agtaaggaat ga                                  2252
```

<210> SEQ ID NO 12
<211> LENGTH: 757
<212> TYPE: PRT
<213> ORGANISM: Artificial
<220> FEATURE:
<223> OTHER INFORMATION: Fusion protein.

<400> SEQUENCE: 12

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe

```
                    35                  40                  45
Thr Ser Tyr Asn Met His Trp Val Lys Gln Thr Pro Gly Arg Gly Leu
                50                  55                  60
Glu Trp Ile Gly Ala Ile Tyr Pro Gly Asn Gly Asp Thr Ser Tyr Asn
 65                  70                  75                  80
Gln Lys Phe Lys Gly Lys Ala Thr Leu Thr Ala Asp Lys Ser Ser Ser
                    85                  90                  95
Thr Ala Tyr Met Gln Leu Ser Ser Leu Thr Ser Glu Asp Ser Ala Val
                100                 105                 110
Tyr Tyr Cys Ala Arg Ser Thr Tyr Tyr Gly Gly Asp Trp Tyr Phe Asn
                115                 120                 125
Val Trp Gly Ala Gly Thr Thr Val Thr Val Ser Ala Ala Ser Thr Lys
                130                 135                 140
Gly Pro Ser Val Phe Pro Leu Ala Pro Cys Ser Arg Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
                195                 200                 205
Val Thr Val Pro Ser Ser Ser Leu Gly Thr Gln Thr Tyr Thr Cys Asn
                210                 215                 220
Val Asn His Lys Pro Ser Asn Thr Lys Val Asp Lys Arg Val Gly Glu
225                 230                 235                 240
Arg Pro Ala Gln Gly Gly Arg Val Ser Ala Gly Ser Gln Ala Gln Pro
                    245                 250                 255
Ser Cys Leu Asp Ala Ser Arg Leu Cys Ser Pro Ser Pro Gly His Gln
                260                 265                 270
Gly Arg Pro Arg Leu Thr Pro His Pro Glu Ala Ser Ala Arg Pro Thr
                275                 280                 285
His Ala Gln Gly Glu Gly Leu Leu Ala Phe Ser Thr Arg Leu Arg Ala
                290                 295                 300
Gly Thr Gly Trp Met Pro Leu Pro Gln Ala Leu His Thr Gln Gly Gln
305                 310                 315                 320
Val Leu Arg Ser Glu Leu Pro Arg Ala Ile Ser Arg Arg Thr Leu Pro
                325                 330                 335
Leu Thr Glu Leu Lys Thr Pro Leu Gly Asp Thr Thr His Thr Cys Pro
                340                 345                 350
Arg Cys Pro Glu Pro Lys Ser Cys Asp Thr Pro Pro Pro Cys Pro Arg
                355                 360                 365
Cys Pro Glu Pro Lys Ser Cys Asp Thr Pro Pro Pro Cys Pro Arg Cys
                370                 375                 380
Pro Glu Pro Lys Ser Cys Asp Thr Pro Pro Pro Cys Pro Arg Cys Pro
385                 390                 395                 400
Met Ile Ser Arg Thr Pro Glu Val Thr Cys Val Val Asp Val Ser
                    405                 410                 415
His Glu Asp Pro Glu Val Gln Phe Lys Trp Tyr Val Asp Gly Val Glu
                420                 425                 430
Val His Asn Ala Lys Thr Lys Leu Arg Glu Glu Gln Tyr Asn Ser Thr
                435                 440                 445
Phe Arg Val Val Ser Val Leu Thr Val Leu His Gln Asp Trp Leu Asn
                450                 455                 460
```

Gly Lys Glu Tyr Lys Cys Lys Val Ser Asn Lys Ala Leu Pro Ala Pro
465                 470                 475                 480

Ile Glu Lys Thr Ile Ser Lys Ala Lys Met Thr Lys Asn Gln Val Ser
                485                 490                 495

Leu Thr Cys Leu Val Lys Gly Phe Tyr Pro Ser Asp Ile Ala Val Glu
            500                 505                 510

Trp Glu Ser Asn Gly Gln Pro Glu Asn Asn Tyr Asn Thr Thr Pro Pro
        515                 520                 525

Met Leu Asp Ser Asp Gly Ser Phe Phe Leu Tyr Ser Lys Leu Thr Val
530                 535                 540

Asp Lys Ser Arg Trp Gln Gln Gly Asn Ile Phe Ser Cys Ser Val Met
545                 550                 555                 560

His Glu Ala Leu His Asn His Tyr Thr Gln Lys Ser Leu Ser Leu Ser
                565                 570                 575

Pro Gly Lys Ser Ala Glu Ala Ala Lys Glu Ala Ala Ala Lys Ala
            580                 585                 590

Cys Asp Leu Pro Gln Thr His Ser Leu Gly Ser Arg Arg Thr Leu Met
            595                 600                 605

Leu Leu Ala Gln Met Arg Arg Ile Ser Leu Phe Ser Cys Leu Lys Asp
    610                 615                 620

Arg His Asp Phe Gly Phe Pro Gln Glu Glu Phe Gly Asn Gln Phe Gln
625                 630                 635                 640

Lys Ala Glu Thr Ile Pro Val Leu His Glu Met Ile Gln Gln Ile Phe
                645                 650                 655

Asn Leu Phe Ser Thr Lys Asp Ser Ser Ala Ala Trp Asp Glu Thr Leu
            660                 665                 670

Leu Asp Lys Phe Tyr Thr Glu Leu Tyr Gln Gln Leu Asn Asp Leu Glu
        675                 680                 685

Ala Cys Val Ile Gln Gly Val Gly Val Thr Glu Thr Pro Leu Met Lys
    690                 695                 700

Glu Asp Ser Ile Leu Ala Val Arg Lys Tyr Phe Gln Arg Ile Thr Leu
705                 710                 715                 720

Tyr Leu Lys Glu Lys Lys Tyr Ser Pro Cys Ala Trp Glu Val Val Arg
                725                 730                 735

Ala Glu Ile Met Arg Ser Phe Ser Leu Ser Thr Asn Leu Gln Glu Ser
            740                 745                 750

Leu Arg Ser Lys Glu
        755

<210> SEQ ID NO 13
<211> LENGTH: 1779
<212> TYPE: DNA
<213> ORGANISM: Artificial
<220> FEATURE:
<223> OTHER INFORMATION: Nucleic acid encoding fusion protein.

<400> SEQUENCE: 13
atgtacttgg gactgaactg tgtaatcata gttttttctct taaaaggtgt ccagagtcag      60
gtacaactgc agcagcctgg ggctgagctg gtgaagcctg ggcctcagt gaagatgtcc      120 tgcaaggctt ctggctacac atttaccagt tacaatatgc actgggtaaa acagacacct      180
ggtcggggcc tggaatggat tgagctatt tatcccggaa atggtgatac ttcctacaat      240
cagaagttca aggcaaggc cacattgact gcagacaaat cctccagcac agcctacatg      300
cagctcagca gcctgacatc tgaggactct gcggtctatt actgtgcaag atcgacttac      360

```
tacggcggtg actggtactt caatgtctgg ggcgcaggga ccacggtcac cgtctctgca    420
gctagccaac caagggccca tcggtcttcc ccctggcacc ctcctccaag agcacctctg    480
ggggcacagc ggccctgggc tgcctggtca aggactactt ccccgaaccg ggagcccaaa    540
tcttgtgaca aaactcacac atgcccaccg tgcccaatga tctcccggac ccctgaggtc    600
acatgcgtgg tggtggacgt gagccacgaa gaccctgagg tcaagttcaa ctggtacgtg    660
gacggcgtgg aggtgcataa tgccaagaca aagccgcggg aggagcagta caacagcacg    720
taccgggtgg tcagcgtcct caccgtcctg caccaggact ggctgaatgg caaggagtac    780
aagtgcaagg tctccaacaa agccctccca gcccccatcg agaaaaccat ctccaaagcc    840
aaaggtggga cccgtggggt gcgagggcca catggacaga ggccggctcg gcccaccctc    900
tgccctgaga gtgaccgctg taccaacctc tgtcctacag gcagccccg agaaccacag     960
gtgtacaccc tgcccccatc ccgggatgag ctgaccaaga accaggtcag cctgacctgc   1020
ctggtcaaag gcttctatcc cagcgacatc gccgtggagt gggagagcaa tgggcagccg   1080
gagaacaact acaagaccac gcctcccgtg ctggactccg acggctcctt cttcctctac   1140
agcaagctca ccgtggacaa gagcaggtgg cagcagggga acgtcttctc atgctccgtg   1200
atgcatgagg ctctgcacaa ccactacacg cagaagagcc tctccctgtc tccgggtaaa   1260
tctggtggcg gtggatcctg tgacctgcct cagactcata acctcaggaa caagagagcc   1320
ttgacactcc tggtacaaat gaggagactc tcccctctct cctgcctgaa ggacaggaag   1380
gactttggat tcccgcagga gaaggtggat gcccagcaga tcaagaaggc tcaagccatc   1440
cctgtcctga gtgagctgac ccagcagatc ctgaacatct tcacatcaaa ggactcatct   1500
gctgcttgga tgcaaccct cctagactca ttctgcaatg acctccacca gcagctcaat    1560
gacctgcaag gttgtctgat gcagcaggtg ggggtgcagg aatttcccct gacccaggaa   1620
gatgccctgc tggctgtgag gaaatacttc cacaggatca ctgtgtacct gagagagaag   1680
aaacacagcc cctgtgcctg ggaggtggtc agagcagaag tctggagagc cctgtcttcc   1740
tctgccaatg tgctgggaag actgagagaa gagaaatga                          1779
```

<210> SEQ ID NO 14
<211> LENGTH: 592
<212> TYPE: PRT
<213> ORGANISM: Artificial
<220> FEATURE:
<223> OTHER INFORMATION: Fusion protein.

<400> SEQUENCE: 14

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110
```

Tyr Tyr Cys Ala Arg Ser Thr Tyr Gly Gly Asp Trp Tyr Phe Asn
        115                 120                 125

Val Trp Gly Ala Gly Thr Thr Val Thr Val Ser Ala Ser Gln Pro
    130                 135                 140

Arg Ala His Arg Ser Ser Pro Trp His Pro Pro Arg Ala Pro Leu
145                 150                 155                 160

Gly Ala Gln Arg Pro Trp Ala Ala Trp Ser Arg Thr Thr Ser Pro Asn
                165                 170                 175

Arg Glu Pro Lys Ser Cys Asp Lys Thr His Thr Cys Pro Pro Cys Pro
                180                 185                 190

Met Ile Ser Arg Thr Pro Glu Val Thr Cys Val Val Asp Val Ser
        195                 200                 205

His Glu Asp Pro Glu Val Lys Phe Asn Trp Tyr Val Asp Gly Val Glu
        210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
                260                 265                 270

Ile Glu Lys Thr Ile Ser Lys Ala Lys Gly Gln Thr Arg Gly Val Arg
                275                 280                 285

Gly Pro His Gly Gln Arg Pro Ala Arg Pro Thr Leu Cys Pro Glu Ser
        290                 295                 300

Asp Arg Cys Thr Asn Leu Cys Pro Thr Gly Gln Pro Arg Glu Pro Gln
305                 310                 315                 320

Val Tyr Thr Leu Pro Pro Ser Arg Asp Glu Leu Thr Lys Asn Gln Val
                325                 330                 335

Ser Leu Thr Cys Leu Val Lys Gly Phe Tyr Pro Ser Asp Ile Ala Val
                340                 345                 350

Glu Trp Glu Ser Asn Gly Gln Pro Glu Asn Asn Tyr Lys Thr Thr Pro
        355                 360                 365

Pro Val Leu Asp Ser Asp Gly Ser Phe Phe Leu Tyr Ser Lys Leu Thr
    370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys Ser Gly Gly Gly Ser Cys Asp Leu Pro Gln Thr
                420                 425                 430

His Asn Leu Arg Asn Lys Arg Ala Leu Thr Leu Leu Val Gln Met Arg
        435                 440                 445

Arg Leu Ser Pro Leu Ser Cys Leu Lys Asp Arg Lys Asp Phe Gly Phe
    450                 455                 460

Pro Gln Glu Lys Val Asp Ala Gln Gln Ile Lys Lys Ala Gln Ala Ile
465                 470                 475                 480

Pro Val Leu Ser Glu Leu Thr Gln Gln Ile Leu Asn Ile Phe Thr Ser
                485                 490                 495

Lys Asp Ser Ser Ala Ala Trp Asn Ala Thr Leu Leu Asp Ser Phe Cys
                500                 505                 510

Asn Asp Leu His Gln Gln Leu Asn Asp Leu Gln Gly Cys Leu Met Gln
        515                 520                 525

Gln Val Gly Val Gln Glu Phe Pro Leu Thr Gln Glu Asp Ala Leu Leu
530                 535                 540

Ala Val Arg Lys Tyr Phe His Arg Ile Thr Val Tyr Leu Arg Glu Lys
545                 550                 555                 560

Lys His Ser Pro Cys Ala Trp Glu Val Val Arg Ala Glu Val Trp Arg
                565                 570                 575

Ala Leu Ser Ser Ser Ala Asn Val Leu Gly Arg Leu Arg Glu Glu Lys
                580                 585                 590

<210> SEQ ID NO 15
<211> LENGTH: 1779
<212> TYPE: DNA
<213> ORGANISM: Artificial
<220> FEATURE:
<223> OTHER INFORMATION: Nucleic acid encoding fusion protein.

<400> SEQUENCE: 15

| | | | | | |
|---|---|---|---|---|---|
| atgtacttgg | gactgaactg | tgtaatcata | gtttttctct | taaaaggtgt | ccagagtcag | 60 |
| gtacaactgc | agcagcctgg | ggctgagctg | gtgaagcctg | ggcctcagt | gaagatgtcc | 120 |
| tgcaaggctt | ctggctacac | atttaccagt | tacaatatgc | actgggtaaa | cagacacct | 180 |
| ggtcgggcc | tggaatggat | tggagctatt | tatcccggaa | atggtgatac | ttcctacaat | 240 |
| cagaagttca | aggcaaggc | cacattgact | gcagacaaat | cctccagcac | agcctacatg | 300 |
| cagctcagca | gcctgacatc | tgaggactct | gcggtctatt | actgtgcaag | atcgacttac | 360 |
| tacggcggtg | actggtactt | caatgtctgg | ggcgcaggga | ccacggtcac | cgtctctgca | 420 |
| gctagccaac | caagggccca | tcggtcttcc | ccctggcacc | ctcctccaag | agcacctctg | 480 |
| ggggcacagc | ggccctgggc | tgcctggtca | aggactactt | ccccgaaccg | ggagcccaaa | 540 |
| tcttgtgaca | aaactcacac | atgcccaccg | tgcccaatga | tctcccggac | ccctgaggtc | 600 |
| acatgcgtgg | tggtggacgt | gagccacgaa | gaccctgagg | tcaagttcaa | ctggtacgtg | 660 |
| gacggcgtgg | aggtgcataa | tgccaagaca | aagccgcggg | aggagcagta | caacagcacg | 720 |
| taccgggtgg | tcagcgtcct | caccgtcctg | caccaggact | ggctgaatgg | caaggagtac | 780 |
| aagtgcaagg | tctccaacaa | agccctccca | gcccccatcg | agaaaaccat | ctccaaagcc | 840 |
| aaaggtggga | cccgtggggt | gcgagggcca | catggacaga | ggccggctcg | gcccaccctc | 900 |
| tgccctgaga | gtgaccgctg | taccaacctc | tgtcctacag | ggcagccccg | agaaccacag | 960 |
| gtgtacaccc | tgcccccatc | ccgggatgag | ctgaccaaga | accaggtcag | cctgacctgc | 1020 |
| ctggtcaaag | gcttctatcc | cagcgacatc | gccgtggagt | gggagagcaa | tgggcagccg | 1080 |
| gagaacaact | acaagaccac | gcctcccgtg | ctggactccg | acggctcctt | cttcctctac | 1140 |
| agcaagctca | ccgtggacaa | gagcaggtgg | cagcagggga | acgtcttctc | atgctccgtg | 1200 |
| atgcatgagg | ctctgcacaa | ccactacacg | cagaagagcc | tctccctgtc | tccgggtaaa | 1260 |
| tctggtggcg | gtggatcctg | tgacctgcct | cagactcata | acctcaggaa | caagagagcc | 1320 |
| ttgacactcc | tggtacaaat | gaggagactc | tcccctctct | cctgcctgaa | ggacaggaag | 1380 |
| gactttggat | tcccgcagga | gaaggtggat | gcccagcaga | tcaagaaggc | tcaagccatc | 1440 |
| cctgtcctga | gtgagctgac | ccagcagatc | ctgaacatct | tcacatcaaa | ggactcatct | 1500 |
| gctgcttgga | atgcaaccct | cctagactca | ttctgcaatg | acctccacca | gcagctcaat | 1560 |
| gacctgcaag | gttgtctgat | gcagcaggtg | ggggtgcagg | aatttccct | gacccaggaa | 1620 |
| gatgccctgc | tggctgtgag | gaaatacttc | cacaggatca | ctgtgtacct | gagagagaag | 1680 |
| aaacacagcc | cctgtgcctg | ggaggtggtc | agagcagaag | tctggagagc | cctgtcttcc | 1740 | tctgccaatg tgctgggaag actgagagaa gagaaatga                                    1779

<210> SEQ ID NO 16
<211> LENGTH: 599
<212> TYPE: PRT
<213> ORGANISM: Artificial
<220> FEATURE:
<223> OTHER INFORMATION: Fusion protein.

<400> SEQUENCE: 16

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Gln Pro
    130                 135                 140

Arg Ala His Arg Ser Ser Pro Trp His Pro Pro Arg Ala Pro Leu
145                 150                 155                 160

Gly Ala Gln Arg Pro Trp Ala Ala Trp Ser Arg Thr Thr Ser Pro Asn
                165                 170                 175

Arg Glu Pro Lys Ser Cys Asp Lys Thr His Thr Cys Pro Pro Cys Pro
            180                 185                 190

Met Ile Ser Arg Thr Pro Glu Val Thr Cys Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gly Thr Arg Gly Val Arg
        275                 280                 285

Gly Pro His Gly Gln Arg Pro Ala Arg Pro Thr Leu Cys Pro Glu Ser
    290                 295                 300

Asp Arg Cys Thr Asn Leu Cys Pro Thr Gly Gln Pro Arg Glu Pro Gln
305                 310                 315                 320

Val Tyr Thr Leu Pro Pro Ser Arg Asp Glu Leu Thr Lys Asn Gln Val
                325                 330                 335

Ser Leu Thr Cys Leu Val Lys Gly Phe Tyr Pro Ser Asp Ile Ala Val
            340                 345                 350

```
Glu Trp Glu Ser Asn Gly Gln Pro Glu Asn Asn Tyr Lys Thr Thr Pro
            355                 360                 365

Pro Val Leu Asp Ser Asp Gly Ser Phe Phe Leu Tyr Ser Lys Leu Thr
    370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys Ser Ala Glu Ala Ala Lys Glu Ala Ala Lys
            420                 425                 430

Ala Cys Asp Leu Pro Gln Thr His Asn Leu Arg Asn Lys Arg Ala Leu
435                 440                 445

Thr Leu Leu Val Gln Met Arg Arg Leu Ser Pro Leu Ser Cys Leu Lys
    450                 455                 460

Asp Arg Lys Asp Phe Gly Phe Pro Gln Glu Lys Val Asp Ala Gln Gln
465                 470                 475                 480

Ile Lys Lys Ala Gln Ala Ile Pro Val Leu Ser Glu Leu Thr Gln Gln
                485                 490                 495

Ile Leu Asn Ile Phe Thr Ser Lys Asp Ser Ser Ala Ala Trp Asn Ala
                500                 505                 510

Thr Leu Leu Asp Ser Phe Cys Asn Asp Leu His Gln Gln Leu Asn Asp
    515                 520                 525

Leu Gln Gly Cys Leu Met Gln Gln Val Gly Val Gln Glu Phe Pro Leu
    530                 535                 540

Thr Gln Glu Asp Ala Leu Leu Ala Val Arg Lys Tyr Phe His Arg Ile
545                 550                 555                 560

Thr Val Tyr Leu Arg Glu Lys Lys His Ser Pro Cys Ala Trp Glu Val
                565                 570                 575

Val Arg Ala Glu Val Trp Arg Ala Leu Ser Ser Ser Ala Asn Val Leu
            580                 585                 590

Gly Arg Leu Arg Glu Glu Lys
            595

<210> SEQ ID NO 17
<211> LENGTH: 1776
<212> TYPE: DNA
<213> ORGANISM: Artificial
<220> FEATURE:
<223> OTHER INFORMATION: Nucleic acid encoding fusion protein.

<400> SEQUENCE: 17
atgtacttgg gactgaactg tgtaatcata gttttctct  taaaggtgt ccagagtcag      60 gtacaactgc agcagcctgg ggctgagctg gtgaagcctg gggcctcagt gaagatgtcc     120
tgcaaggctt ctggctacac atttaccagt tacaatatgc actgggtaaa acagacacct     180
ggtcggggcc tggaatggat tggagctatt tatcccggaa atggtgatac ttcctacaat     240
cagaagttca aaggcaaggc cacattgact gcagacaaat cctccagcac agcctacatg     300
cagctcagca gcctgacatc tgaggactct gcggtctatt actgtgcaag atcgacttac     360
tacggcggtg actggtactt caatgtctgg ggcgcaggga ccacggtcac cgtctctgca     420
gctagccaac caagggccca tcggtcttcc ccctggcacc ctcctccaag agcacctctg     480
ggggcacagc ggccctgggc tgcctggtca aggactactt ccccgaaccg ggagccaaa     540 tcttgtgaca aaactcacac atgcccaccg tgcccaatga tctcccggac ccctgaggtc     600
acatgcgtgg tggtggacgt gagccacgaa gaccctgagg tcaagttcaa ctggtacgtg     660
```

```
gacggcgtgg aggtgcataa tgccaagaca aagccgcggg aggagcagta caacagcacg    720
taccgggtgg tcagcgtcct caccgtcctg caccaggact ggctgaatgg caaggagtac    780
aagtgcaagg tctccaacaa agccctccca gcccccatcg agaaaaccat ctccaaagcc    840
aaaggtggga cccgtggggt gcgagggcca catggacaga ggccggctcg gcccacc ctc    900 tgccctgaga gtgaccgctg taccaacctc tgtcctacag ggcagccccg agaaccacag    960
gtgtacaccc tgcccccatc ccgggatgag ctgaccaaga accaggtcag cctgacctgc   1020
ctggtcaaag gcttctatcc cagcgacatc gccgtggagt gggagagcaa tgggcagccg   1080
gagaacaact acaagaccac gcctcccgtg ctggactccg acggctcctt cttcctctac   1140
agcaagctca ccgtggacaa gagcaggtgg cagcagggga acgtcttctc atgctccgtg   1200
atgcatgagg ctctgcacaa ccactacacg cagaagagcc tctccctgtc tccgggtaaa   1260
tctggtggcg gtggatcctg tgatctgcct caaacccaca gcctgggtag caggaggacc   1320
ttgatgctcc tggcacagat gaggagaatc tctcttttct cctgcttgaa ggacagacat   1380
gactttggat tccccaggag ggagtttggc aaccagttcc aaaaggctga aaccatccct   1440
gtcctccatg agatgatcca gcagatcttc aatctcttca gcacaaagga ctcatctgct   1500
gcttgggatg agaccctcct agacaaattc tacactgaac tctaccagca gctgaatgac   1560
ctggaagcct gtgtgataca gggggtgggg gtgacagaga ctcccctgat gaaggaggac   1620
tccattctgg ctgtgaggaa atacttccaa agaatcactc tctatctgaa agagaagaaa   1680
tacagccctt gtgcctggga ggttgtcaga gcagaaatca tgagatcttt ttctttgtca   1740
acaaacttgc aagaaagttt aagaagtaag gaatga                             1776
```

<210> SEQ ID NO 18
<211> LENGTH: 591
<212> TYPE: PRT
<213> ORGANISM: Artificial
<220> FEATURE:
<223> OTHER INFORMATION: Fusion protein.

<400> SEQUENCE: 18

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Gln Pro
    130                 135                 140

Arg Ala His Arg Ser Ser Pro Trp His Pro Pro Arg Ala Pro Leu
145                 150                 155                 160
```

-continued

```
Gly Ala Gln Arg Pro Trp Ala Ala Trp Ser Arg Thr Thr Ser Pro Asn
                165                 170                 175
Arg Glu Pro Lys Ser Cys Asp Lys Thr His Thr Cys Pro Pro Cys Pro
            180                 185                 190
Met Ile Ser Arg Thr Pro Glu Val Thr Cys Val Val Val Asp Val Ser
        195                 200                 205
His Glu Asp Pro Glu Val Lys Phe Asn Trp Tyr Val Asp Gly Val Glu
    210                 215                 220
Val His Asn Ala Lys Thr Lys Pro Arg Glu Glu Gln Tyr Asn Ser Thr
225                 230                 235                 240
Tyr Arg Val Val Ser Val Leu Thr Val Leu His Gln Asp Trp Leu Asn
                245                 250                 255
Gly Lys Glu Tyr Lys Cys Lys Val Ser Asn Lys Ala Leu Pro Ala Pro
            260                 265                 270
Ile Glu Lys Thr Ile Ser Lys Ala Lys Gly Gln Pro Arg Glu Pro Gln
        275                 280                 285
Gly Pro His Gly Gln Arg Pro Ala Arg Pro Thr Leu Cys Pro Glu Ser
    290                 295                 300
Asp Arg Cys Thr Asn Leu Cys Pro Thr Gly Gln Pro Arg Glu Pro Gln
305                 310                 315                 320
Val Tyr Thr Leu Pro Pro Ser Arg Asp Glu Leu Thr Lys Asn Gln Val
                325                 330                 335
Ser Leu Thr Cys Leu Val Lys Gly Phe Tyr Pro Ser Asp Ile Ala Val
            340                 345                 350
Glu Trp Glu Ser Asn Gly Gln Pro Glu Asn Asn Tyr Lys Thr Thr Pro
        355                 360                 365
Pro Val Leu Asp Ser Asp Gly Ser Phe Phe Leu Tyr Ser Lys Leu Thr
    370                 375                 380
Val Asp Lys Ser Arg Trp Gln Gln Gly Asn Val Phe Ser Cys Ser Val
385                 390                 395                 400
Met His Glu Ala Leu His Asn His Tyr Thr Gln Lys Ser Leu Ser Leu
                405                 410                 415
Ser Pro Gly Lys Ser Gly Gly Gly Ser Cys Asp Leu Pro Gln Thr
            420                 425                 430
His Ser Leu Gly Ser Arg Arg Thr Leu Met Leu Leu Ala Gln Met Arg
    435                 440                 445
Arg Ile Ser Leu Phe Ser Cys Leu Lys Asp Arg His Asp Phe Gly Phe
450                 455                 460
Pro Gln Glu Glu Phe Gly Asn Gln Phe Gln Lys Ala Glu Thr Ile Pro
465                 470                 475                 480
Val Leu His Glu Met Ile Gln Gln Ile Phe Asn Leu Phe Ser Thr Lys
                485                 490                 495
Asp Ser Ser Ala Ala Trp Asp Glu Thr Leu Leu Asp Lys Phe Tyr Thr
            500                 505                 510
Glu Leu Tyr Gln Gln Leu Asn Asp Leu Glu Ala Cys Val Ile Gln Gly
        515                 520                 525
Val Gly Val Thr Glu Thr Pro Leu Met Lys Glu Asp Ser Ile Leu Ala
    530                 535                 540
Val Arg Lys Tyr Phe Gln Arg Ile Thr Leu Tyr Leu Lys Glu Lys Lys
545                 550                 555                 560
Tyr Ser Pro Cys Ala Trp Glu Val Val Arg Ala Glu Ile Met Arg Ser
                565                 570                 575
Phe Ser Leu Ser Thr Asn Leu Gln Glu Ser Leu Arg Ser Lys Glu
```

```
            580                 585                 590

<210> SEQ ID NO 19
<211> LENGTH: 1800
<212> TYPE: PRT
<213> ORGANISM: Artificial
<220> FEATURE:
<223> OTHER INFORMATION: Fusion protein

<400> SEQUENCE: 19

Ala Thr Gly Thr Ala Cys Thr Thr Gly Gly Gly Ala Cys Thr Gly Ala
1               5                   10                  15

Ala Cys Thr Gly Thr Gly Thr Ala Ala Thr Cys Ala Thr Ala Gly Thr
            20                  25                  30

Thr Thr Thr Thr Cys Thr Cys Thr Thr Ala Ala Ala Ala Gly Gly Thr
        35                  40                  45

Gly Thr Cys Cys Ala Gly Ala Gly Thr Cys Ala Gly Gly Thr Ala Cys
    50                  55                  60

Ala Ala Cys Thr Gly Cys Ala Gly Cys Ala Gly Cys Cys Thr Gly Gly
65                  70                  75                  80

Gly Gly Cys Thr Gly Ala Gly Cys Thr Gly Gly Thr Gly Ala Ala Gly
                85                  90                  95

Cys Cys Thr Gly Gly Gly Gly Cys Cys Thr Cys Ala Gly Thr Gly Ala
            100                 105                 110

Ala Gly Ala Thr Gly Thr Cys Cys Thr Gly Cys Ala Ala Gly Gly Cys
        115                 120                 125

Thr Thr Cys Thr Gly Gly Cys Thr Ala Cys Ala Cys Ala Thr Thr Thr
    130                 135                 140

Ala Cys Cys Ala Gly Thr Thr Ala Cys Ala Ala Thr Ala Thr Gly Cys
145                 150                 155                 160

Ala Cys Thr Gly Gly Gly Thr Ala Ala Ala Ala Cys Ala Gly Ala Cys
                165                 170                 175

Ala Cys Cys Thr Gly Gly Thr Cys Gly Gly Gly Gly Cys Cys Thr Gly
            180                 185                 190

Gly Ala Ala Thr Gly Gly Ala Thr Thr Gly Gly Ala Gly Cys Thr Ala
        195                 200                 205

Thr Thr Thr Ala Thr Cys Cys Cys Gly Gly Ala Ala Ala Thr Gly Gly
    210                 215                 220

Thr Gly Ala Thr Ala Cys Thr Thr Cys Cys Thr Ala Cys Ala Ala Thr
225                 230                 235                 240

Cys Ala Gly Ala Ala Gly Thr Thr Cys Ala Ala Ala Gly Gly Cys Ala
                245                 250                 255

Ala Gly Gly Cys Cys Ala Cys Ala Thr Thr Gly Ala Cys Thr Gly Cys
            260                 265                 270

Ala Gly Ala Cys Ala Ala Ala Thr Cys Cys Thr Cys Cys Ala Gly Cys
        275                 280                 285

Ala Cys Ala Gly Cys Cys Thr Ala Cys Ala Thr Gly Cys Ala Gly Cys
    290                 295                 300

Thr Cys Ala Gly Cys Ala Gly Cys Cys Thr Gly Ala Cys Ala Thr Cys
305                 310                 315                 320

Thr Gly Ala Gly Gly Ala Cys Thr Cys Thr Gly Cys Gly Gly Thr Cys
                325                 330                 335

Thr Ala Thr Thr Ala Cys Thr Gly Thr Gly Cys Ala Ala Gly Ala Thr
            340                 345                 350

Cys Gly Ala Cys Thr Thr Ala Cys Thr Ala Cys Gly Gly Cys Gly Gly
```

-continued

```
                    355                 360                 365
Thr Gly Ala Cys Thr Gly Gly Thr Ala Cys Thr Thr Cys Ala Ala Thr
                370                 375                 380
Gly Thr Cys Thr Gly Gly Gly Cys Gly Cys Ala Gly Gly Gly Ala
385                 390                 395                 400
Cys Cys Ala Cys Gly Gly Thr Cys Ala Cys Gly Thr Cys Thr Cys
                405                 410                 415
Thr Gly Cys Ala Gly Cys Thr Ala Gly Cys Cys Ala Cys Cys Ala
                420                 425                 430
Ala Gly Gly Gly Cys Cys Ala Thr Cys Gly Gly Thr Cys Thr Thr
                435                 440                 445
Cys Cys Cys Cys Thr Gly Gly Cys Ala Cys Cys Thr Cys Cys
                450                 455                 460
Thr Cys Cys Ala Ala Gly Ala Gly Cys Ala Cys Cys Thr Cys Thr Gly
465                 470                 475                 480
Gly Gly Gly Gly Cys Ala Cys Ala Gly Cys Gly Gly Cys Cys Thr
                485                 490                 495
Gly Gly Gly Cys Thr Gly Cys Cys Thr Gly Thr Cys Ala Ala Gly
                500                 505                 510
Gly Ala Cys Thr Ala Cys Thr Thr Cys Cys Cys Cys Gly Ala Ala Cys
                515                 520                 525
Cys Gly Gly Gly Ala Gly Cys Cys Ala Ala Thr Cys Thr
                530                 535                 540
Gly Thr Gly Ala Cys Ala Ala Ala Cys Thr Cys Ala Cys Ala Cys
545                 550                 555                 560
Ala Thr Gly Cys Cys Cys Ala Cys Cys Gly Thr Gly Cys Cys Cys Ala
                565                 570                 575
Ala Thr Gly Ala Thr Cys Thr Cys Cys Gly Gly Ala Cys Cys Cys
                580                 585                 590
Cys Thr Gly Ala Gly Gly Thr Cys Ala Cys Ala Thr Gly Cys Gly Thr
                595                 600                 605
Gly Gly Thr Gly Gly Thr Gly Gly Ala Cys Gly Thr Gly Ala Gly Cys
                610                 615                 620
Cys Ala Cys Gly Ala Ala Gly Ala Cys Cys Cys Thr Gly Ala Gly Gly
625                 630                 635                 640
Thr Cys Ala Ala Gly Thr Thr Cys Ala Ala Cys Thr Gly Gly Thr Ala
                645                 650                 655
Cys Gly Thr Gly Gly Ala Cys Gly Gly Cys Gly Thr Gly Gly Ala Gly
                660                 665                 670
Gly Thr Gly Cys Ala Thr Ala Ala Thr Gly Cys Cys Ala Ala Gly Ala
                675                 680                 685
Cys Ala Ala Ala Gly Cys Cys Gly Cys Gly Gly Gly Ala Gly Gly Ala
                690                 695                 700
Gly Cys Ala Gly Thr Ala Cys Ala Ala Cys Ala Gly Cys Ala Cys Gly
705                 710                 715                 720
Thr Ala Cys Cys Gly Gly Gly Thr Gly Gly Thr Cys Ala Gly Cys Gly
                725                 730                 735
Thr Cys Cys Thr Cys Ala Cys Cys Gly Thr Cys Cys Thr Gly Cys Ala
                740                 745                 750
Cys Cys Ala Gly Gly Ala Cys Thr Gly Gly Cys Thr Gly Ala Ala Thr
                755                 760                 765
Gly Gly Cys Ala Ala Gly Gly Ala Gly Thr Ala Cys Ala Ala Gly Thr
                770                 775                 780
```

-continued

Gly Cys Ala Ala Gly Gly Thr Cys Thr Cys Cys Ala Ala Cys Ala Ala
785 790 795 800

Ala Gly Cys Cys Cys Thr Cys Cys Cys Ala Gly Cys Cys Cys Cys Cys
805 810 815

Ala Thr Cys Gly Ala Gly Ala Ala Ala Ala Cys Cys Ala Thr Cys Thr
820 825 830

Cys Cys Ala Ala Ala Gly Cys Cys Ala Ala Ala Gly Gly Thr Gly Gly
835 840 845

Gly Ala Cys Cys Cys Gly Thr Gly Gly Gly Gly Thr Gly Cys Gly Ala
850 855 860

Gly Gly Gly Cys Cys Ala Cys Ala Thr Gly Gly Ala Cys Ala Gly Ala
865 870 875 880

Gly Gly Cys Cys Gly Gly Cys Thr Cys Gly Gly Cys Cys Cys Ala Cys
885 890 895

Cys Cys Thr Cys Thr Gly Cys Cys Cys Thr Gly Ala Gly Ala Gly Thr
900 905 910

Gly Ala Cys Cys Gly Cys Thr Gly Thr Ala Cys Cys Ala Ala Cys Cys
915 920 925

Thr Cys Thr Gly Thr Cys Cys Thr Ala Cys Ala Gly Gly Gly Cys Ala
930 935 940

Gly Cys Cys Cys Cys Gly Ala Gly Ala Ala Cys Cys Ala Cys Ala Gly
945 950 955 960

Gly Thr Gly Thr Ala Cys Ala Cys Cys Cys Thr Gly Cys Cys Cys Cys
965 970 975

Cys Ala Thr Cys Cys Cys Gly Gly Gly Ala Thr Gly Ala Gly Cys Thr
980 985 990

Gly Ala Cys Cys Ala Ala Gly Ala Ala Cys Cys Ala Gly Gly Thr Cys
995 1000 1005

Ala Gly Cys Cys Thr Gly Ala Cys Cys Thr Gly Cys Cys Thr Gly
1010 1015 1020

Gly Thr Cys Ala Ala Ala Gly Gly Cys Thr Thr Cys Thr Ala Thr
1025 1030 1035

Cys Cys Cys Ala Gly Cys Gly Ala Cys Ala Thr Cys Gly Cys Cys
1040 1045 1050

Gly Thr Gly Gly Ala Gly Thr Gly Gly Gly Ala Gly Ala Gly Cys
1055 1060 1065

Ala Ala Thr Gly Gly Gly Cys Ala Gly Cys Cys Gly Gly Ala Gly
1070 1075 1080

Ala Ala Cys Ala Ala Cys Thr Ala Cys Ala Ala Gly Ala Cys Cys
1085 1090 1095

Ala Cys Gly Cys Cys Thr Cys Cys Cys Gly Thr Gly Cys Thr Gly
1100 1105 1110

Gly Ala Cys Thr Cys Cys Gly Ala Cys Gly Gly Cys Thr Cys Cys
1115 1120 1125

Thr Thr Cys Thr Thr Cys Cys Thr Cys Thr Ala Cys Ala Gly Cys
1130 1135 1140

Ala Ala Gly Cys Thr Cys Ala Cys Cys Gly Thr Gly Gly Ala Cys
1145 1150 1155

Ala Ala Gly Ala Gly Cys Ala Gly Gly Thr Gly Gly Cys Ala Gly
1160 1165 1170

Cys Ala Gly Gly Gly Gly Ala Ala Cys Gly Thr Cys Thr Thr Cys
1175 1180 1185

```
Thr Cys Ala Thr Gly Cys Thr Cys Cys Gly Thr Gly Ala Thr Gly
    1190            1195                1200
Cys Ala Thr Gly Ala Gly Gly Cys Thr Cys Thr Gly Cys Ala Cys
    1205            1210                1215
Ala Ala Cys Cys Ala Cys Thr Ala Cys Ala Cys Gly Cys Ala Gly
    1220            1225                1230
Ala Ala Gly Ala Gly Cys Cys Thr Cys Thr Cys Cys Cys Thr Gly
    1235            1240                1245
Thr Cys Thr Cys Cys Gly Gly Gly Thr Ala Ala Ala Gly Cys Ala
    1250            1255                1260
Gly Ala Gly Gly Cys Cys Gly Cys Ala Gly Cys Thr Ala Ala Ala
    1265            1270                1275
Gly Ala Gly Gly Cys Cys Gly Cys Ala Gly Cys Cys Ala Ala Ala
    1280            1285                1290
Gly Cys Gly Gly Gly Ala Thr Cys Cys Thr Gly Thr Gly Ala Thr
    1295            1300                1305
Cys Thr Gly Cys Cys Thr Cys Ala Ala Ala Cys Cys Ala Cys Cys
    1310            1315                1320
Ala Gly Cys Cys Thr Gly Gly Thr Ala Gly Cys Ala Gly Gly Gly
    1325            1330                1335
Ala Gly Gly Ala Cys Cys Thr Thr Gly Ala Thr Gly Cys Thr Cys
    1340            1345                1350
Cys Thr Gly Gly Cys Ala Cys Ala Gly Ala Thr Gly Ala Gly Gly
    1355            1360                1365
Ala Gly Ala Ala Thr Cys Thr Cys Thr Cys Thr Thr Thr Thr Cys
    1370            1375                1380
Thr Cys Cys Thr Gly Cys Thr Gly Ala Ala Gly Gly Ala Gly Cys
    1385            1390                1395
Ala Gly Ala Cys Ala Thr Gly Ala Cys Thr Thr Thr Gly Gly Ala
    1400            1405                1410
Thr Thr Thr Cys Cys Cys Cys Ala Gly Gly Ala Gly Gly Ala Gly
    1415            1420                1425
Thr Thr Thr Gly Gly Cys Ala Ala Cys Cys Ala Gly Thr Thr Cys
    1430            1435                1440
Cys Ala Ala Ala Ala Gly Gly Cys Thr Gly Ala Ala Ala Cys Cys
    1445            1450                1455
Ala Thr Cys Cys Cys Thr Gly Thr Cys Thr Cys Cys Cys Ala Thr
    1460            1465                1470
Gly Ala Gly Ala Thr Gly Ala Thr Cys Cys Ala Gly Cys Ala Gly
    1475            1480                1485
Ala Thr Cys Thr Thr Cys Ala Ala Thr Cys Thr Cys Thr Thr Cys
    1490            1495                1500
Ala Gly Cys Ala Cys Ala Ala Gly Gly Ala Cys Thr Cys Ala Thr
    1505            1510                1515
Thr Cys Thr Gly Cys Thr Gly Cys Thr Thr Gly Gly Ala Thr Thr
    1520            1525                1530
Gly Ala Gly Ala Cys Cys Cys Thr Cys Thr Ala Gly Ala Cys Thr
    1535            1540                1545
Ala Ala Ala Thr Thr Cys Thr Ala Cys Ala Cys Thr Gly Ala Ala
    1550            1555                1560
Cys Thr Cys Thr Ala Cys Cys Ala Gly Cys Ala Gly Cys Thr Gly
    1565            1570                1575
Ala Ala Thr Gly Ala Cys Cys Thr Gly Gly Ala Ala Gly Cys Cys
```

```
                    1580                1585                1590
Thr Gly Thr Gly Thr Gly Ala Thr Ala Cys Ala Gly Gly Gly
        1595                1600                1605
Gly Thr Gly Gly Gly Gly Gly Thr Gly Ala Cys Ala Gly Ala Gly
        1610                1615                1620
Ala Cys Thr Cys Cys Cys Cys Thr Gly Ala Thr Gly Ala Ala Gly
        1625                1630                1635
Gly Ala Gly Gly Ala Cys Thr Cys Cys Ala Thr Thr Cys Thr Gly
        1640                1645                1650
Gly Cys Thr Gly Thr Gly Ala Gly Gly Ala Ala Ala Thr Ala Cys
        1655                1660                1665
Thr Thr Cys Cys Ala Ala Ala Gly Ala Ala Thr Cys Ala Cys Thr
        1670                1675                1680
Cys Thr Cys Thr Ala Thr Cys Thr Gly Ala Ala Ala Gly Ala Gly
        1685                1690                1695
Ala Ala Gly Ala Ala Ala Thr Ala Cys Ala Gly Cys Cys Cys Thr
        1700                1705                1710
Thr Gly Thr Gly Cys Cys Thr Gly Gly Ala Gly Gly Thr Thr
        1715                1720                1725
Gly Thr Cys Ala Gly Ala Gly Cys Ala Gly Ala Ala Ala Thr Cys
        1730                1735                1740
Ala Thr Gly Ala Gly Ala Thr Cys Thr Thr Thr Thr Cys Thr
        1745                1750                1755
Thr Thr Gly Thr Cys Ala Ala Cys Ala Ala Ala Cys Thr Thr Gly
        1760                1765                1770
Cys Ala Ala Gly Ala Ala Ala Gly Thr Thr Ala Ala Gly Ala
        1775                1780                1785
Ala Gly Thr Ala Ala Gly Gly Ala Ala Thr Gly Ala
        1790                1795                1800

<210> SEQ ID NO 20
<211> LENGTH: 599
<212> TYPE: PRT
<213> ORGANISM: Artificial
<220> FEATURE:
<223> OTHER INFORMATION: Fusion protein.

<400> SEQUENCE: 20

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Gln Pro
```

```
            130                 135                 140
Arg Ala His Arg Ser Ser Pro Trp His Pro Pro Arg Ala Pro Leu
145                 150                 155                 160

Gly Ala Gln Arg Pro Trp Ala Ala Trp Ser Arg Thr Thr Ser Pro Asn
                165                 170                 175

Arg Glu Pro Lys Ser Cys Asp Lys Thr His Thr Cys Pro Pro Cys Pro
                180                 185                 190

Met Ile Ser Arg Thr Pro Glu Val Thr Cys Val Val Val Asp Val Ser
            195                 200                 205

His Glu Asp Pro Glu Val Lys Phe Asn Trp Tyr Val Asp Gly Val Glu
        210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
                260                 265                 270

Ile Glu Lys Thr Ile Ser Lys Ala Lys Gly Gln Pro Arg Glu Pro Gln
            275                 280                 285

Gly Pro His Gly Gln Arg Pro Ala Arg Pro Thr Leu Cys Pro Glu Ser
        290                 295                 300

Asp Arg Cys Thr Asn Leu Cys Pro Thr Gly Gln Pro Arg Glu Pro Gln
305                 310                 315                 320

Val Tyr Thr Leu Pro Pro Ser Arg Asp Glu Leu Thr Lys Asn Gln Val
                325                 330                 335

Ser Leu Thr Cys Leu Val Lys Gly Phe Tyr Pro Ser Asp Ile Ala Val
                340                 345                 350

Glu Trp Glu Ser Asn Gly Gln Pro Glu Asn Asn Tyr Lys Thr Thr Pro
            355                 360                 365

Pro Val Leu Asp Ser Asp Gly Ser Phe Phe Leu Tyr Ser Lys Leu Thr
        370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys Ala Glu Ala Ala Ala Lys Glu Ala Ala Ala Lys Ala
                420                 425                 430

Gly Ser Cys Asp Leu Pro Gln Thr His Ser Leu Gly Ser Arg Arg Thr
            435                 440                 445

Leu Met Leu Leu Ala Gln Met Arg Arg Ile Ser Leu Phe Ser Cys Leu
        450                 455                 460

Lys Asp Arg His Asp Phe Gly Phe Pro Gln Glu Glu Phe Gly Asn Gln
465                 470                 475                 480

Phe Gln Lys Ala Glu Thr Ile Pro Val Leu His Glu Met Ile Gln Gln
                485                 490                 495

Ile Phe Asn Leu Phe Ser Thr Lys Asp Ser Ser Ala Ala Trp Asp Glu
            500                 505                 510

Thr Leu Leu Asp Lys Phe Tyr Thr Glu Leu Tyr Gln Gln Leu Asn Asp
        515                 520                 525

Leu Glu Ala Cys Val Ile Gln Gly Val Gly Val Thr Glu Thr Pro Leu
530                 535                 540

Met Lys Glu Asp Ser Ile Leu Ala Val Arg Lys Tyr Phe Gln Arg Ile
545                 550                 555                 560
```

```
Thr Leu Tyr Leu Lys Glu Lys Tyr Ser Pro Cys Ala Trp Glu Val
            565                 570                 575

Val Arg Ala Glu Ile Met Arg Ser Phe Ser Leu Ser Thr Asn Leu Gln
            580                 585                 590

Glu Ser Leu Arg Ser Lys Glu
        595
```

<210> SEQ ID NO 21
<211> LENGTH: 393
<212> TYPE: DNA
<213> ORGANISM: Artificial
<220> FEATURE:
<223> OTHER INFORMATION: Nucleic acid encoding fusion protein.

<400> SEQUENCE: 21

```
atgggatgga gctgggtaat cctctttctc ctgtcagtaa ctgcaggtgt ccactcccag    60
tctgtgttga cgcagccgcc ctcagtgtct gcggccccag gacagaaggt caccatctcc   120
tgctctggaa gcagctccaa cattgggaat aattatgtat cctggtacca gcagctccca   180
ggaacagccc ccaaactcct catctatgat cacaccaatc ggcccgcagg ggtccctgac   240
cgattctctg gctccaagtc tggcacctca gcctccctgg ccatcagtgg gttccggtcc   300
gaggatgagg ctgattatta ctgtgcctcc tgggactaca ccctctcggg ctgggtgttc   360
ggaggaggga ccaaggtcac cgtcctaggt gag                                393
```

<210> SEQ ID NO 22
<211> LENGTH: 131
<212> TYPE: PRT
<213> ORGANISM: Artificial
<220> FEATURE:
<223> OTHER INFORMATION: Fusion protein.

<400> SEQUENCE: 22

```
Met Gly Trp Ser Trp Val Ile Leu Phe Leu Leu Ser Val Thr Ala Gly
1               5                   10                  15

Val His Ser Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Val Ser Trp Tyr Gln Gln Leu Pro Gly Thr Ala Pro
    50                  55                  60

Lys Leu Leu Ile Tyr Asp His Thr Asn Arg Pro Ala Gly Val Pro Asp
65                  70                  75                  80

Arg Phe Ser Gly Ser Lys Ser Gly Thr Ser Ala Ser Leu Ala Ile Ser
                85                  90                  95

Gly Phe Arg Ser Glu Asp Glu Ala Asp Tyr Tyr Cys Ala Ser Trp Asp
            100                 105                 110

Tyr Thr Leu Ser Gly Trp Val Phe Gly Gly Gly Thr Lys Val Thr Val
        115                 120                 125

Leu Gly Glu
    130
```

<210> SEQ ID NO 23
<211> LENGTH: 1676
<212> TYPE: DNA
<213> ORGANISM: Artificial
<220> FEATURE:
<223> OTHER INFORMATION: Nucleic acid encoding fusion protein.

<400> SEQUENCE: 23

```
atgggatgga gctgggtaat gcatctttct cctgtcagta actgcagatg cccgggaaag    60
gcctggagta catggggctc atctatcctg gtgactctga caccaaatac agcccgtcct   120
tccaaggcca ggtcaccatc tcagtcgaca agtccgtcag cactgcctac ttgcaatgga   180
gcagtctgaa gccctcggac agcgccgtgt atttttgtgc agacatgac gtgggatatt    240
gcaccgaccg gacttgcgca aagtggcctg aatacttcca gcattggggc cagggcaccc   300
tggtcaccgt ctcctcagct agccaaccaa gggcccatcg gtcttccccc tggcaccctc   360
ctccaagagc acctctgggg gcacagcggc cctgggctgc ctggtcaagg actacttccc   420
cgaaccggga gcccaaatct gtgacaaaa ctcacacatg cccaccgtgc ccaatgatct    480
cccggacccc tgaggtcaca tgcgtggtgg tggacgtgag ccacgaagac cctgaggtca   540
agttcaactg gtacgtggac ggcgtggagg tgcataatgc caagacaaag ccgcgggagg   600
agcagtacaa cagcacgtac cgggtggtca gcgtcctcac cgtcctgcac caggactggc   660
tgaatggcaa ggagtacaag tgcaaggtct ccaacaaagc cctcccagcc cccatcgaga   720
aaaccatctc caaagccaaa ggtgggaccc gtggggtgcg agggccacat ggacagaggc   780
cggctcggcc caccctctgc cctgagagtg accgctgtac caacctctgt cctacagggc   840
agccccgaga accacaggtg tacaccctgc ccccatcccg ggatgagctg accaagaacc   900
aggtcagcct gacctgcctg gtcaaaggct tctatcccag cgacatcgcc gtggagtggg   960
agagcaatgg gcagccggag aacaactaca agaccacgcc tcccgtgctg gactccgacg  1020
gctccttctt cctctacagc aagctcaccg tggacaagag caggtggcag caggggaacg  1080
tcttctcatg ctccgtgatg catgaggctc tgcacaacca ctacacgcag aagagcctct  1140
ccctgtctcc gggtaaatct ggtggcggtg atcctgtga cctgcctcag actcataacc  1200
tcaggaacaa gagagccttg acactcctgg tacaaatgag gagactctcc cctctctcct  1260
gcctgaagga caggaaggac tttggattcc gcaggagaa ggtggatgcc cagcagatca   1320
agaaggctca agccatccct gtcctgagtg agctgaccca gcagatcctg aacatcttca   1380
catcaaagga ctcatctgct gcttggaatg caaccctcct agactcattc tgcaatgacc   1440
tccaccagca gctcaatgac ctgcaaggtt gtctgatgca gcaggtgggg gtgcaggaat   1500
ttcccctgac ccaggaagat gccctgctgg ctgtgaggaa atacttccac aggatcactg   1560
tgtacctgag agagaagaaa cacagcccct gtgcctggga ggtggtcaga gcagaagtct   1620
ggagagccct gtcttcctct gccaatgtgc tgggaagact gagagaagag aaatga       1676
```

<210> SEQ ID NO 24
<211> LENGTH: 557
<212> TYPE: PRT
<213> ORGANISM: Artificial
<220> FEATURE:
<223> OTHER INFORMATION: Fusion protein.

<400> SEQUENCE: 24

```
Met Gly Trp Ser Trp Val Met His Leu Ser Pro Val Ser Asn Cys Met
1               5                   10                  15

Pro Gly Lys Gly Leu Glu Tyr Met Gly Leu Ile Tyr Pro Gly Asp Ser
            20                  25                  30

Asp Thr Lys Tyr Ser Pro Ser Phe Gln Gly Gln Val Thr Ile Ser Val
        35                  40                  45

Asp Lys Ser Val Ser Thr Ala Tyr Leu Gln Trp Ser Ser Leu Lys Pro
    50                  55                  60
```

```
Ser Asp Ser Ala Val Tyr Phe Cys Ala Arg His Asp Val Gly Tyr Cys
 65                  70                  75                  80

Thr Asp Arg Thr Cys Ala Lys Trp Pro Glu Tyr Phe Gln His Trp Gly
                 85                  90                  95

Gln Gly Thr Leu Val Thr Val Ser Ser Ala Ser Gln Pro Arg Ala His
            100                 105                 110

Arg Ser Ser Pro Trp His Pro Pro Arg Ala Pro Leu Gly Ala Gln
        115                 120                 125

Arg Pro Trp Ala Ala Trp Ser Arg Thr Thr Ser Pro Asn Arg Glu Pro
130                 135                 140

Lys Ser Cys Asp Lys Thr His Thr Cys Pro Pro Cys Pro Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gly Thr Arg Gly Val Arg Gly Pro His
                245                 250                 255

Gly Gln Arg Pro Ala Arg Pro Thr Leu Cys Pro Glu Ser Asp Arg Cys
            260                 265                 270

Thr Asn Leu Cys Pro Thr Gly Gln Pro Arg Glu Pro Gln Val Tyr Thr
        275                 280                 285

Leu Pro Pro Ser Arg Asp Glu Leu Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
        370                 375                 380

Lys Ser Gly Gly Gly Ser Cys Asp Leu Pro Gln Thr His Asn Leu
385                 390                 395                 400

Arg Asn Lys Arg Ala Leu Thr Leu Leu Val Gln Met Arg Arg Leu Ser
                405                 410                 415

Pro Leu Ser Cys Leu Lys Asp Arg Lys Asp Phe Gly Phe Pro Gln Glu
            420                 425                 430

Lys Val Asp Ala Gln Gln Ile Lys Lys Ala Gln Ala Ile Pro Val Leu
        435                 440                 445

Ser Glu Leu Thr Gln Gln Ile Leu Asn Ile Phe Thr Ser Lys Asp Ser
        450                 455                 460

Ser Ala Ala Trp Asn Ala Thr Leu Leu Asp Ser Phe Cys Asn Asp Leu
465                 470                 475                 480
```

His Gln Gln Leu Asn Asp Leu Gln Gly Cys Leu Met Gln Gln Val Gly
            485                 490                 495

Val Gln Glu Phe Pro Leu Thr Gln Glu Asp Ala Leu Leu Ala Val Arg
        500                 505                 510

Lys Tyr Phe His Arg Ile Thr Val Tyr Leu Arg Glu Lys Lys His Ser
    515                 520                 525

Pro Cys Ala Trp Glu Val Val Arg Ala Glu Val Trp Arg Ala Leu Ser
530                 535                 540

Ser Ser Ala Asn Val Leu Gly Arg Leu Arg Glu Glu Lys
545                 550                 555

<210> SEQ ID NO 25
<211> LENGTH: 1700
<212> TYPE: DNA
<213> ORGANISM: Artificial
<220> FEATURE:
<223> OTHER INFORMATION: Nucleic acid encoding fusion protein.

<400> SEQUENCE: 25

| | | |
|---|---|---|
| atgggatgga gctgggtaat gcatctttct cctgtcagta actgcagatg cccgggaaag | 60 |
| gcctggagta catggggctc atctatcctg gtgactctga caccaaatac agcccgtcct | 120 |
| tccaaggcca ggtcaccatc tcagtcgaca gtccgtcag cactgcctac ttgcaatgga | 180 |
| gcagtctgaa gccctcggac agcgccgtgt atttttgtgc gagacatgac gtgggatatt | 240 |
| gcaccgaccg gacttgcgca aagtggcctg aatacttcca gcattggggc cagggcaccc | 300 |
| tggtcaccgt ctcctcagct agccaaccaa gggcccatcg tcttccccc tggcaccctc | 360 |
| ctccaagagc acctctgggg gcacagcggc cctgggctgc ctggtcaagg actacttccc | 420 |
| cgaaccggga gcccaaatct tgtgacaaaa ctcacacatg cccaccgtgc ccaatgatct | 480 |
| cccggacccc tgaggtcaca tgcgtggtgg tggacgtgag ccacgaagac cctgaggtca | 540 |
| agttcaactg gtacgtggac ggcgtggagg tgcataatgc caagacaaag ccgcgggagg | 600 |
| agcagtacaa cagcacgtac cgggtggtca gcgtcctcac cgtcctgcac caggactggc | 660 |
| tgaatggcaa ggagtacaag tgcaaggtct ccaacaaagc cctcccagcc cccatcgaga | 720 |
| aaaccatctc caaagccaaa ggtgggaccc gtggggtgcg agggccacat ggacagaggc | 780 |
| cggctcggcc caccctctgc cctgagagtg accgctgtac caacctctgt cctacagggc | 840 |
| agccccgaga accacaggtg tacaccctgc cccatcccg ggatgagctg accaagaacc | 900 |
| aggtcagcct gacctgcctg gtcaaaggct tctatcccag cgacatcgcc gtggagtggg | 960 |
| agagcaatgg gcagccggag aacaactaca agaccacgcc tcccgtgctg gactccgacg | 1020 |
| gctccttctt cctctacagc aagctcaccg tggacaagag caggtggcag caggggaacg | 1080 |
| tcttctcatg ctccgtgatg catgaggctc tgcacaacca ctacacgcag aagagcctct | 1140 |
| ccctgtctcc gggtaaagca gaggccgcag ctaaagaggc cgcagccaaa gcgggatcct | 1200 |
| gtgacctgcc tcagactcat aacctcagga caagagagc cttgacactc tggtacaaa | 1260 |
| tgaggagact ctcccctctc tcctgcctga aggacaggaa ggactttgga ttcccgcagg | 1320 |
| agaaggtgga tgcccagcag atcaagaagg ctcaagccat ccctgtcctg agtgagctga | 1380 |
| cccagcagat cctgaacatc ttcacatcaa aggactcatc tgctgcttgg aatgcaaccc | 1440 |
| tcctagactc attctgcaat gacctccacc agcagctcaa tgacctgcaa ggttgtctga | 1500 |
| tgcagcaggt gggggtgcag gaatttcccc tgacccagga agatgccctg ctggctgtga | 1560 |
| ggaaatactt ccacaggatc actgtgtacc tgagagagaa gaaacacagc ccctgtgcct | 1620 |

-continued

```
gggaggtggt cagagcagaa gtctggagag ccctgtcttc ctctgccaat gtgctgggaa    1680
gactgagaga agagaaatga                                                1700
```

\<210\> SEQ ID NO 26
\<211\> LENGTH: 564
\<212\> TYPE: PRT
\<213\> ORGANISM: Artificial
\<220\> FEATURE:
\<223\> OTHER INFORMATION: Fusion protein.

\<400\> SEQUENCE: 26

```
Met Gly Trp Ser Trp Val Met His Leu Ser Pro Val Ser Asn Cys Met
1               5                   10                  15

Pro Gly Lys Gly Leu Glu Tyr Met Gly Leu Ile Tyr Pro Gly Asp Ser
            20                  25                  30

Asp Thr Lys Tyr Ser Pro Ser Phe Gln Gly Gln Val Thr Ile Ser Val
        35                  40                  45

Asp Lys Ser Val Ser Thr Ala Tyr Leu Gln Trp Ser Ser Leu Lys Pro
    50                  55                  60

Ser Asp Ser Ala Val Tyr Phe Cys Ala Arg His Asp Val Gly Tyr Cys
65                  70                  75                  80

Thr Asp Arg Thr Cys Ala Lys Trp Pro Glu Tyr Phe Gln His Trp Gly
                85                  90                  95

Gln Gly Thr Leu Val Thr Val Ser Ser Ala Ser Gln Pro Arg Ala His
            100                 105                 110

Arg Ser Ser Pro Trp His Pro Pro Arg Ala Pro Leu Gly Ala Gln
        115                 120                 125

Arg Pro Trp Ala Ala Trp Ser Arg Thr Thr Ser Pro Asn Arg Glu Pro
    130                 135                 140

Lys Ser Cys Asp Lys Thr His Thr Cys Pro Pro Cys Pro Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gly Thr Arg Gly Val Arg Gly Pro His
                245                 250                 255

Gly Gln Arg Pro Ala Arg Pro Thr Leu Cys Pro Glu Ser Asp Arg Cys
            260                 265                 270

Thr Asn Leu Cys Pro Thr Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350
```

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
370                 375                 380

Lys Ser Ala Glu Ala Ala Ala Lys Glu Ala Ala Ala Lys Ala Cys Asp
385                 390                 395                 400

Leu Pro Gln Thr His Asn Leu Arg Asn Lys Arg Ala Leu Thr Leu Leu
                405                 410                 415

Val Gln Met Arg Arg Leu Ser Pro Leu Ser Cys Leu Lys Asp Arg Lys
            420                 425                 430

Asp Phe Gly Phe Pro Gln Glu Lys Val Asp Ala Gln Ile Lys Lys
        435                 440                 445

Ala Gln Ala Ile Pro Val Leu Ser Glu Leu Thr Gln Gln Ile Leu Asn
    450                 455                 460

Ile Phe Thr Ser Lys Asp Ser Ser Ala Ala Trp Asn Ala Thr Leu Leu
465                 470                 475                 480

Asp Ser Phe Cys Asn Asp Leu His Gln Gln Leu Asn Asp Leu Gln Gly
                485                 490                 495

Cys Leu Met Gln Gln Val Gly Val Gln Glu Phe Pro Leu Thr Gln Glu
            500                 505                 510

Asp Ala Leu Leu Ala Val Arg Lys Tyr Phe His Arg Ile Thr Val Tyr
        515                 520                 525

Leu Arg Glu Lys Lys His Ser Pro Cys Ala Trp Glu Val Val Arg Ala
    530                 535                 540

Glu Val Trp Arg Ala Leu Ser Ser Ala Asn Val Leu Gly Arg Leu
545                 550                 555                 560

Arg Glu Glu Lys

<210> SEQ ID NO 27
<211> LENGTH: 1673
<212> TYPE: DNA
<213> ORGANISM: Artificial
<220> FEATURE:
<223> OTHER INFORMATION: Nucleic acid encoding fusion protein.

<400> SEQUENCE: 27

| | | | | | |
|---|---|---|---|---|---|
| atgggatgga | gctgggtaat | gcatctttct | cctgtcagta | actgcagatg | cccgggaaag | 60 |
| gcctggagta | catggggctc | atctatcctg | gtgactctga | caccaaatac | agcccgtcct | 120 |
| tccaaggcca | ggtcaccatc | tcagtcgaca | agtccgtcag | cactgcctac | ttgcaatgga | 180 |
| gcagtctgaa | gccctcggac | agcgccgtgt | atttttgtgc | gagacatgac | gtgggatatt | 240 |
| gcaccgaccg | gacttgcgca | agtggcctga | atacttccag | cattggggc | cagggcaccc | 300 |
| tggtcaccgt | ctcctcagct | agccaaccaa | gggcccatcg | gtcttccccc | tggcaccctc | 360 |
| ctccaagagc | acctctgggg | gcacagcggc | cctgggctgc | ctggtcaagg | actacttccc | 420 |
| cgaaccggga | gcccaaatct | tgtgacaaaa | ctcacacatg | cccaccgtgc | ccaatgatct | 480 |
| cccggacccc | tgaggtcaca | tgcgtggtgg | tggacgtgag | ccacgaagac | cctgaggtca | 540 |
| agttcaactg | gtacgtggac | ggcgtggagg | tgcataatgc | caagacaaag | ccgcgggagg | 600 |
| agcagtacaa | cagcacgtac | cgggtggtca | gcgtcctcac | cgtcctgcac | caggactggc | 660 |
| tgaatggcaa | ggagtacaag | tgcaaggtct | ccaacaaagc | cctcccagcc | cccatcgaga | 720 |
| aaaccatctc | caaagccaaa | ggtgggaccc | gtggggtgcg | agggccacat | ggacagaggc | 780 |
| cggctcggcc | caccctctgc | cctgagagtg | accgctgtac | caacctctgt | cctacagggc | 840 |

```
agccccgaga accacaggtg tacaccctgc ccccatcccg ggatgagctg accaagaacc    900
aggtcagcct gacctgcctg gtcaaaggct tctatcccag cgacatcgcc gtggagtggg    960
agagcaatgg gcagccggag aacaactaca agaccacgcc tcccgtgctg gactccgacg   1020
gctccttctt cctctacagc aagctcaccg tggacaagag caggtggcag caggggaacg   1080
tcttctcatg ctccgtgatg catgaggctc tgcacaacca ctacacgcag aagagcctct   1140
ccctgtctcc gggtaaatct ggtggcggtg gatcctgtga tctgcctcaa acccacagcc   1200
tgggtagcag gaggaccttg atgctcctgg cacagatgag gagaatctct cttttctcct   1260
gcttgaagga cagacatgac tttggatttc cccaggagga gtttggcaac cagttccaaa   1320
aggctgaaac catccctgtc ctccatgaga tgatccagca gatcttcaat ctcttcagca   1380
caaaggactc atctgctgct gggatgaga ccctcctaga caaattctac actgaactct   1440
accagcagct gaatgacctg gaagcctgtg tgatacaggg ggtgggggtg acagagactc   1500
ccctgatgaa ggaggactcc attctggctg tgaggaaata cttccaaaga atcactctct   1560
atctgaaaga gaagaaatac agcccttgtg cctgggaggt tgtcagagca gaaatcatga   1620
gatcttttc tttgtcaaca aacttgcaag aaagtttaag aagtaaggaa tga           1673
```

<210> SEQ ID NO 28
<211> LENGTH: 591
<212> TYPE: PRT
<213> ORGANISM: Artificial
<220> FEATURE:
<223> OTHER INFORMATION: Fusion protein.

<400> SEQUENCE: 28

```
Met Tyr Leu Gly Leu Asn Cys Val Ile Ile Val Phe Leu Leu Lys Gly
  1               5                  10                  15

Val Gln Ser Gln Val Gln Leu Gln Gln Pro Gly Ala Glu Leu Val Lys
             20                  25                  30

Pro Gly Ala Ser Val Lys Met Ser Cys Lys Ala Ser Gly Tyr Thr Phe
         35                  40                  45

Thr Ser Tyr Asn Met His Trp Val Lys Gln Thr Pro Gly Arg Gly Leu
     50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Gln Pro
    130                 135                 140

Arg Ala His Arg Ser Ser Pro Trp His Pro Pro Arg Ala Pro Leu
145                 150                 155                 160

Gly Ala Gln Arg Pro Trp Ala Ala Trp Ser Arg Thr Thr Ser Pro Asn
                165                 170                 175

Arg Glu Pro Lys Ser Cys Asp Lys Thr His Thr Cys Pro Pro Cys Pro
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
```

```
                    210                 215                 220
Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gly Thr Arg Gly Val Arg
        275                 280                 285

Gly Pro His Gly Gln Arg Pro Ala Arg Pro Thr Leu Cys Pro Glu Ser
    290                 295                 300

Asp Arg Cys Thr Asn Leu Cys Pro Thr Gly Gln Pro Arg Glu Pro Gln
305                 310                 315                 320

Val Tyr Thr Leu Pro Pro Ser Arg Asp Glu Leu Thr Lys Asn Gln Val
                325                 330                 335

Ser Leu Thr Cys Leu Val Lys Gly Phe Tyr Pro Ser Asp Ile Ala Val
            340                 345                 350

Glu Trp Glu Ser Asn Gly Gln Pro Glu Asn Asn Tyr Lys Thr Thr Pro
        355                 360                 365

Pro Val Leu Asp Ser Asp Gly Ser Phe Phe Leu Tyr Ser Lys Leu Thr
    370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys Ser Gly Gly Gly Ser Cys Asp Leu Pro Gln Thr
            420                 425                 430

His Ser Leu Gly Ser Arg Arg Thr Leu Met Leu Leu Ala Gln Met Arg
        435                 440                 445

Arg Ile Ser Leu Phe Ser Cys Leu Lys Asp Arg His Asp Phe Gly Phe
    450                 455                 460

Pro Gln Glu Glu Phe Gly Asn Gln Phe Gln Lys Ala Glu Thr Ile Pro
465                 470                 475                 480

Val Leu His Glu Met Ile Gln Gln Ile Phe Asn Leu Phe Ser Thr Lys
                485                 490                 495

Asp Ser Ser Ala Ala Trp Asp Glu Thr Leu Leu Asp Lys Phe Tyr Thr
            500                 505                 510

Glu Leu Tyr Gln Gln Leu Asn Asp Leu Glu Ala Cys Val Ile Gln Gly
        515                 520                 525

Val Gly Val Thr Glu Thr Pro Leu Met Lys Glu Asp Ser Ile Leu Ala
    530                 535                 540

Val Arg Lys Tyr Phe Gln Arg Ile Thr Leu Tyr Leu Lys Glu Lys Lys
545                 550                 555                 560

Tyr Ser Pro Cys Ala Trp Glu Val Val Arg Ala Glu Ile Met Arg Ser
                565                 570                 575

Phe Ser Leu Ser Thr Asn Leu Gln Glu Ser Leu Arg Ser Lys Glu
            580                 585                 590

<210> SEQ ID NO 29
<211> LENGTH: 1697
<212> TYPE: DNA
<213> ORGANISM: Artificial
<220> FEATURE:
<223> OTHER INFORMATION: Nucleic acid encoding fusion protein.
```

<400> SEQUENCE: 29

```
atgggatgga gctgggtaat gcatctttct cctgtcagta actgcagatg cccgggaaag      60
gcctggagta catggggctc atctatcctg gtgactctga caccaaatac agcccgtcct     120
tccaaggcca ggtcaccatc tcagtcgaca agtccgtcag cactgcctac ttgcaatgga     180
gcagtctgaa gccctcggac agcgccgtgt attttgtgc agacatgac gtgggatatt      240
gcaccgaccg gacttgcgca aagtggcctg aatacttcca gcattgggc cagggcaccc     300
tggtcaccgt ctcctcagct agccaaccaa gggcccatcg tcttccccc tggcaccctc     360
ctccaagagc acctctgggg gcacagcggc cctgggctgc ctggtcaagg actacttccc     420
cgaaccggga gcccaaatct tgtgacaaaa ctcacacatg cccaccgtgc ccaatgatct     480
cccggacccc tgaggtcaca tgcgtggtgg tggacgtgag ccacgaagac cctgaggtca     540
agttcaactg gtacgtggac ggcgtggagg tgcataatgc caagacaaag ccgcgggagg     600
agcagtacaa cagcacgtac cgggtggtca gcgtcctcac cgtcctgcac caggactggc     660
tgaatggcaa ggagtacaag tgcaaggtct ccaacaaagc cctcccagcc cccatcgaga     720
aaaccatctc caaagccaaa ggtgggaccc gtggggtgcg agggccacat ggacagaggc     780
cggctcggcc caccctctgc cctgagagtg accgctgtac aacctctgt cctacagggc      840
agccccgaga ccacaggtg tacaccctgc ccccatcccg ggatgagctg accaagaacc      900
aggtcagcct gacctgcctg gtcaaaggct tctatcccag cgacatcgcc gtggagtggg     960
agagcaatgg gcagccggag aacaactaca agaccacgcc tcccgtgctg gactccgacg    1020
gctccttctt cctctacagc aagctcaccg tggacaagag caggtggcag caggggaacg    1080
tcttctcatg ctccgtgatg catgaggctc tgcacaacca ctacacgcag aagagcctct    1140
cccctgtctcc gggtaaagca gaggccgcag ctaaagaggc cgcagccaaa gcgggatcct    1200
gtgatctgcc tcaaacccac agcctgggta gcaggaggac cttgatgctc ctggcacaga    1260
tgaggagaat ctctcttttc tcctgcttga aggacagaca tgactttgga ttccccagg     1320
aggagtttgg caaccagttc caaaaggctg aaaccatccc tgtcctccat gagatgatcc    1380
agcagatctt caatctcttc agcacaaagg actcatctgc tgcttgggat gagaccctcc    1440
tagacaaatt ctacactgaa ctctaccagc agctgaatga cctggaagcc tgtgtgatac    1500
aggggggtggg ggtgacagag actccctga tgaaggagga ctccattctg gctgtgagga    1560
aatacttcca agaatcact ctctatctga agagaagaa atacagccct tgtgcctggg     1620
aggttgtcag agcagaaatc atgagatctt tttctttgtc aacaaacttg caagaaagtt    1680
taagaagtaa ggaatga                                                    1697
```

<210> SEQ ID NO 30
<211> LENGTH: 598
<212> TYPE: PRT
<213> ORGANISM: Artificial
<220> FEATURE:
<223> OTHER INFORMATION: Fusion protein.

<400> SEQUENCE: 30

```
Met Tyr Leu Gly Leu Asn Cys Val Ile Ile Val Phe Leu Leu Lys Gly
  1               5                  10                  15

Val Gln Ser Gln Val Gln Leu Gln Gln Pro Gly Ala Glu Leu Val Lys
             20                  25                  30

Pro Gly Ala Ser Val Lys Met Ser Cys Lys Ala Ser Gly Tyr Thr Phe
         35                  40                  45
```

```
Thr Ser Tyr Asn Met His Trp Val Lys Gln Thr Pro Gly Arg Gly Leu
 50              55                  60
Glu Trp Ile Gly Ala Ile Tyr Pro Gly Asn Gly Asp Thr Ser Tyr Asn
 65              70                  75                  80
Gln Lys Phe Lys Gly Lys Ala Thr Leu Thr Ala Asp Lys Ser Ser Ser
                 85                  90                  95
Thr Ala Tyr Met Gln Leu Ser Ser Leu Thr Ser Glu Asp Ser Ala Val
                100                 105                 110
Tyr Tyr Cys Ala Arg Ser Thr Tyr Tyr Gly Gly Asp Trp Tyr Phe Asn
                115                 120                 125
Val Trp Gly Ala Gly Thr Thr Val Thr Val Ser Ala Ala Ser Gln Pro
130                 135                 140
Arg Ala His Arg Ser Ser Pro Trp His Pro Pro Arg Ala Pro Leu
145                 150                 155                 160
Gly Ala Gln Arg Pro Trp Ala Ala Trp Ser Arg Thr Thr Ser Pro Asn
                165                 170                 175
Arg Glu Pro Lys Ser Cys Asp Lys Thr His Thr Cys Pro Pro Cys Pro
                180                 185                 190
Met Ile Ser Arg Thr Pro Glu Val Thr Cys Val Val Val Asp Val Ser
                195                 200                 205
His Glu Asp Pro Glu Val Lys Phe Asn Trp Tyr Val Asp Gly Val Glu
                210                 215                 220
Val His Asn Ala Lys Thr Lys Pro Arg Glu Glu Gln Tyr Asn Ser Thr
225                 230                 235                 240
Tyr Arg Val Val Ser Val Leu Thr Val Leu His Gln Asp Trp Leu Asn
                245                 250                 255
Gly Lys Glu Tyr Lys Cys Lys Val Ser Asn Lys Ala Leu Pro Ala Pro
                260                 265                 270
Ile Glu Lys Thr Ile Ser Lys Ala Lys Gly Gln Pro Arg Glu Pro Gln
                275                 280                 285
Gly Pro His Gly Gln Arg Pro Ala Arg Pro Thr Leu Cys Pro Glu Ser
                290                 295                 300
Asp Arg Cys Thr Asn Leu Cys Pro Thr Gly Gln Pro Arg Glu Pro Gln
305                 310                 315                 320
Val Tyr Thr Leu Pro Pro Ser Arg Asp Glu Leu Thr Lys Asn Gln Val
                325                 330                 335
Ser Leu Thr Cys Leu Val Lys Gly Phe Tyr Pro Ser Asp Ile Ala Val
                340                 345                 350
Glu Trp Glu Ser Asn Gly Gln Pro Glu Asn Asn Tyr Lys Thr Thr Pro
                355                 360                 365
Pro Val Leu Asp Ser Asp Gly Ser Phe Phe Leu Tyr Ser Lys Leu Thr
                370                 375                 380
Val Asp Lys Ser Arg Trp Gln Gln Gly Asn Val Phe Ser Cys Ser Val
385                 390                 395                 400
Met His Glu Ala Leu His Asn His Tyr Thr Gln Lys Ser Leu Ser Leu
                405                 410                 415
Ser Pro Gly Lys Ser Ala Glu Ala Ala Lys Glu Ala Ala Lys
                420                 425                 430
Ala Cys Asp Leu Pro Gln Thr His Ser Leu Gly Ser Arg Arg Thr Leu
                435                 440                 445
Met Leu Leu Ala Gln Met Arg Arg Ile Ser Leu Phe Ser Cys Leu Lys
450                 455                 460
Asp Arg His Asp Phe Gly Phe Pro Gln Glu Glu Phe Gly Asn Gln Phe
```

```
                465                 470                 475                 480
Gln Lys Ala Glu Thr Ile Pro Val Leu His Glu Met Ile Gln Gln Ile
                    485                 490                 495
Phe Asn Leu Phe Ser Thr Lys Asp Ser Ser Ala Ala Trp Asp Glu Thr
                500                 505                 510
Leu Leu Asp Lys Phe Tyr Thr Glu Leu Tyr Gln Gln Leu Asn Asp Leu
                515                 520                 525
Glu Ala Cys Val Ile Gln Gly Val Gly Val Thr Glu Thr Pro Leu Met
            530                 535                 540
Lys Glu Asp Ser Ile Leu Ala Val Arg Lys Tyr Phe Gln Arg Ile Thr
545                 550                 555                 560
Leu Tyr Leu Lys Glu Lys Lys Tyr Ser Pro Cys Ala Trp Glu Val Val
                565                 570                 575
Arg Ala Glu Ile Met Arg Ser Phe Ser Leu Ser Thr Asn Leu Gln Glu
                580                 585                 590
Ser Leu Arg Ser Lys Glu
            595

<210> SEQ ID NO 31
<211> LENGTH: 15
<212> TYPE: PRT
<213> ORGANISM: Artificial
<220> FEATURE:
<223> OTHER INFORMATION: Peptide linker.

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 5
<212> TYPE: PRT
<213> ORGANISM: Artificial
<220> FEATURE:
<223> OTHER INFORMATION: Peptide linker.

<400> SEQUENCE: 32

Gly Gly Gly Gly Ser
1               5

<210> SEQ ID NO 33
<211> LENGTH: 7
<212> TYPE: PRT
<213> ORGANISM: Artificial
<220> FEATURE:
<223> OTHER INFORMATION: Peptide linker.

<400> SEQUENCE: 33

Ala Glu Ala Ala Ala Lys Ala
1               5

<210> SEQ ID NO 34
<211> LENGTH: 12
<212> TYPE: PRT
<213> ORGANISM: Artificial
<220> FEATURE:
<223> OTHER INFORMATION: Peptide linker

<400> SEQUENCE: 34

Ala Glu Ala Ala Ala Lys Glu Ala Ala Ala Lys Ala
1               5                   10
```

```
<210> SEQ ID NO 35
<211> LENGTH: 17
<212> TYPE: PRT
<213> ORGANISM: Artificial
<220> FEATURE:
<223> OTHER INFORMATION: Peptide linker

<400> SEQUENCE: 35

Ala Glu Ala Ala Ala Lys Glu Ala Ala Ala Lys Glu Ala Ala Ala Lys
1               5                   10                  15

Ala

<210> SEQ ID NO 36
<211> LENGTH: 22
<212> TYPE: PRT
<213> ORGANISM: Artificial
<220> FEATURE:
<223> OTHER INFORMATION: Peptide linker

<400> SEQUENCE: 36

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 37
<211> LENGTH: 27
<212> TYPE: PRT
<213> ORGANISM: Artificial
<220> FEATURE:
<223> OTHER INFORMATION: Peptide linker

<400> SEQUENCE: 37

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 38
<211> LENGTH: 7
<212> TYPE: PRT
<213> ORGANISM: Artificial
<220> FEATURE:
<223> OTHER INFORMATION: Peptide linker.

<400> SEQUENCE: 38

Ala Glu Ala Ala Ala Lys Ala
1               5

<210> SEQ ID NO 39
<211> LENGTH: 5
<212> TYPE: PRT
<213> ORGANISM: Artificial
<220> FEATURE:
<223> OTHER INFORMATION: Peptide linker.

<400> SEQUENCE: 39

Gly Gly Gly Gly Gly
1               5

<210> SEQ ID NO 40
<211> LENGTH: 8
<212> TYPE: PRT
<213> ORGANISM: Artificial
<220> FEATURE:
<223> OTHER INFORMATION: Peptide linker.
```

```
<400> SEQUENCE: 40

Gly Gly Gly Gly Gly Gly Gly Gly
1               5

<210> SEQ ID NO 41
<211> LENGTH: 5
<212> TYPE: PRT
<213> ORGANISM: Artificial
<220> FEATURE:
<223> OTHER INFORMATION: Peptide linker.

<400> SEQUENCE: 41

Gly Gly Ala Gly Gly
1               5

<210> SEQ ID NO 42
<211> LENGTH: 10
<212> TYPE: PRT
<213> ORGANISM: Artificial
<220> FEATURE:
<223> OTHER INFORMATION: Peptide linker.

<400> SEQUENCE: 42

Gly Ala Gly Ala Gly Ala Gly Ala Gly Ala
1               5                   10

<210> SEQ ID NO 43
<211> LENGTH: 18
<212> TYPE: PRT
<213> ORGANISM: Artificial
<220> FEATURE:
<223> OTHER INFORMATION: Peptide linker.

<400> SEQUENCE: 43

Arg Pro Leu Ser Tyr Arg Pro Pro Phe Pro Phe Gly Phe Pro Ser Val
1               5                   10                  15

Arg Pro

<210> SEQ ID NO 44
<211> LENGTH: 18
<212> TYPE: PRT
<213> ORGANISM: Artificial
<220> FEATURE:
<223> OTHER INFORMATION: Peptide linker.

<400> SEQUENCE: 44

Tyr Pro Arg Ser Ile Tyr Ile Arg Arg Arg His Pro Ser Pro Ser Leu
1               5                   10                  15

Thr Thr

<210> SEQ ID NO 45
<211> LENGTH: 18
<212> TYPE: PRT
<213> ORGANISM: Artificial
<220> FEATURE:
<223> OTHER INFORMATION: Peptide linker.

<400> SEQUENCE: 45

Thr Pro Ser His Leu Ser His Ile Leu Pro Ser Phe Gly Leu Pro Thr
1               5                   10                  15

Phe Asn

<210> SEQ ID NO 46
```

```
<211> LENGTH: 18
<212> TYPE: PRT
<213> ORGANISM: Artificial
<220> FEATURE:
<223> OTHER INFORMATION: Peptide linker.

<400> SEQUENCE: 46

Arg Pro Val Ser Pro Phe Thr Phe Pro Arg Leu Ser Asn Ser Trp Leu
1               5                   10                  15

Pro Ala

<210> SEQ ID NO 47
<211> LENGTH: 18
<212> TYPE: PRT
<213> ORGANISM: Artificial
<220> FEATURE:
<223> OTHER INFORMATION: Peptide linker.

<400> SEQUENCE: 47

Ser Pro Ala Ala His Phe Pro Arg Ser Ile Pro Arg Pro Gly Pro Ile
1               5                   10                  15

Arg Thr

<210> SEQ ID NO 48
<211> LENGTH: 18
<212> TYPE: PRT
<213> ORGANISM: Artificial
<220> FEATURE:
<223> OTHER INFORMATION: Peptide linker.

<400> SEQUENCE: 48

Ala Pro Gly Pro Ser Ala Pro Ser His Arg Ser Leu Pro Ser Arg Ala
1               5                   10                  15

Phe Gly

<210> SEQ ID NO 49
<211> LENGTH: 18
<212> TYPE: PRT
<213> ORGANISM: Artificial
<220> FEATURE:
<223> OTHER INFORMATION: Peptide linker.

<400> SEQUENCE: 49

Pro Arg Asn Ser Ile His Phe Leu His Pro Leu Leu Val Ala Pro Leu
1               5                   10                  15

Gly Ala

<210> SEQ ID NO 50
<211> LENGTH: 18
<212> TYPE: PRT
<213> ORGANISM: Artificial
<220> FEATURE:
<223> OTHER INFORMATION: Peptide linker.

<400> SEQUENCE: 50

Met Pro Ser Leu Ser Gly Val Leu Gln Val Arg Tyr Leu Ser Pro Pro
1               5                   10                  15

Asp Leu

<210> SEQ ID NO 51
<211> LENGTH: 18
<212> TYPE: PRT
<213> ORGANISM: Artificial
<220> FEATURE:
```

<223> OTHER INFORMATION: Peptide linker.

<400> SEQUENCE: 51

Ser Pro Gln Tyr Pro Ser Pro Leu Thr Leu Thr Leu Pro Pro His Pro
1               5                   10                  15

Ser Leu

<210> SEQ ID NO 52
<211> LENGTH: 18
<212> TYPE: PRT
<213> ORGANISM: Artificial
<220> FEATURE:
<223> OTHER INFORMATION: Peptide linker.

<400> SEQUENCE: 52

Asn Pro Ser Leu Asn Pro Pro Ser Tyr Leu His Arg Ala Pro Ser Arg
1               5                   10                  15

Ile Ser

<210> SEQ ID NO 53
<211> LENGTH: 17
<212> TYPE: PRT
<213> ORGANISM: Artificial
<220> FEATURE:
<223> OTHER INFORMATION: Peptide linker.

<400> SEQUENCE: 53

Leu Pro Trp Arg Thr Ser Leu Leu Pro Ser Leu Pro Leu Arg Arg Arg
1               5                   10                  15

Pro

<210> SEQ ID NO 54
<211> LENGTH: 18
<212> TYPE: PRT
<213> ORGANISM: Artificial
<220> FEATURE:
<223> OTHER INFORMATION: Peptide linker.

<400> SEQUENCE: 54

Pro Pro Leu Phe Ala Lys Gly Pro Val Gly Leu Leu Ser Arg Ser Phe
1               5                   10                  15

Pro Pro

<210> SEQ ID NO 55
<211> LENGTH: 18
<212> TYPE: PRT
<213> ORGANISM: Artificial
<220> FEATURE:
<223> OTHER INFORMATION: Peptide linker.

<400> SEQUENCE: 55

Val Pro Pro Ala Pro Val Val Ser Leu Arg Ser Ala His Ala Arg Pro
1               5                   10                  15

Pro Tyr

<210> SEQ ID NO 56
<211> LENGTH: 17
<212> TYPE: PRT
<213> ORGANISM: Artificial
<220> FEATURE:
<223> OTHER INFORMATION: Peptide linker.

<400> SEQUENCE: 56

```
Leu Arg Pro Thr Pro Pro Arg Val Arg Ser Tyr Thr Cys Cys Pro Thr
1               5                   10                  15

Pro

<210> SEQ ID NO 57
<211> LENGTH: 18
<212> TYPE: PRT
<213> ORGANISM: Artificial
<220> FEATURE:
<223> OTHER INFORMATION: Peptide linker.

<400> SEQUENCE: 57

Pro Asn Val Ala His Val Leu Pro Leu Leu Thr Val Pro Trp Asp Asn
1               5                   10                  15

Leu Arg

<210> SEQ ID NO 58
<211> LENGTH: 18
<212> TYPE: PRT
<213> ORGANISM: Artificial
<220> FEATURE:
<223> OTHER INFORMATION: Peptide linker.

<400> SEQUENCE: 58

Cys Asn Pro Leu Leu Pro Leu Cys Ala Arg Ser Pro Ala Val Arg Thr
1               5                   10                  15

Phe Pro

<210> SEQ ID NO 59
<211> LENGTH: 28
<212> TYPE: DNA
<213> ORGANISM: Artificial
<220> FEATURE:
<223> OTHER INFORMATION: PCR primer.

<400> SEQUENCE: 59
cgcggatcct gtgacctgcc tcagactc                                          28

<210> SEQ ID NO 60
<211> LENGTH: 31
<212> TYPE: DNA
<213> ORGANISM: Artificial
<220> FEATURE:
<223> OTHER INFORMATION: PCR primer.

<400> SEQUENCE: 60
gctctagatc atttctcttc tctcagtctt c                                      31

<210> SEQ ID NO 61
<211> LENGTH: 15
<212> TYPE: PRT
<213> ORGANISM: Artificial
<220> FEATURE:
<223> OTHER INFORMATION: Peptide linker.

<400> SEQUENCE: 61

Gly Gly Gly Gly Ser Gly Gly Gly Ser Gly Gly Gly Gly Ser
1               5                   10                  15

<210> SEQ ID NO 62
<211> LENGTH: 6
<212> TYPE: PRT
<213> ORGANISM: Artificial
<220> FEATURE:
<223> OTHER INFORMATION: Peptide linker
```

```
<400> SEQUENCE: 62

Ser Gly Gly Gly Gly Ser
1               5

<210> SEQ ID NO 63
<211> LENGTH: 14
<212> TYPE: PRT
<213> ORGANISM: artificial
<220> FEATURE:
<223> OTHER INFORMATION: Peptide linker

<400> SEQUENCE: 63

Ala Glu Ala Ala Ala Lys Glu Ala Ala Ala Lys Ala Gly Ser
1               5                   10
```

INTERFERON-ANTIBODY FUSION PROTEINS DEMONSTRATING POTENT APOPTOTIC AND ANTI-TUMOR ACTIVITIES

CROSS-REFERENCE TO RELATED APPLICATIONS

This application is a 371 National Phase of PCT/US2008/077074, filed on Sep. 19, 2008, which claims priority to and benefit of U.S. Ser. No. 60/994,717, filed on Sep. 21, 2007, both of which are incorporated herein by reference in their entirety for all purposes.

STATEMENT OF GOVERNMENTAL SUPPORT

This invention was made with Government support under Grant No. CA087990, awarded by the National Institutes of Health. The Government has rights in the invention.

FIELD OF THE INVENTION

This invention pertains to the field of oncology. Chimeric constructs are provided that have significant anti-cancer activity.

BACKGROUND OF THE INVENTION

Although spontaneous immune responses against tumor-associated antigens (TAAs) (Hrouda et al. (1999) *Semin. Oncol.* 26: 455-471) can be detected (Disis et al. (1997) *J. Clin. Oncol.* 15: 3363-3367), malignant cells causing disease fail to elicit an immune response that leads to rejection. Many studies have demonstrated that it is possible to enhance the immunogenicity of tumor cells by introducing immunostimulatory molecules such as cytokines and costimulatory molecules into them (Dranoff and Mulligan (1995) *Adv. Immunol.* 58: 417-454; Hrouda et al. (1999) *Semin. Oncol.* 26: 455-471; Hurford et al. (1995) *Nat. Genet.* 10: 430-435); however, effective gene transfer still remains a challenge. In addition, eradication of residual cancer cells may require the targeting of widely scattered micrometastatic tumor deposits that are not accessible to direct gene transfer.

Both the innate and the adaptive immune responses are essential for providing protection against infectious pathogens and tumors. The cross-talk between innate and adaptive immunity is regulated by interactions between cells and cytokines. Cytokines produced by cells of the innate immune system can, directly or indirectly, activate the cells of the adaptive immune response and can play an important role in eliciting protective antitumor immunity (Belardelli and Ferrantini (2002) *Trends Immunol.* 23: 201-208). Central to the activation of the innate immune system is the detection of bacterial products or "danger" signals that lead to the release of proinflammatory cytokines, such as IFN-α, TNF-α, and IL-1.

IFN-α is a proinflammatory cytokine with potent antiviral and immunomodulatory activities and is a stimulator of differentiation and activity of dendritic cells (DCs) (Santini et al. (2000) *J. Exp. Med.* 191: 1777-1788). Type I IFNs (IFN-α and IFN-β) have multiple effects on the immune response (Theofilopoulos et al. (2005) *Annu. Rev. Immunol.* 23: 307-336). IFN-α plays a role in the differentiation of Th1 cells (Finkelman et al. (1991) *J. Exp. Med.* 174: 1179-1188) and the long-term survival of CD8+ T cells in response to specific antigens (Tough et al. (1996) *Science* 272: 1947-1950).

Multiple studies have shown that IFNs are also capable of exerting antitumor effects in both animal models (Ferrantini et al. (1994) *J. Immunol.* 153: 4604-4615) and cancer patients (14. Gutterman et al. (1980) *Ann. Intern. Med.* 93: 399-406). In addition to enhancing the adaptive antitumor immune response, IFN-α can increase expression of the tumor suppressor gene P53 (Takaoka et al. (2003) *Nature* 424: 516-523), inhibit angiogenesis (Sidky and Borden (1987) *Cancer Res.* 47: 5155-5161), and prime apoptosis (Rodriguez-Villanueva and McDonnell (1995) *Int. J. Cancer* 61: 110-11417) in tumor cells. Although these properties suggest that IFN-α should be an effective therapeutic for the treatment of cancer, its short half-life and systemic toxicity have limited its usage.

SUMMARY OF THE INVENTION

In various embodiments this invention pertains to the discovery that attaching an interferon to a targeting moiety (e.g., a molecule that specifically and/or preferentially binds a marker on or associated with a cell) substantially improves the therapeutic efficacy of the interferon and appears to reduce systemic toxicity. Accordingly, in various embodiments, this invention provides constructs comprising an interferon attached to a targeting moiety and uses of such constructs to specifically and/or preferentially inhibit the growth or proliferation or even to kill certain target cells (e.g., cancer cells).

Accordingly, in certain embodiments, a chimeric construct is provided where the construct comprises an interferon (e.g., interferon-alpha, interferon-beta, interferon-gamma, etc.) attached to a targeting moiety that binds to a tumor associated antigen (TAA), where the construct when contacted to a tumor cell results in the killing or inhibition of growth or proliferation of the tumor cell. In certain embodiments a chimeric construct is provided where the construct comprises an interferon attached to a targeting moiety that binds to a cell surface marker or a cell-associated marker, where the targeting is not attached to the interferon by a (Gly$_4$Ser)$_3$ (SEQ ID NO:31) linker. In various embodiments the interferon is a type 1 interferon. In various embodiments the interferon is a type 2 interferon. In various embodiments the is an interferon alpha, an interferon-beta, or an interferon-gamma. In certain embodiments the targeting moiety is an antibody that binds a tumor associated antigen. In certain embodiments the targeting moiety is chemically coupled to the interferon. In certain embodiments the targeting moiety is joined to the interferon with a peptide linker. In certain embodiments the peptide linker is fewer than 15, fewer than 14, fewer than 12, fewer than 11, fewer than 10, fewer than 9, fewer than 8, fewer than 7, fewer than 6, fewer than 5, fewer than 4, fewer than 3, or fewer than 2 amino acids in length. In certain embodiments the linker is 15, 14, 13, 12, 11, 10, 9, 8, 7, 6, 5, 4, 3, 2, or 1 amino acid in length. In certain embodiments the linker is not (Gly$_4$Ser)$_3$ (SEQ ID NO:31). In certain embodiments the linker is a linker that is resistant or substantially resistant to preoteolysis. In certain embodiments the peptide linker is Gly$_4$Ser (SEQ ID NO:32). In certain embodiments the linker comprises or consists of an amino acid sequence found in Table 2. In certain embodiments the construct is a recombinantly expressed fusion protein. In certain embodiments the antibody specifically binds a marker selected from the group consisting of EGFR, HER4, HER3, HER2/neu, MUC-1, G250, mesothelin, gp100, tyrosinase, and MAGE. In certain embodiments the targeting moiety is an antibody that binds CD20. In certain embodiments the targeting moiety is a single chain antibody that comprises the CDRS and/or the variable regions from an antibody selected from the group consisting of anti-CD20 (Rituximab), Ibritumomab tiuxetan, tositumomab, AME-133v, Ocrelizumab, Ofatumumab, TRU-015, IMMU-106, and the like. In various embodiments the targeting moiety is an antibody that binds HER2. In certain embodiments the antibody is a C6 antibody. In certain embodiments the antibody comprises the VH and VL CDRs or VH and VL domains of C6MH3-B1. In various embodiments the antibody is an IgG (e.g., IgG1, IgG3, etc.), an IgE, a single chain Fv (scFv), a FAB, a (Fab')$_2$, an (ScFv)$_2$, and the like. In certain embodiments the antibody is an antibody selected form the group consisting of Rituxan, IF5, B1, 1H4, CD19, B4, B43, FVS191, hLL2, LL2, RFB4, M195, HuM195, AT13/5, HERCEPTIN®, 4D5, HuCC49, HUCC39ΔCH2 B72.3, 12C10, IG5, H23, BM-2, BM-7, 12H12, MAM-6, and HMFG-1. In certain embodiments the antibody is an antibody that binds a member of the EGF receptor family. In certain embodiments the antibody is selected from the group consisting of C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4. B6, HER4.D4, HER4.D7, HER4.D11, HER4.D12, HER4.E3, HER4.E7, HER4.F8 and HER4.C7. In certain embodiments the construct comprises an anti-HER2 IgG1 antibody attached to an interferon.

Also provided are pharmaceutical formulations. In various embodiments the formulations comprise a chimeric construct comprising an interferon attached to a targeting moiety. In certain embodiments the chimeric construct comprises a construct as described above (and/or herein below) (e.g., an anti-CD20-Interferon, and anti-HER2-interferon, etc.). In certain embodiments the formulation is a unit dosage formulation. In certain embodiments the formulation is a formulated for parenteral administration. In certain embodiments the formulation is a formulated for administration via a route selected from the group consisting of oral administration, intravenous administration, intramuscular administration, direct tumor administration, inhalation, rectal administration, vaginal administration, transdermal administration, and subcutaneous depot administration.

In various embodiments methods are provided for inhibiting growth and/or proliferation of a cancer cell. The methods typically involve contacting the cancer cell with a chimeric construct as described herein. In certain embodiments the cancer cell is a metastatic cell, and/or a cell is in a solid tumor. In certain embodiments the cancer cell is a breast cancer cell. In certain embodiments the cancer cell is a B cell lymphoma. In certain embodiments the cancer cell is cell produced by a cancer selected from the group consisting of a B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma. In various embodiments the contacting comprises systemically administering the chimeric moiety to a mammal. In certain embodiments the contacting comprises administering the chimeric moiety directly into a tumor site. In certain embodiments the contacting comprises intravenous administration of the chimeric moiety. In certain embodiments the cancer cell is a cancer cell in a human or in a non-human mammal.

In certain embodiments nucleic acids are provided that encode the chimeric constructs described herein. In various embodiments the nucleic acid encodes a fusion protein comprising an interferon attached to an anti-EGFR family member antibody, an anti-HER2 antibody, an anti-C6 single-chain antibody, or to an anti-CD20 single chain antibody. In various embodiments the interferon encoded by the nucleic acid is a type I interferon. In certain embodiments the interferon is IFN-α or interferon-β. In various embodiments the nucleic encodes an antibody that comprises the VH and VL CDRs of C6MH3-B1. In various embodiments nucleic acid encodes a peptide linker (e.g., as described herein) attaching the antibody to the interferon. In certain embodiments the nucleic acid encodes the CDRs and/or the variable regions for anti-CD20 (Rituximab).

Also provided is a cell comprising a nucleic as described above, that encodes a chimeric construct. In certain embodiments the cell expresses the chimeric construct.

In various embodiments this invention provides the use of a chimeric construct as described herein in the manufacture of a medicament to inhibit the growth and/or proliferation of a cancer cell.

In certain embodiments, the methods and constructs of this invention specifically exclude constructs using any of the antibodies disclosed in U.S. Patent Publication No: US 2002/0193569 A1. In certain embodiments the methods and constructs of this invention specifically exclude constructs incorporating an anti-CD20 antibody. In certain embodiments the methods and constructs of this invention specifically exclude constructs incorporating antibodies that bind to any of the following targets: CD19, CD20, CD22, CD33, CD38, EGFR, HM1.24, phosphatidyl serine antigen, HER-2, TAG-72, and/or MUC-1. In certain embodiments the constructs described herein can be used in the treatment of pathologies such as multiple sclerosis, HCV mediated vasculitis, and the like.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively.

Antibodies exist as intact immunoglobulins or as a number of well characterized fragments produced by digestion with various peptidases or expressed de novo. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, IgE, scFv, dAb, nanobodies, unibodies, and diabodies. In various embodiments preferred antibodies include, but are not limited to Fab'$_2$, IgG, IgM, IgA, IgE, and single chain antibodies, more preferably single chain Fv (scFv) antibodies in which a variable heavy and a variable light chain are joined together (directly or through a peptide linker) to form a continuous polypeptide.

In certain embodiments antibodies and fragments used in the constructs of the present invention can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) *Proc. Natl. Acad. Sci., USA,* 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest,* 4th ed. U.S. Dept. Health and Human Services, Public Health Services, Bethesda, Md. (1987).

The term "interferon" refers to a full-length interferon or to an interferon fragment (truncated interferon) or interferon mutant, that substantially retains the biological activity of the full length wild-type interferon (e.g., retains at least 80%, preferably at least 90%, more preferably at least 95%, 98%, or 99% of the full-length antibody). Interferons include type I interferons (e.g., interferon-alpha and interferon-beta) as well as type II inteferons (e.g., interferon-gamma). The interferon (e.g., IFN-α) can be from essentially any mammalian species. In certain preferred embodiments, the interferon is from a species selected from the group consisting of human, equine, bovine, rodent, porcine, lagomorph, feline, canine, murine, caprine, ovine, a non-human primate, and the like. In various embodiments the mutated interferon comprises one or more amino acid substitutions, insertions, and/or deletions.

An anti-HER2/neu antibody is an antibody that specifically or preferentially binds a HER2/neu receptor.

As used herein, the term "subject" refers to a human or non-human animal, including, but not limited to, a cat, dog, horse, pig, cow, sheep, goat, rabbit, mouse, rat, or monkey.

The term "C6 antibody", as used herein refers to antibodies derived from C6.5 whose sequence is expressly provided, for example, in U.S. Pat. Nos. 6,512,097 and 5,977,322, and in PCT Publication WO 97/00271. C6 antibodies preferably have a binding affinity of about $1.6 \times 10^{-8}$ or better for HER2/neu. In certain embodiments C6 antibodies are derived by screening (for affinity to c-erbB-2/HER2/neu) a phage display library in which a known C6 variable heavy ($V_H$) chain is expressed in combination with a multiplicity of variable light ($V_L$) chains or conversely a known C6 variable light chain is expressed in combination with a multiplicity of variable heavy ($V_H$) chains. C6 antibodies also include those antibodies produced by the introduction of mutations into the variable heavy or variable light complementarity determining regions (CDR1, CDR2 or CDR3), e.g., as described in U.S. Pat. Nos. 6,512,097 and 5,977,322, and in PCT Publication WO 97/00271. In addition, C6 antibodies include those antibodies produced by any combination of these modification methods as applied to C6.5 and its derivatives.

An "anti-EGFR family antibody" refers to an antibody that specifically binds to a member of the epidermal growth factor receptor family (e.g., an antibody that binds to ErbB-1, also named epidermal growth factor receptor (EGFR), ErbB-2, also named HER2 in humans and neu in rodents, ErbB-3, also named HER3, and/or to ErbB-4, also named HER4). Illustrative anti-EGFR family antibodies include, but are not limited to antibodies such as C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7 and the like (see, e.g., U.S. Patent publications US 2006/0099205 A1 and US 2004/0071696 A1 which are incorporated herein by reference).

A single chain Fv ("sFv" or "scFv") polypeptide is a covalently linked $V_H$:$V_L$ heterodimer which, in certain embodiments, may be expressed from a nucleic acid including $V_H$- and $V_L$-encoding sequences either joined directly or joined by a peptide-encoding linker. Huston, et al. *Proc. Nat. Acad. Sci. USA*, 85: 5879-5883 (1988). A number of structures for converting the naturally aggregated, but chemically separated light and heavy polypeptide chains from an antibody V region into an sFv molecule that will fold into a three dimensional structure substantially similar to the structure of an antigen-binding site. See, e.g. U.S. Pat. Nos. 5,091,513 and 5,132,405, and 4,956,778.

"CD20" is a non-glycosylated phosphoprotein expressed on the surface of mature B-cells (see, e.g., Cragg et al. (2005) *Curr. Dir. Autoimmun.*, 8: 140-174). It is also found on B-cell lymphomas, hairy cell leukemia, B-cell chronic lymphocytic leukemia, on skin/melanoma cancer stem cells, and the like.

The phrase "inhibition of growth and/or proliferation" of a cancer cell refers to decrease in the growth rate and/or proliferation rate of a cancer cell. In certain embodiments this includes death of a cancer cell (e.g. via apoptosis). In certain embodiments this term also refers to inhibiting the growth and/or proliferation of a solid tumor and/or inducing tumor size reduction or elimination of the tumor.

The term "cancer marker" refers to biomolecules such as proteins, carbohydrates, glycoproteins, and the like that are exclusively or preferentially or differentially expressed on a cancer cell and/or are found in association with a cancer cell and thereby provide targets preferential or specific to the cancer. In various embodiments the preferential expression can be preferential expression as compared to any other cell in the organism, or preferential expression within a particular area of the organism (e.g. within a particular organ or tissue).

BRIEF DESCRIPTION OF THE DRAWINGS

FIGS. 1A-1o show the nucleic acid and amino acid sequences for various constructs described herein. FIG. 1A shows amino acid sequences for anti-HER2/neu IgG3heavy chain-IFN-α (SEQ ID NO:1) and anti-HER2/neu IgG3 light chain (SEQ ID NO:2). Single underline is linker, double underline is murine IFN-α, no underline is anti-HER2/neu. FIG. 1B: αCD20 light chain, nucleic acid (SEQ ID NO:3), amino acid sequence (SEQ ID NO:4); FIG. 1C: αCD20-IgG3-muIFNα Gly₄Ser linker, nucleic acid (SEQ ID NO:5), amino acid sequence (SEQ ID NO:6); FIG. 1D: αCD20-IgG3-muIFNα alpha helical linker, nucleic acid (SEQ ID NO:7), amino acid sequence (SEQ ID NO:8); FIG. 1E: αCD20-IgG3-huIFNα Gly₄Ser linker, nucleic acid (SEQ ID NO:9), amino acid sequence (SEQ ID NO:10); FIG. 1F: αCD20-IgG3-huIFNα alpha helical linker, nucleic acid (SEQ ID NO:11), amino acid sequence (SEQ ID NO:12); FIG. 1G: αCD20-IgG1-muIFNα Gly₄Ser linker, nucleic acid (SEQ ID NO:13), amino acid sequence (SEQ ID NO:14); FIG. 1H: αCD20-IgG1-muIFNα alpha helical linker, nucleic acid (SEQ ID NO:15), amino acid sequence (SEQ ID NO:16); FIG. 1I: αCD20-IgG1-huIFNα Gly₄Ser linker, nucleic acid (SEQ ID NO:17), amino acid sequence (SEQ ID NO:18); FIG. 1J: αCD20-IgG1-huIFNα alpha helical linker, nucleic acid (SEQ ID NO:19), amino acid sequence (SEQ ID NO:20); FIG. 1K: αHer2/neu light chain nucleic acid (SEQ ID NO:21), amino acid sequence (SEQ ID NO:22); FIG. 1L: αHer2/neu-IgG1-muIFNα glyser linker nucleic acid sequence (SEQ ID NO:23), amino acid sequence (SEQ ID NO:24); FIG. 1M: αHer2/neu-IgG1-muIFNα alpha helical linker nucleic acid sequence (SEQ ID NO:25), amino acid sequence (SEQ ID NO:26); FIG. 1N: αHer2/neu-IgG1-huIFNα glyser linker nucleic acid sequence (SEQ ID NO:27), amino acid sequence (SEQ ID NO:28); FIG. 1o: αHer2/neu-IgG1-huIFNα alpha helical linker nucleic acid sequence (SEQ ID NO:29), amino acid sequence (SEQ ID NO:30). It will be appreciated that while the constructs in this figure are shown with particular linkers, in certain embodiments other linkers can be substituted therefore as described herein.

FIG. 2A: Schematic diagram of anti-HER2/neu-IgG3-IFN-α. Solid areas represent anti-HER2/neu variable regions. Open areas represent human IgG3 and κ constant regions. White circle regions represent murine IFN-α. FIG. 2B: SDS-PAGE of purified anti-HER2/neu-IgG3 (lanes 1 and 4), IgG3-IFN-α (lanes 2 and 5), and anti-HER2/neu-IgG3-IFN-α (lanes 3 and 6) under nonreducing (lanes 1-3) or reducing (lanes 4-6) conditions. The molecular mass marker proteins are shown at the left of each gel. FIG. 2C: Anti-HER2/neu-IgG3 and anti-HER2/neu-IgG3-IFN-α bind HER2/neu. CT26/HER2, a murine colonic cell line expressing high levels of human HER2/neu, was reacted with anti-HER2/neu-IgG3, IgG3-IFN-α, or anti-HER2/neu-IgG3-IFN-α with or without heparin followed by PE-labeled rabbit anti-human IgG. Dashed lines represent signal from cells without addition of recombinant protein. FIG. 2D: The protective activity of the IFN-α standard and different IFN-α fusion proteins against VSV. Dilutions of 1 U of IFN-α standard, 0.21 ng (10 pM) of anti-HER2/neu-IgG3-IFN-α, 0.21 ng (10 pM) of IgG3-IFN-α, or 0.17 ng (10 pM) of anti-HER2/neu-IgG3 in 100 µl were prepared and added to L-929 cells. After a 24-h incubation, 4000 PFU of VSV were added. Forty-eight hours later, viable cells were stained with crystal violet dye, dissolved by methanol, and solubilized dye was detected using an ELISA reader at 570 nm.

FIG. 4A: Mice were treated with 9600 U of rIFN-α or 9600 U (4 µg) of IgG3-IFN-α at days 1 and 3 after tumor challenge. Animals were followed for survival and sacrificed when the diameter of the s.c. tumor reached 15 mm. FIG. 4B: Groups of three C3H/HeN mice were injected i.p. with 66 µCi of ¹²⁵I-labeled rIFN-α, IgG3-IFN-α or, anti-HER2/neu-IgG3-IFN-α. At various intervals after injection of the ¹²⁵I-labeled proteins, residual radioactivity was measured using a mouse whole body counter. The results represent the mean of three mice. Bars, SD.

FIG. 5C: IFN-α fusion proteins induce apoptosis in 38C13/HER2 cells. In brief, 1×10⁶ 38C13/HER2 cells were incubated with 1 nM of the indicated proteins for 72 h. The cells were then washed, stained with Alexa Fluor 488, annexin V, and PI and were analyzed by flow cytometry. The percentage of cells located in each quadrant is indicated at the corner. FIG. 5D: IFN-α fusion proteins inhibited proliferation of surviving 38C13/HER2 cells. In brief, 1×10⁶ 38C13/HER2 cells were labeled with 2.5 µM CFSE and immediately fixed (dash line), or treated with PBS (thin black line), or 1 nM of either anti-HER2/neu IgG3 (thin black line, overlaps with PBS control), IgG3-IFN-α (thick black line), or anti-HER2/neu-IgG3-IFN-α (black area) for 48 h. The cells were then washed and analyzed by flow cytometry. The histogram was obtained by gating on the population of live cells.

FIG. 6C: The intensity of antiphosphoSTAT1 was normalized with the intensity of anti-GAPDH for each indicated time point, and the values obtained were divided by the value at time 0 to obtain the fold activation for STAT1. These experiments were performed twice; error bars, SD of the measurements. *, Only point where the two groups differ with a p<0.05.

FIG. 10 shows SDS-PAGE analysis of fractions eluted from protein A Sepharose. Culture supernatants from cells expressing anti-CD-20-IgG3-IFNa with the (Gly₄Ser)₃ (SEQ ID NO:31) linker were passed through the protein A Sepharose and the fusion protein bound prior to elution. A. Proteins were run without reduction. Lane 1, IgG3; Lanes 2-6, fractions eluted from protein A Sepharose. B. Proteins were reduced prior to analysis. Lane 2, IgG3; Lanes 3-7, fractions eluted from protein A Sepharose.

FIG. 21. Daudi cells were incubated with 72 hours with 1 pM of anti-CD20-IgG3-hIFNα with the Gly₄Ser linker (32) (Gly-Ser Linker) or with 1 pM of anti-CD20-IgG3-hIFNα with the alpha helical linker (Alpha helix Linker). Cell viability and apoptosis was determined following staining with Annexin V and PI and analysis by FLOW cytometry.

FIG. 22 shows survival of mice inoculated with 5000 38C13-CD20 cells and treated on days 1, 2 and 3 with HBSS or the indicated amounts of the anti-CD20-IFN-α fusion proteins.

DETAILED DESCRIPTION

Figure 2A:
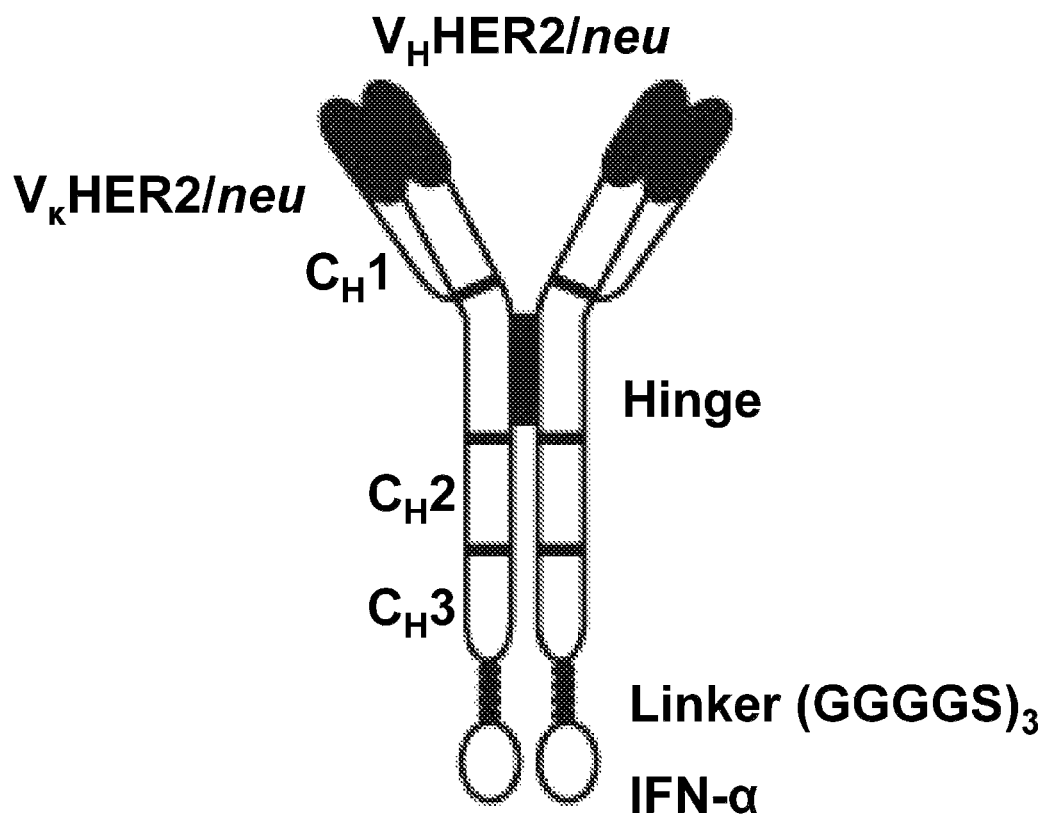
FIGS. 2A, 2B, 2C, and 2D illustrate the construction and characterization of anti-HER2/neu IgG3-IFN-α.

Interferon alpha (IFN-α) is an important cytokine in initiating the innate immune response and also demonstrates a wide spectrum of anti-tumor activities. The clinical use of interferon (e.g., IFN-α) as an anticancer drug, however, is hampered by its short half-life, which significantly compromises its therapeutic effect. In certain embodiments this invention pertains to the discovery that the therapeutic index of interferon can be improved by attaching the interferon to a targeting moiety that specifically/preferentially binds a marker on or associated with the target cell (e.g., a tumor cell). This permits the deliver of higher doses of interferon to the target site with fewer systemic complications. This was illustrated, in one embodiment, by the construction and use of a fusion protein consisting of an anti-HER2/neu IgG3 and IFN-α (anti-HER2/neu-IgG3-IFN-α) and in another embodiment by the construction and use of an anti-CD20-IFN-α fusion protein.

The efficacy of the HER2/neu-IgG3-IFN-α constructs was tested on a murine B-cell lymphoma, 38C13, transduced with human HER2/neu. The anti-HER2/neu-IgG3-IFN-α fusion protein exhibited a potent effect in inhibiting the 38C13/HER2 tumor growth in vivo, and even administration of 1 μg anti-HER2/neu IgG3-IFN-α resulted in 88% of long-term survivors after tumor challenge.

Remarkably, Anti-HER2/neu IgG3-IFN-α demonstrated a potent activity against established 38C13/HER2 tumors, and complete tumor remission was observed in 88% treated mice. This dramatic anti-tumor activity was mediated by IFN-α induced apoptosis and targeting IFN-α to 38C13/HER2 tumor cells by the anti-HER2/neu IgG3 antibody was essential to potentiate these effects.

Similar results were observed for the anti-CD20-IgG3-IFN-α construct (see, Example 2). These results indicate that attachment (e.g., fusion) of an interferon (e.g., IFN-α) to a targeting moiety (e.g., to a tumor specific antibody) produces an effective therapeutic that can be used to inhibit the growth and/or proliferation or even to kill target cell(s). Thus, for example, the exemplary constructs described herein can readily be used for treatment of B cell lymphoma and other cancers in clinic.

Thus, in certain embodiments, this invention provides constructs (e.g., chimeric moieties) comprising an interferon (e.g., IFN-α) attached to a targeting moiety (e.g., to an antibody that specifically binds a cancer specific marker on a cancer cell). The constructs include chemical conjugates as well as fusion proteins. Also provided are nucleic acids encoding the fusion proteins as well as cells transfected with the nucleic acids to express the fusion proteins. Also provided are methods of inhibiting growth and proliferation of cancer cells as well as kits comprising, e.g. the chimeric moieties described herein, for the treatment of various cancers.

I. Chimeric Constructs Comprising a Targeting Moiety Attached to an Interferon.

It was a surprising discovery that chimeric constructs comprising a targeting moiety (e.g., an anti-tumor marker antibody) attached to a native (wildtype) or modified IFN (e.g., IFN-α) can be effectively used to inhibit the growth and/or proliferation of target cancer cells expressing or associated with the marker to which the targeting moiety is directed. In certain embodiments the targeting moieties are chemically conjugated to the interferon, while in other embodiments, the targeting moiety is expressed as a fusion protein with the IFN-α. When produced as a fusion protein the targeting moiety (e.g., antibody) component can be directly fused to the IFN-α or attached by means of a peptide linker (e.g., a (Gly$_4$Ser)$_3$ (SEQ ID NO:31) linker, a GlyGlyGlyGlySer (SEQ ID NO:32) linker, a AEAAAKEAAAKA (SEQ ID NO:33), and the like.

A) Targeting Moieties.

In various embodiments, the targeting moiety is a molecule that specifically or preferentially binds a marker expressed by (e.g., on the surface of) or associated with the target cell(s). While essentially any cell can be targeted, certain preferred cells include those associated with a pathology characterized by hyperproliferation of a cell (i.e., a hyperproliferative disorder). Illustrative hyperproliferative disorders include, but are not limited to psoriasis, neutrophilia, polycythemia, thrombocytosis, and cancer.

Hyperproliferative disorders characterized as cancer include but are not limited to solid tumors, such as cancers of the breast, respiratory tract, brain, reproductive organs, digestive tract, urinary tract, eye, liver, skin, head and neck, thyroid, parathyroid and their distant metastases. These disorders also include lymphomas, sarcomas, and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophtalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

In certain embodiments, the targeting moiety is a moiety that binds a cancer marker (e.g., a tumor associated antigen). A wide variety of cancer markers are known to those of skill in the art. The markers need not be unique to cancer cells, but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention*, 22(2): 147-152). Other important targets for cancer immunotherapy are membrane bound complement regulatory glycoprotein: CD46, CD55 and CD59, which have been found to be expressed on most tumor cells in vivo and in vitro. Human mucins (e.g. MUC1) are known tumor markers as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HMB 45 marker. Non-hodgkins lymphomas have been characterized by the CD20, CD19, and Ia marker. And various prostate cancers have been characterized by the PSMA and SE10 markers.

In addition, many kinds of tumor cells display unusual antigens that are either inappropriate for the cell type and/or its environment, or are only normally present during the organisms' development (e.g. fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells display cell surface receptors that are rare or absent on the surfaces of healthy cells, and which are responsible for activating cellular signaling pathways that cause the unregulated growth and division of the tumor cell. Examples include (ErbB2). HER2/neu, a constitutively active cell surface receptor that is produced at abnormally high levels on the surface of breast cancer tumor cells.

Other useful targets include, but are not limited to CD20, CD52, CD33, epidermal growth factor receptor and the like.

An illustrative, but not limiting list of suitable tumor markers is provided in Table 1. Antibodies to these and other cancer markers are known to those of skill in the art and can be obtained commercially or readily produced, e.g. using phage-display technology.

TABLE 1

Illustrative cancer markers and associated references, all of which are incorporated herein by reference for the purpose of identifying the referenced tumor markers.

| Marker | Reference |
| --- | --- |
| 5 alpha reductase | Délos et al. (1998) *Int J Cancer*, 75: 6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmannet al. (1997) *Oncol Res.*, 9(3) 119-127 |
| APRIL | Sordat et al. ('998) *J Exp Med.*, 188(6): 1185-1190 |
| BAGE | Böel et al. (1995) *Immunity*, 2: 167-175. |
| β-catenin | Hugh et al. (1999) *Int J Cancer*, 82(4): 504-11 |
| Bcl2 | Koty et al. (1999) *Lung Cancer*, 23(2): 115-127 |
| bcr-ab1 (b3a2) | Verfaillie et al.(´996) *Blood*, 87(11): 4770-4779 |
| CA-125 | Bast et al. (´998) *Int J Biol Markers*, 13(4): 179-187 |
| CASP-8/FLICE | Mandruzzato et al. (1997) *J Exp Med.*, 186(5): 785-793. |
| Cathepsins | Thomssen et al.(1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et al. (1997) *Leuk Lymphoma*, 25(5-6): 521-530 |
| CD22, CD38 | French et al. (1995) *Br J Cancer*, 71(5): 986-994 |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et al. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |

TABLE 1-continued

Illustrative cancer markers and associated references, all of which are incorporated herein by reference for the purpose of identifying the referenced tumor markers.

| Marker | Reference |
| --- | --- |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al.(1998) *Urol Res.*, 26(4): 259-264 |
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al.(1996) *Melanoma Res.*, 6(1): 11-24 |
| gp75/TRP-1 | Lewis et al.(1995) *Semin Cancer Biol.*, 6(6): 321-327 |
| hCG | Hoermann et al. (1992) *Cancer Res.*, 52(6): 1520-1524 |
| Heparanase | Vlodaysky et al. (1999) *Nat Med.*, 5(7): 793-802 |
| Her2/neu | Lewis et al. (1995) *Semin Cancer Biol.*, 6(6): 321-327 |
| Her3 | |
| HMTV | Kahl et al.(1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer*, 80(2): 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/ MART-1 | Lewis and Houghton (1995) *Semin Cancer Biol.*, 6(6): 321-327 |
| mesothelin | Chang et al. (1996) *Proc. Natl. Acad. Sci.*, USA, 93(1): 136-140 |
| MIC A/B | Groh et al.(1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J. Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |
| p53 | Roth et al. (1996) *Proc. Natl. Acad. Sci.*, USA, 93(10): 4781-4786. |
| p97/melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |
| Progenipoietin | — |
| PSA | Sanda et al. (1999) *Urology*, 53(2): 260-266. |
| PSM | Kawakami et al.(1997) *Cancer Res.*, 57(12): 2321-2324 |
| RAGE-1 | Gaugler et al.(1996) *Immunogenetics*, 44(5): 323-330 |
| Rb | Dosaka-Akita et al. (1997) *Cancer*, 79(7): 1329-1337 |
| RCAS1 | Sonoda et al.(1996) *Cancer*, 77(8): 1501-1509. |
| SART-1 | Kikuchi et al.(1999(*Int J Cancer*, 81(3): 459-466 |
| SSX gene family | Gure et al. (1997) *Int J Cancer*, 72(6): 965-971 |
| STAT3 | Bromberg et al. (1999) *Cell*, 98(3): 295-303 |
| STn (mucin assoc.) | Sandmaier et al. (1999) *J Immunother.*, 22(1): 54-66 |
| TAG-72 | Kuroki et al. (1990) *Cancer Res.*, 50(16): 4872-4879 |
| TGF-α | Imanishi et al. (1989) *Br J Cancer*, 59(5): 761-765 |
| TGF-β | Picon et al. (1998) *Cancer Epidemiol Biomarkers Prev*, 7(6): 497-504 |
| Thymosin β 15 | Bao et al. (1996) *Nature Medicine*. 2(12), 1322-1328 |
| IFN-α | Moradi et al. (1993) *Cancer*, 72(8): 2433-2440 |

TABLE 1-continued

Illustrative cancer markers and associated references, all of which are incorporated herein by reference for the purpose of identifying the referenced tumor markers.

| Marker | Reference |
| --- | --- |
| TPA | Maulard et al. (1994) Cancer, 73(2): 394-398 |
| TPI | Nishida et al.(1984) Cancer Res 44(8): 3324-9 |
| TRP-2 | Parkhurst et al. (1998) Cancer Res., 58(21) 4895-4901 |
| Tyrosinase | Kirkin et al. (1998) APMIS, 106(7): 665-679 |
| VEGF | Hyodo et al. (1998) Eur J Cancer, 34(13): 2041-2045 |
| ZAG | Sanchez et al. (1999) Science, 283(5409): 1914-1919 |
| p16INK4 | Quelle et al. (1995) Oncogene Aug. 17, 1995; 11(4): 635-645 |
| Glutathione S-transferase | Hengstler (1998) et al. Recent Results Cancer Res., 154: 47-85 |

Any of the foregoing markers can be used as targets for the targeting moieties comprising the interferon-targeting moiety constructs of this invention. In certain embodiments the target markers include, but are not limited to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

The foregoing markers are intended to be illustrative and not limiting. Other tumor associated antigens will be known to those of skill in the art.

Where the tumor marker is a cell surface receptor, ligand to that receptor can function as targeting moieties. Similarly mimetics of such ligands can also be used as targeting moieties.

Antibodies.

In certain embodiments, the targeting moieties can comprise antibodies, unibodies, or affybodies that specifically or preferentially bind the tumor marker. Antibodies that specifically or preferentially bind tumor markers are well known to those of skill in the art. Thus, for example, antibodies that bind the CD22 antigen expressed on human B cells include HD6, RFB4, UV22-2, To15, 4KB128, a humanized anti-CD22 antibody (hLL2) (see, e.g., Li et al. (1989) Cell. Immunol. 111: 85-99; Mason et al. (1987) Blood 69: 836-40; Behr et al. (1999) Clin. Cancer Res. 5: 3304s-3314s; Bonardi et al. (1993) Cancer Res. 53: 3015-3021).

Antibodies to CD33 include for example, HuM195 (see, e.g., Kossman et al. (1999) Clin. Cancer Res. 5: 2748-2755), CMA-676 (see, e.g., Sievers et al., (1999) Blood 93: 3678-3684.

Antibodies to CD38 include for example, AT13/5 (see, e.g., Ellis et al. (1995) J. Immunol. 155: 925-937), HB7, and the like.

In certain embodiments the targeting moiety comprises an anti-HER2 antibody. The ergB 2 gene, more commonly known as (Her-2/neu), is an oncogene encoding a transmembrane receptor. Several antibodies have been developed against Her-2/neu, including trastuzumab (e.g., HERCEPTIN®.; Fornier et al. (1999) Oncology (Huntingt) 13: 647-58), TAB-250 (Rosenblum et al. (1999) Clin. Cancer Res. 5: 865-874), BACH-250 (Id.), TA1 (Maier et al. (1991) Cancer Res. 51: 5361-5369), and the mAbs described in U.S. Pat. Nos. 5,772,997; 5,770,195 (mAb 4D5; ATCC CRL 10463); and U.S. Pat. No. 5,677,171

Illustrative anti-MUC-1 antibodies include, but are not limited to Mc5 (see, e.g., Peterson et al. (1997) Cancer Res. 57: 1103-1108; Ozzello et al. (1993) Breast Cancer Res. Treat. 25: 265-276), and hCTMO1 (see, e.g., Van Hof et al. (1996) Cancer Res. 56: 5179-5185).

Illustrative anti-TAG-72 antibodies include, but are not limited to CC49 (see, e.g., Pavlinkova et al. (1999) Clin. Cancer Res. 5: 2613-2619), B72.3 (see, e.g., Divgi et al. (1994) Nucl. Med. Biol. 21: 9-15), and those disclosed in U.S. Pat. No. 5,976,531.

Illustrative anti-HM1.24 antibodies include, but are not limited to a mouse monoclonal anti-HM1.24 IgG$_{2a}$/κ and a a humanized anti-HM1.24 IgG$_1$/κ. antibody (see, e.g., Ono et al. (1999) Mol. Immuno. 36: 387-395).

A number of antibodies have been developed that specifically bind HER2 and some are in clinical use. These include, for example, trastuzumab (e.g., HERCEPTIN®, Fornier et al. (1999) Oncology (Huntingt) 13: 647-658), TAB-250 (Rosenblum et al. (1999) Clin. Cancer Res. 5: 865-874), BACH-250 (Id.), TA1 (see, e.g., Maier et al. (1991) Cancer Res. 51: 5361-5369), and the antibodies described in U.S. Pat. Nos. 5,772,997; 5,770,195, and 5,677,171.

Other fully human anti-HER2/neu antibodies are well known to those of skill in the art. Such antibodies include, but are not limited to the C6 antibodies such as C6.5, DPL5, G98A, C6MH3-B1, B1D2, C6VLB, C6VLD, C6VLE, C6VLF, C6MH3-D7, C6MH3-D6, C6MH3-D5, C6MH3-D3, C6MH3-D2, C6MH3-D1, C6MH3-C4, C6MH3-C3, C6MH3-B9, C6MH3-B5, C6MH3-B48, C6MH3-B47, C6MH3-B46, C6MH3-B43, C6MH3-B41, C6MH3-B39, C6MH3-B34, C6MH3-B33, C6MH3-B31, C6MH3-B27, C6MH3-B25, C6MH3-B21, C6MH3-B20, C6MH3-B2, C6MH3-B16, C6MH3-B15, C6MH3-B11, C6MH3-B1, C6MH3-A3, C6MH3-A2, and C6ML3-9. These and other anti-HER2/neu antibodies are described in U.S. Pat. Nos. 6,512,097 and 5,977,322, in PCT Publication WO 97/00271, in Schier et al. (1996) J Mol Biol 255: 28-43, Schier et al. (1996) J Mol Biol 263: 551-567, and the like.

More generally, antibodies directed to various members of the epidermal growth factor receptor family are well suited for use as targeting moieties in the constructs of the present invention. Such antibodies include, but are not limited to anti-EGF-R antibodies as described in U.S. Pat. Nos. 5,844,093 and 5,558,864, and in European Patent No. 706,799A.). Other illustrative anti-EGFR family antibodies include, but are not limited to antibodies such as C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4. C7 and the like (see, e.g., U.S. Patent publications US 2006/0099205 A1 and US 2004/0071696 A1 which are incorporated herein by reference).

As described in U.S. Pat. Nos. 6,512,097 and 5,977,322 other anti-EGFR family member antibodies can readily be produced by shuffling light and/or heavy chains followed by one or more rounds of affinity selection. Thus in certain embodiments, this invention contemplates the use of one, two, or three CDRs in the VL and/or VH region that are CDRs described in the above-identified antibodies and/or the above identified publications.

In various embodiments the targeting moiety comprises an antibody that specifically or preferentially binds CD20. Anti-CD20 antibodies are well known to those of skill and include, but are not limited to rituximab, Ibritumomab tiuxetan, and tositumomab, AME-133v (Applied Molecular Evolution), Ocrelizumab (Roche), Ofatumumab (Genmab), TRU-015 (Trubion) and IMMU-106 (Immunomedics).

The invention need not be limited to the use of the antibodies described above, and other such antibodies as they are known to those of skill in the art can be used in the compositions and methods described herein.

While the above discussion pertains to antibodies, it will be recognized that affybodies and/or unibodies can be used instead of antibodies.

Unibodies.

UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule left only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

Affibodies.

Affibody molecules are class of affinity proteins based on a 58-amino acid residue protein domain, derived from one of the IgG-binding domains of *staphylococcal* protein A. This three helix bundle domain has been used as a scaffold for the construction of combinatorial phagemid libraries, from which Affibody variants that target the desired molecules can be selected using phage display technology (see, e.g., Nord et al. (1997) *Nat. Biotechnol.* 15: 772-777; Ronmark et al. (2002) *Eur. J. Biochem.,* 269: 2647-2655.). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the construct (e.g., anti-HER2/neu-IFN-α chimera) is to be used. In other words, for use in a human, it is desirable to use a human, humanized, or chimeric human antibody.

B) IFN-α and Modified IFN-α

In various embodiments chimeric moieties of this invention comprise an interferon (e.g., IFN-α) joined to the targeting moiety (e.g., anti-HER2/neu antibody). The interferon can be a full length wild-type interferon (e.g. IFN-α, IFN-β, IFN-γ, etc.) an interferon fragment (e.g., an IFN-α fragment), and/or a mutated interferon. Typically the interferon fragment is one that possesses the endogenous activity of preferably at a level of at least 80%, more preferably at least 90% or 95%, most preferably at least 98%, 99%, 100%, or a level greater than the wild-type interferon.

Means of identifying such modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408).

The resulting library members can then be screened according to standard methods know to those of skill in the art. Thus, for example, IFN-α activity can be assayed by measuring antiviral activity against a particular test virus. Kits for assaying for IFN-α activity are commercially available (see, e.g., iLite™ alphabeta kit by Neutekbio, Ireland).

These methods are intended to be illustrative and not limiting. Using the teaching provided herein, other suitable modified interferons (e.g., modified IFN-α, IFN-β, IFN-γ, etc.) can readily be identified and produced.

C. Attachment of the Antibody (e.g., Anti-HER2/neu) to the IFN-α.

Generally speaking, the targeting moiety (e.g., an anti-HER2/neu antibody, and anti-CD20 antibody, etc.) can be joined together in any order. Thus, for example, the antibody can be joined to either the amino or carboxy terminal of the interferon. The antibody can also be joined to an internal region of the interferon, or conversely, the interferon can be joined to an internal location or to any terminus of the antibody, as long as the attachment does not interfere with binding of the antibody to that target marker (e.g., the HER2/neu receptor).

The antibody (e.g., a C6 anti-HER2/neu) and the interferon (e.g., IFN-α) can be attached by any of a number of means well known to those of skill in the art. In certain embodiments, the interferon is conjugated, either directly or through a linker (spacer), to the antibody. In certain embodiments, however, it is preferable to recombinantly express the chimeric moiety as a fusion protein.

i) Chemical Conjugation of the Targeting Moiety to the Interferon.

In certain embodiments, the targeting moiety (e.g., an anti-HER2/neu antibody such as C6.5, C6MH3-B1, G98A, ML3-9, H3B1, B1D2, etc.) is chemically conjugated to the interferon (e.g., IFN-α) molecule. Means of chemically conjugating molecules are well known to those of skill The procedure for conjugating two molecules varies according to the chemical structure of the agent. Polypeptides typically contain variety of functional groups; e.g., carboxylic acid (COOH) or free amine (—NH$_2$) groups, that are available for reaction with a suitable functional group on the other peptide, or on a linker to join the molecules thereto.

Alternatively, the antibody and/or the IFN-α can be derivatized to expose or attach additional reactive functional groups. The derivatization can involve attachment of any of a number of linker molecules such as those available from Pierce Chemical Company, Rockford Ill.

A "linker", as used herein, typically refers to a molecule that is used to join the antibody to the IFN-α. In various embodiments, the linker is capable of forming covalent bonds to both the antibody and to the IFN-α. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the IFN-α through their side groups (e.g., through a disulfide linkage to cysteine). In certain preferred embodiments, the linkers are joined to the alpha carbon amino and/or carboxyl groups of the terminal amino acids of the antibody and/or the IFN-α.

A bifunctional linker having one functional group reactive with a group on the antibody and another group reactive on the IFN-α, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982); Waldmann (1991) *Science,* 252: 1657; U.S. Pat. Nos. 4,545,985 and 4,894,443, and the like.

ii) Production of Fusion Proteins.

In certain embodiments, a chimeric targeting moiety-interferon fusion protein is synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. anti-HER2/neu-IFN-α, anti-CD20-IFN-α, etc.) of this invention can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862); the solid support method of U.S. Pat. No. 4,458,066, and the like.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins of the present invention can be cloned using DNA amplification methods such as polymerase chain reaction (PCR). Thus, for example, the gene for IFN-α is PCR amplified, using a sense primer containing the restriction site for, e.g., NdeI and an antisense primer containing the restriction site for HindIII. This can produce a nucleic acid encoding the mature IFN-α sequence and having terminal restriction sites. An antibody having "complementary" restriction sites can similarly be cloned and then ligated to the IFN-α and/or to a linker attached to the IFN-α. Ligation of the nucleic acid sequences and insertion into a vector produces a vector encoding IFN-α joined to the anti-HER2/neu antibody.

While the two molecules can be directly joined together, one of skill will appreciate that the molecules can be separated by a peptide spacer consisting of one or more amino acids. Generally the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

It was a surprising discovery, however, that certain linkers are unsuitable for preparation of fusion proteins of the present invention. Thus, for example, the $(Gly_4Ser)_3$ (SEQ ID NO:31) linker was not well suited for the production of an anti-CD20-IFN-α construct. Without being bound to a particular theory, it is believed the interferon was being removed from the fusion protein by proteolysis. Western blot analysis using anti-Fc and anti-interferon, confirmed that both of the upper bands were heavy chains, but only the largest contained interferon.

Accordingly, in certain preferred embodiments, it is desirable to use a linker that is resistant to proteolysis. Certain preferred linkers are linkers that are not the $(Gly_4Ser)_3$ (SEQ ID NO:31) linker. Certain preferred linkers are linkers shorter than 15 amino acids, or linkers shorter than 14, 13, 12, 11, 10, 9, 8, 7, 6, 5, 4, 3, or 2 amino acids in length. In certain embodiments the linker is an alpha helical linker ranging in length up to about 12 or 13 or 14 amino acids in length.

Certain illustrative proteolysis-resistant linkers well suited for use in the constructs of this invention are shown in Table 2.

TABLE 2

Illustrative proteolysis-resistant linkers.

| Linker Seq | SEQ ID NO |
|---|---|
| GGGGS | 32 |
| A(EAAAK)$_n$A where n = 1 | 33 |
| where n = 2 | 34 |
| where n = 3 | 35 |
| where n = 4 | 36 |
| where n = 5 | 37 |
| GGGGG | 38 |
| GGGGGGGG | 39 |
| GGAGG | 40 |
| GAGAGAGAGA | 41 |
| RPLSYRPPFPFGFPSVRP | 42 |
| YPRSIYIRRRHPSPSLTT | 43 |
| TPSHLSHILPSFGLPTFN | 44 |
| RPVSPFTFPRLSNSWLPA | 45 |
| SPAAHFPRSIPRPGPIRT | 46 |
| APGPSAPSHRSLPSRAFG | 47 |
| PRNSIHFLHPLLVAPLGA | 48 |
| MPSLSGVLQVRYLSPPDL | 49 |
| SPQYPSPLTLTLPPHPSL | 50 |
| NPSLNPPSYLHRAPSRIS | 51 |

TABLE 2 -continued

Illustrative proteolysis-resistant linkers.

| Linker Seq | SEQ ID NO |
|---|---|
| LPWRTSLLPSLPLRRRP | 52 |
| PPLFAKGPVGLLSRSFPP | 53 |
| VPPAPVVSLRSAHARPPY | 54 |
| LRPTPPRVRSYTCCPTP | 55 |
| PNVAHVLPLLTVPWDNLR | 56 |
| CNPLLPLCARSPAVRTFP | 57 |

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene is typically operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.: Deutscher (1990) *Methods in Enzymology* Vol. 182: *Guide to Protein Purification*., Academic Press, Inc. N.Y., and the like). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein (e.g., anti-HER2/neu-IFN-α, anti-CD20-IFN-α, etc.) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine.

In certain embodiments a transient expression system can be used to express the chimeric constructs described herein. Although many cell lines potentially can be used, one cell line that works well for transient expression is 293T. For transient expression of 293T on Day 0, 9 million cells in 25 ml are seeded for each 150 mm tissue culture plate. A 1 mg/ml of PEI (Polyethylenimine) is made using sterile water. For the expression of a complete antibody or antibody fusion protein, 25 μg each of H and L (50 ug total) is used per plate. A volume of 5 ml is used for transfection of each 150 mm plate. The DNA is mixed with DMEM, the PEI is then added and the mixture is incubated at room temperature for 10 mins. 1.75 μg PEI is used for each ug of DNA. For transfection, the old medium is removed, discarded and replaced with 20 ml of fresh medium (Iscoves+5% calf serum). The transfection mix is added and the plate is swirled. On Day 2, the medium is replaced with 30 ml of Iscoves medium containing 1% FBS (fetal bovine serum) to minimize the amount of bovine Ig present. Supernatants are collected from the cells on Days 4, 6 and 13 by removing the medium and replacing it with 30 ml of fresh Iscover containing 1% FBS.

The cloning and expression of an anti-HER2/neu-IFN-α fusion protein is illustrated herein in Example 1, while the cloning and expression of an anti-CD20-IFN-α fusion protein is shown in Example 2.

One of skill would recognize these expression methods are illustrative and not limiting. Modifications can be made to the fusion proteins described herein without diminishing their activity/efficacy. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Other modifications can be made to increase serum half-life and/or bioavailability. Such modifications include, but are not limited to the incorporation of D amino acids (especially in the linker), the use of non-naturally occurring amino acids, pegylation of the fusion protein, and the like.

D. Other Multi-Valent Targeting Moieties.

In certain embodiments this invention contemplates the use of multivalent, preferably trivalent, quadravalent, pentavalent or greater targeting moieties (e.g., anti-HER2/neu antibodies, anti-CD20 antibodies, etc.) to target the interferon to a target cell.

For example, multivalent anti-HER2/neu moieties can be produced by any of a number of methods. For example, linkers having three, four, or more reactive sites can be reacted with anti-HER2/neu antibodies to form a trimer or greater conjugate.

In certain embodiments, phage display, yeast display, bacterial display, or other display systems can be used to express and display multiple copies (e.g., at least 3, at least 4, at least 5, at least 6 copies, etc.) of a targeting (e.g., anti-HER2/neu, anti-CD20, etc.) antibody and thereby effectively provide a multivalent targeting moiety.

II. Combined Uses.

The chimeric constructs of this invention are useful for inhibiting the growth and/or proliferation of target cells (e.g., cancer cells). In various embodiments the chimeric moieties can be used to inhibit disease progression, to shrink tumor size, and/or to stabilize regression/remission.

Particularly in the treatment of cancer, the compositions and methods of the invention may also include additional therapeutic and/or pharmacologically acceptable agents. For instance, the compositions or methods may involve other agents for the treatment of cancer. Such agents include, but are not limited to alkylating agents (e.g., mechlorethamine (Mustargen), cyclophosphamide (Cytoxan, Neosar), ifosfamide (Ifex), phenylalanine mustard; melphalen (Alkeran), chlorambucol (Leukeran), uracil mustard, estramustine (Emcyt), thiotepa (Thioplex), busulfan (Myerlan), lomustine (CeeNU), carmustine (BiCNU, BCNU), streptozocin (Zanosar), dacarbazine (DTIC-Dome), cis-platinum, cisplatin (Platinol, Platinol AQ), carboplatin (Paraplatin), altretamine (Hexalen), etc.), antimetabolites (e.g. methotrexate (Amethopterin, Folex, Mexate, Rheumatrex), 5-fluoruracil (Adrucil, Efudex, Fluoroplex), floxuridine, 5-fluorodeoxyuridine (FUDR), capecitabine (Xeloda), fludarabine: (Fludara), cytosine arabinoside (Cytaribine, Cytosar, ARA-C), 6-mercaptopurine (Purinethol), 6-thioguanine (Thioguanine), gemcitabine (Gemzar), cladribine (Leustatin), deoxycoformycin; pentostatin (Nipent), etc.), antibiotics (e.g. doxorubicin (Adriamycin, Rubex, Doxil, Daunoxome-liposomal preparation), daunorubicin (Daunomycin, Cerubidine), idarubicin (Idamycin), valrubicin (Valstar), mitoxantrone (Novantrone), dactinomycin (Actinomycin D, Cosmegen), mithramycin, plicamycin (Mithracin), mitomycin C (Mutamycin), bleomycin (Blenoxane), procarbazine (Matulane), etc.), mitotic inhibitors (e.g. paclitaxel (Taxol), docetaxel (Taxotere), vinblatine sulfate (Velban, Velsar, VLB), vincristine sulfate (Oncovin, Vincasar PFS, Vincrex), vinorelbine sulfate (Navelbine), etc.), chromatin function inhibitors (e.g., topotecan (Camptosar), irinotecan (Hycamtin), etoposide (VP-16, VePesid, Toposar), teniposide (VM-26, Vumon), etc.), hormones and hormone inhibitors (e.g. diethylstilbesterol (Stilbesterol, Stilphostrol), estradiol, estrogen, esterified estrogens (Estratab, Menest), estramustine (Emcyt), tamoxifen (Nolvadex), toremifene (Fareston) anastrozole (Arimidex), letrozole (Femara), 17-OH-progesterone, medroxyprogesterone, megestrol acetate (Megace), goserelin (Zoladex), leuprolide (Leupron), testosteraone, methyltestosterone, fluoxmesterone (Android-F, Halotestin), flutamide (Eulexin), bicalutamide (Casodex), nilutamide (Nilandron), etc.) INHIBITORS OF SYNTHESIS (e.g., aminoglutethimide (Cytadren), ketoconazole (Nizoral), etc.), immunomodulators (e.g., rituximab (Rituxan), trastuzumab (Herceptin), denileukin diftitox (Ontak), levamisole (Ergamisol), bacillus Calmette-Guerin, BCG (TheraCys, TICE BCG), interferon alpha-2a, alpha 2b (Roferon-A, Intron A), interleukin-2, aldesleukin (ProLeukin), etc.) and other agents such as 1-aspariginase (Elspar, Kidrolase), pegaspagase (Oncaspar), hydroxyurea (Hydrea, Doxia), leucovorin (Wellcovorin), mitotane (Lysodren), porfimer (Photofrin), tretinoin (Veasnoid), and the like.

III. Pharmaceutical Compositions.

In order to carry out the methods of the invention, one or more active agents (chimeric moieties) of this invention are administered, e.g. to an individual diagnosed as having a cancer. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The active agents of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering e.g. from a cancer, or at risk of cancer (e.g. after surgical removal of a primary tumor) in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain preferred embodiments, the active agents of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain embodiments elevated serum half-life can be maintained by the use of sustained-release protein "packaging" systems. Such sustained release systems are well known to those of skill in the art. In one preferred embodiment, the ProLease™ biodegradable microsphere delivery system for proteins and peptides (see, e.g., Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the active agent in a polymer matrix that can be compounded as a dry formulation with or without other agents.

The ProLease™ microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer micro spheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

IV. Kits.

In certain embodiments, this invention provides for kits for the treatment a primary cancer and/or in an adjunct therapy. Kits typically comprise a container containing a chimeric moiety of the present invention (e.g., anti-HER2/neu-IFN-α, anti-CD20-IFN-α, etc.). The chimeric moiety can be present in a pharmacologically acceptable excipient.

In addition the kits can optionally include instructional materials disclosing means of use of the chimeric moiety (e.g. to treat a cancer and/or as an adjunct therapeutic). The instructional materials may also, optionally, teach preferred dosages, counter-indications, and the like.

The kits can also include additional components to facilitate the particular application for which the kit is designed. Thus, for example, and additionally comprise means for disinfecting a wound, for reducing pain, for attachment of a dressing, and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Anti-Her2/Neu IgG3 and IFN-Alpha Fusion Protein Demonstrates Potent Apoptotic and Anti-Tumor Activities Against B Cell Lymphoma In the present study, we constructed a fusion protein consisting of anti-HER2/neu-IgG3 with the variable region of C6MH3-B1 (20) and IFN-α, and investigated its effect on a murine B cell lymphoma, 38C13, expressing human HER2/neu (38C13/HER2). We chose to evaluate IFN-α targeting to tumor in this model given the responsiveness of this B cell lymphoma to IFN-α (21). Fusion of IFN-α to an Ab significantly increased its in vivo half-life. Anti-HER2/neu-IgG3-IFN-α was found to be efficient in inhibiting the growth in vivo of both small and established 38C13/HER2 tumors with no signs of systemic toxicity observed at effective doses. Anti-HER2/neu-IgG3-IFN-α inhibited the growth of and induced apoptosis in 38C13/HER2 cells. These results indicate that fusion of IFN-α to a tumor-specific Ab results in an agent effective for the treatment of B cell lymphoma.

Materials and Methods

Cell Lines and Culture Conditions

38C13 is a highly malignant murine B cell lymphoma derived from C3H/HeN mice. The construction and characterization of 38C13 expressing human HER2/neu (38C13/HER2) has been previously described (6). Both 38C13 and 38C13/HER2 were cultured in IMDM (Irvine Scientific) supplemented with 2 mM L-glutamine, 10 U/ml penicillin, 10 microg/ml streptomycin (GPS; Sigma-Aldrich) and 10% calf serum (Atlanta Biologicals). Murine myeloma P3X63Ag8.653 (American Type Culture Collection) and its derivatives expressing anti-HER2 IgG3-IFN-α or IgG3-IFN-α were grown in IMDM supplemented with 10% calf serum and GPS. L929 fibroblasts (American Type Culture Collection) were cultured in IMDM with 5% calf serum and GPS. The construction and characterization of CT26/HER2, a murine colon adenocarcinoma cell line overexpressing human HER2/neu, has been previously described (6). CT26/HER2 was cultured in IMDM with 5% calf serum and GPS.

Plasmid Construction

The H and L chain variable regions of C6MH3-B1, an anti-human HER2/neu scFv wen inserted into the human γ3 H chain (pAH4802) and κL chain (pAG4622) expression vectors, respectively (22), and used to produce chimeric IgG3 of this specificity. To construct the anti-human HER2/neu-IgG3 (C6MH3-B1)-IFN-α fusion protein, PCR was first used to introduce a BamH1 restriction enzyme site upstream and XbaI restriction enzyme site downstream of the mature murine IFN-α gene amplified by PCR from genomic DNA of BALB/c mice with the forward primer 5'-CGC GGA TCC TGT GAC CTG CCT CAG ACT C-3 (SEQ ID NO:58) and the reverse primer 5'-GCT CTA GAT CAT TTC TCT TCT CTC AGT CTT C-3 (SEQ ID NO:59). The final PCR product was ligated into a TA vector. The resulting vector, after sequencing, was digested with BamH1 and XbaI to release the DNA fragment which was inserted into the vector pAH9612 containing the IgG3 constant region with the C6MH3-B1 H chain variable region and a GGGGSGGGGSGGGGS (SEQ ID NO:60) peptide linker at the end of $C_H3$. The final PCR product, pAH9616, contained anti-HER2/neu-IgG3 followed by a GGGGSGGGGSGGGGS (SEQ ID NO:61) peptide linker and murine IFN-α.

Production and Purification of Recombinant Proteins

Plasmid encoding the IgG3 H chain with the C6MH3-B1 variable region fused to IFN-α was transfected into P3X63Ag8.653 cells expressing either L chain with the C6MH3-B1 variable region (23) to produce anti-HER2/neu-IgG3-IFN-α or nonspecific L chain (4D5; Genentech) (6) to produce IgG3-IFN-α by electroporation with a pulse of 960 μFd capacitance and 0.2 V. Transfectants producing anti-HER2/neu(C6MH3-B1)-IgG3, anti-HER2/neu(C6MH3-B1)-IgG3-IFN-α, or IgG3-IFN-α were selected and characterized as previously described (6). Anti-HER2/neu(C6MH3-B1)-IgG3 was purified from culture supernatants using protein G immobilized on Sepharose 4B fast flow (Sigma-Aldrich), and anti-HER2/neu(C6MH3-B1)-IgG3-IFN-α and IgG3-IFN-α were purified from culture supernatants using protein A immobilized on Sepharose 4B fast flow (Sigma-Aldrich). Purity and integrity were assessed by Coomassie blue staining of proteins separated by SDS-PAGE. The international reference standard for mouse IFN-α provided by the National Institutes of Health was used to determine IFN activity of the fusion proteins. rIFN-α was obtained from PBL Biomedical Laboratories.

FPLC Analysis of IgG3-IFN-α Fusion Protein

To determine whether the fusion protein exists as monomer and/or polymers in solution, 100 μg of IgG3-IFN-α mixed with 400 μg of OVA to provide an internal control was analyzed by gel filtration on a 30×1.5-cm Superose 6 column attached in a fast protein liquid chromatography (FPLC) using PBS and 0.5 ml/min flow rate. Gel filtration on the same column of IgA2m that exists predominantly as dimer Ab with a molecular mass of 350 kDa and a mixture of Miles IgG of molecular mass 150 kDa and OVA of molecular mass 45 kDa were used to provide molecular mass standards.

Flow Cytometry Analysis of HER2/Neu-Binding Activity

To detect the reactivity of various anti-HER2/neu fusion proteins with CT26/HER2 cells, 1×10⁶ cells were incubated at 4° C. for 1 h with 10 pM of the fusion protein. For some experiments, the fusion proteins were preincubated with 900 U of heparin at 4° C. for 17 h before incubation with CT26/HER2 cells. Cells were then reacted with biotinylated rat anti-human IgG (BD Biosciences) diluted ¹⁄₁₀₀. The bound biotinylated Abs were detected with PE-labeled streptavidin (BD Biosciences) diluted ¹⁄₁₅₀₀ and cells were analyzed by flow cytometry using a FACScan (BD Biosciences).

IFN-α Antiviral Activity

The L-929 fibroblast cell line sensitive to the vesicular stomatitis virus (VSV) infection was used to quantify the biological activity of IFN-α. L-929 cells were plated in a 96-well tissue culture plate (Falcon; BD Biosciences) at a density of $4 \times 10^4$ cells/well and incubated overnight at 37° C. in a 5% CO2 atmosphere. Afterward, serial dilutions of different IFN-α fusion proteins or standard IFN-α (international reference standard for mouse IFN-α; National Institutes of Health, Bethesda, Md.) were added and the plate was incubated at 37° C. for 24 h. Four thousand PFU of VSV was then added to each well and incubated at 37° C. for another 48 h. Surviving adherent cells were stained with 50 μl of crystal violet (0.05% in 20% ethanol) for 10 min. The plates were washed with water and the remaining dye was solubilized by the addition of 100 μl of 100% methanol. Plates were read using an ELISA reader at 595 nm.

Assay for the Antiproliferative Effect of Anti-HER2/Neu-IgG3-IFN-α

In brief, 38C13 or 38C13/HER2 cells were plated in a 96-well tissue culture plate at a density of $1.25 \times 10^4$ cells/well and serial dilutions of different fusion proteins were added. The plates were then incubated for 48 h at 37° C. in a 5% CO2 atmosphere. Plates were developed by addition of 20 μl of MTS solution (Promega) and analyzed at 490 nm using an ELISA reader. Inhibition of proliferation (percent) was calculated as: 100×[(ODexp−ODblank)/(ODmedium−ODblank)]×100.

Assay for Apoptosis

In brief, $1 \times 10^6$ cells were treated with different fusion proteins for 72 h. The cells were then washed with ice-cold PBS. The annexin V/propidium iodide (PI) assay was conducted following procedures suggested by the manufacturer using the Vybrant Apoptosis Assay Kit 2 (Molecular Probes).

Proliferation of CFSE-Labeled 38C13/HER2 Tumor Cells

In brief, $1 \times 10^6$ cells were incubated with 2.5 μM CFSE (Molecular Probes) for 10 min at 37° C. Cells were then treated with 1 nM of different fusion proteins for 48 h and analyzed by flow cytometry following procedures suggested by the manufacturer using the CellTrace CFSE Cell Proliferation Kit (Molecular Probes).

Mice

Female C3H/HeN mice 6-8 wk of age obtained from Taconic Farms were used. Animals were housed in a facility using autoclaved polycarbonate cages containing wood-shaving bedding. The animals received food and water ad libitum. Artificial light was provided under a 12/12-h light/dark cycle. The temperature of the facility was 20° C. with 10-15 air exchanges per hour.

Half-Life

Murine rIFN-α (PBL Biomedical Laboratories), IgG3-IFN-α, and anti-HER2/neu-IgG3-IFN-α were iodinated to 10 μCi/μg with $^{125}$I using Iodo-Beads (Pierce) according to the manufacturer's protocol. Mice were injected i.p. with 66 μCi of $^{125}$I-labeled proteins. At various intervals after injection of $^{125}$I-labeled rIFN-α, IgG3-IFN-α, or anti-HER2/neu-IgG3-IFN-α, residual radioactivity was measured using a mouse whole body counter (Wm. B. Johnson and Associates).

Tumor Challenge and Ab Therapy

C3H/HeN mice received 1000 38C13/HER2 tumor cells s.c. Treatment was given by i.p. injection either 1, 3, and 5 days or 12, 13, and 14 days after tumor challenge. Tumors were measured every other day, and the tumor volume (in cubic millimeters) was approximated using the following formula: [length (mm)×width (mm)×width (mm)]/2 (24). Animals were observed until the length of the s.c. tumor reached 15 mm or until any mouse was observed to be suffering or appeared to be moribund. Animals under these conditions were euthanized humanely according to institutional policy.

Western Blot Analysis and Ab

In brief, 38C13/HER2 cells were treated with different fusion proteins for the indicated times, washed with ice-cold PBS, and lysed on ice for 10 min in lysis buffer (0.125% Nonidet P-40, 0.875% Brij 97, 10 mM Tris-HCl (pH 7.5), 2 mM EDTA, 0.15 M NaCl, 0.4 mM Na3VO4, 0.4 mM NaF, 1 mM PMSF, 2.5 μM leupeptin, and 2.5 μM aprotinin). Cell lysates were clarified at 10,000×g for 10 min at 4° C. Protein samples were then boiled in sample buffer before separation on 8% SDS-PAGE gels and transferred onto polyvinylidene fluoride microporous membranes (Millipore). After blocking with 3% BSA in 150 mM NaCl, 50 mM Tris-HCl (pH 7.6; TBS) for 1 h at room temperature, blots were probed with the indicated primary Abs overnight at 4° C. The blots were then washed three times at room temperature with 0.05% Tween 20 in TBS, incubated with the appropriate secondary Abs conjugated with HRP, and detected by a peroxidase-catalyzed ECL detection system (ECL; Pierce). Polyclonal rabbit antiphosphoSTAT1 was obtained from Cell Signaling Technology. Polyclonal HRP-conjugated donkey anti-rabbit IgG was obtained from Amersham Biosciences. Polyclonal rabbit anti-GAPDH was obtained from Abcam.

Statistical Analysis

Statistical analyses were performed using a two-tailed Student's t test for in vitro studies and log-rank (Mantel-Cox) analysis for animal survival curves.

Results

Production and Characterization of Anti-HER2/Neu-IgG3-IFN-α

Figure 2B:
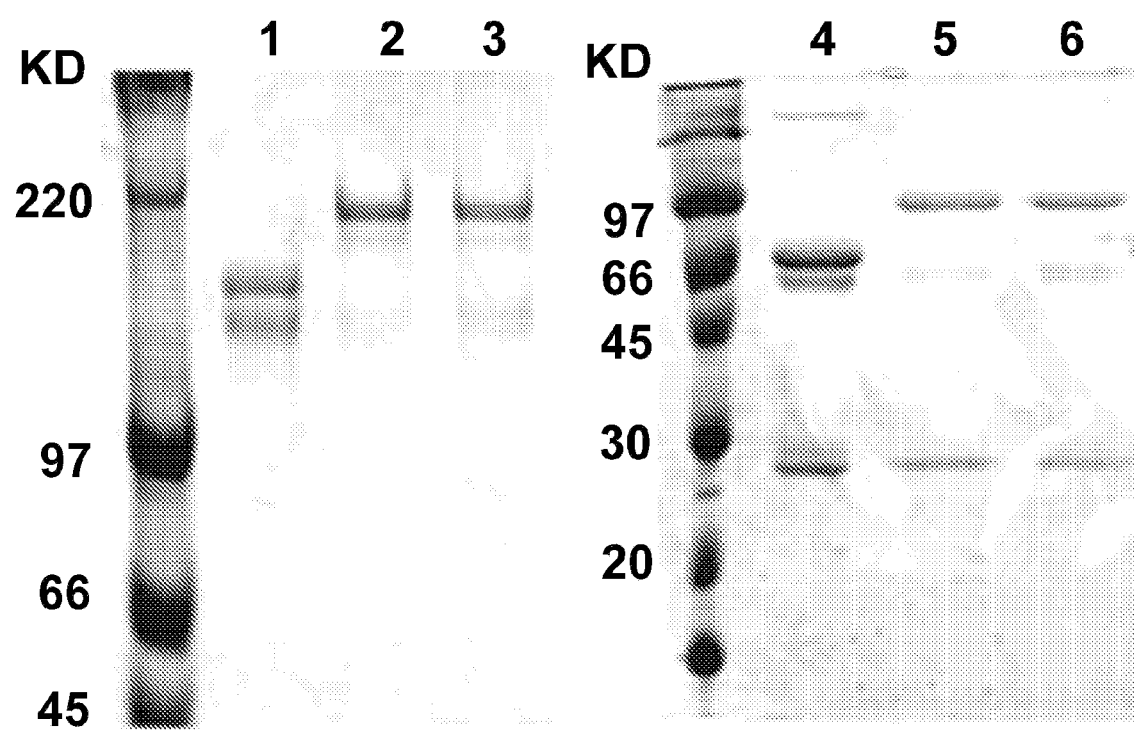

The construction and expression of anti-HER2/neu-IgG3 with the C6MH3-B1 (20) variable region has been described previously (23). The amino-terminal end of mature murine IFN-α was fused to the carboxyl-terminal end of anti-HER2/neu-IgG3 separated by a flexible [(Gly$_4$)Ser]$_3$ (SEQ ID NO:31) linker (FIG. 2A). An identical fusion protein, IgG3-IFN-α, lacking HER2/neu specificity was constructed by replacing the C6MH3-B1 L chain with the 4D5 (rhuMab HER2, herceptin; Genentech) L chain. The proteins purified from culture supernatants using protein G were analyzed by SDS-PAGE under nonreducing and reducing conditions (FIG. 2B). In the absence of reducing agents, anti-HER2/neu-IgG3 (FIG. 2B, lane 1) migrates with a molecular mass of 170 kDa, whereas anti-HER2/neu-IgG3-IFN-α (FIG. 2B, lane 2) and IgG3-IFN-α (FIG. 2B, lane 3) are 210 kDa, the size expected for a complete IgG3 with two molecules of murine IFN-α attached (FIG. 2A). After treatment with the reducing agent, L chains migrating with a molecular mass of 25 kDa are seen for these proteins (FIG. 2B, lanes 4-6). However, the anti-HER2/neu-IgG3 has an H chain with a molecular mass of 60 kDa (FIG. 2B, lane 4), whereas IgG3-IFN-α (FIG. 2B, lane 5) and anti-HER2/neu-IgG3-IFN-α (FIG. 2B, lane 6) have an H chain with a molecular mass of 80 kDa as expected. The lower band in lane 1 (FIG. 2B) is bovine IgG which also bound to the protein G column; the bovine H and L chains are also seen in lane 4 (FIG. 2B) and to a lesser degree in lanes 5 and 6 (FIG. 2B). FPLC analysis showed that the IgG3-IFN-α fusion protein existed as a monomer in solution (data not shown).

Ag Binding and Antiviral Activity of Anti-HER2/Neu-IgG3-IFN-α

Figure 2C:
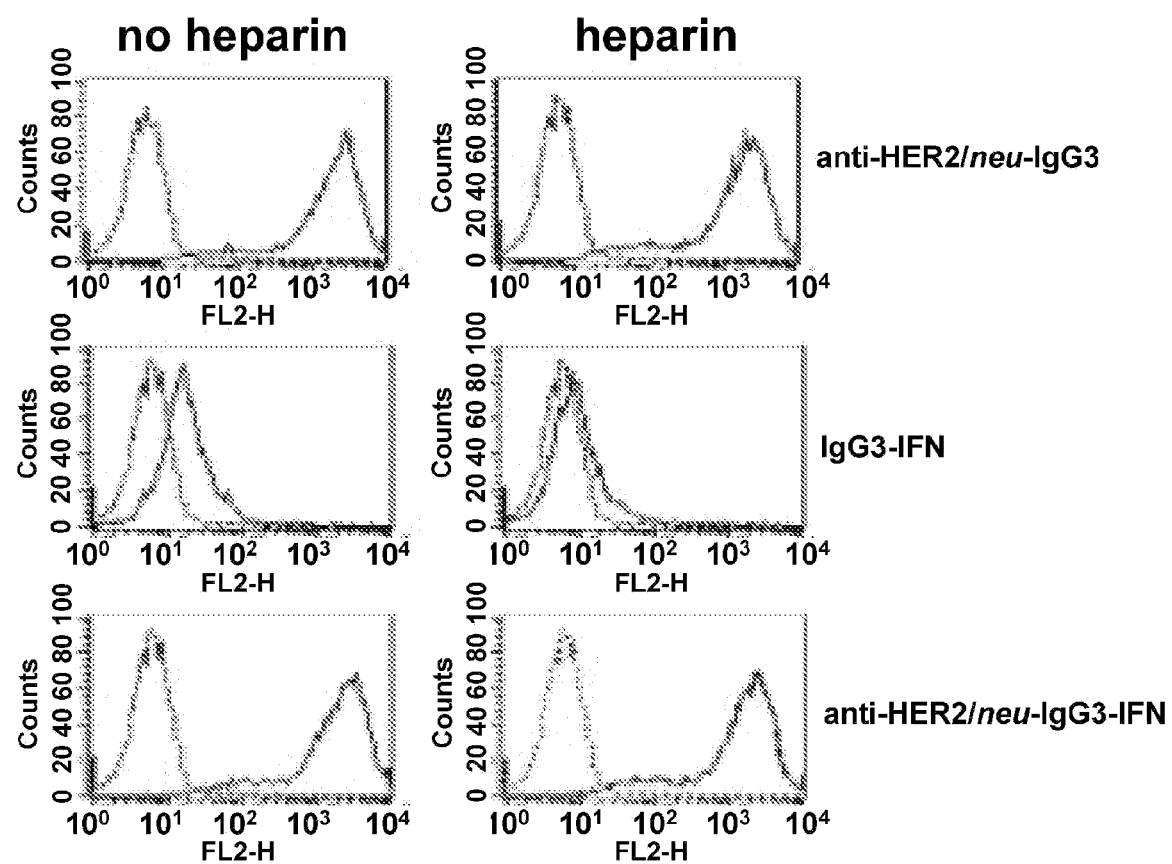

Both anti-HER2/neu-IgG3 and anti-HER2/neu-IgG3-IFN-α bound CT26/HER2 cells, which express high levels of human HER2/neu, while IgG3-IFN-α bound CT26/HER2 weakly (FIG. 2C). Many cytokines including IL-1, IL-2, IL-6 (25) and IFN-α (26) have been shown to interact with heparin. To determine whether the weak interaction between IgG3-IFN-α and CT26/HER2 is due to the heparin binding, proteins were incubated with heparin before the addition to CT26/HER2. Heparin inhibited the binding of IgG3-IFN-α to CT26/HER2 cells but did not inhibit the binding of anti-HER2/neu-IgG3 and anti-HER2/neu-IgG3-IFN-α (FIG. 2C).

Figure 2D:
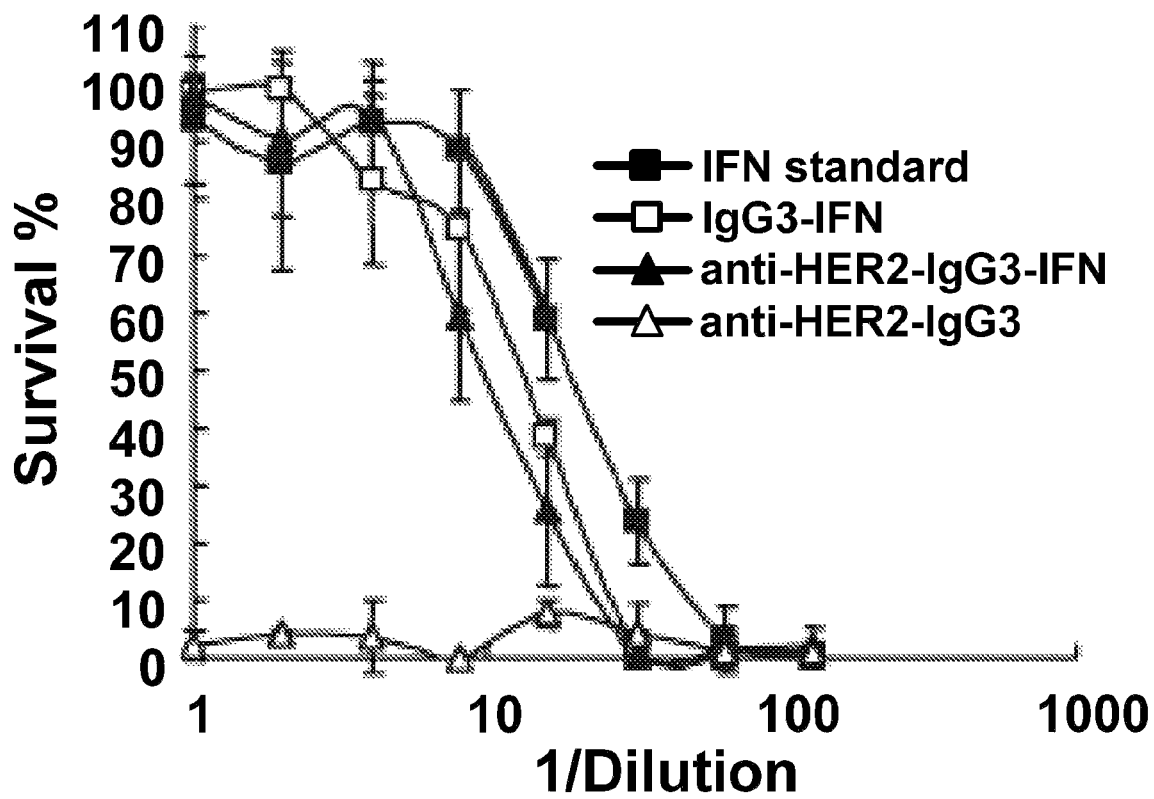

These results demonstrated that anti-HER2/neu-IgG3-IFN-α retained its ability to bind Ag and IgG3-IFN-α does not recognize HER2/neu. The L-929 fibroblast cell line sensitive to VSV infection was used to quantify the IFN-α biological activity of the fusion proteins in comparison to an IFN-α standard. Both anti-HER2/neu-IgG3-IFN-α and IgG3-IFN-α exhibited ~2400 U of IFN-α activity/µg activity against VSV-induced cytotoxicity in L-929 cells, while anti-HER2/neu-IgG3 exhibited no anti-viral activity (FIG. 2D).

In Vivo Antitumor Activity of Fusion Proteins

Figure 3A:
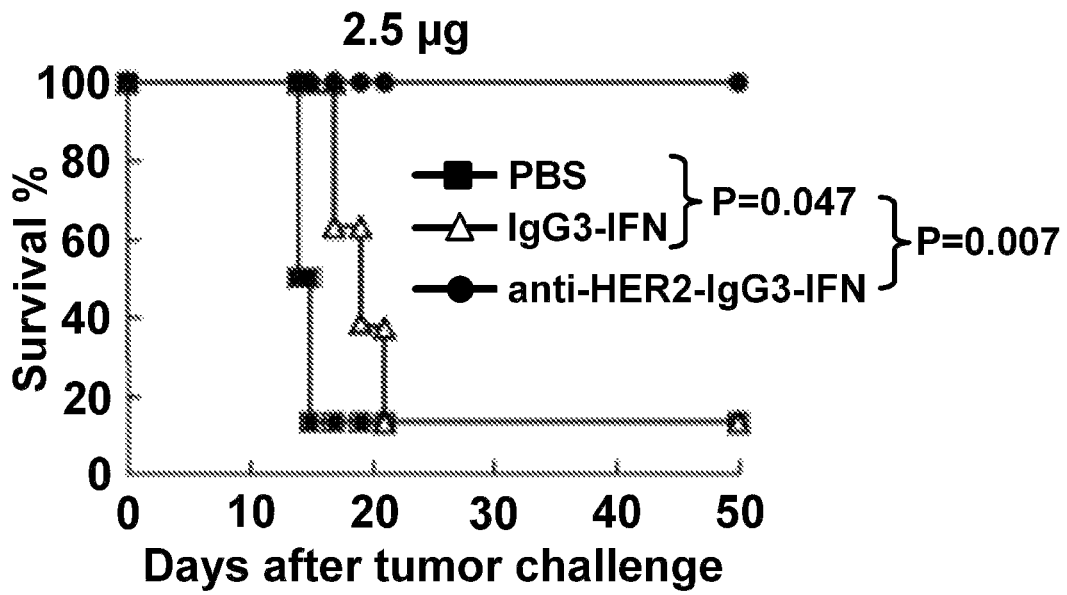
FIGS. 3A and 3B show in vivo antitumor activity of different IFN-α fusion proteins and rIFN-α. C3H/HeN mice were s.c. challenged with 1×10³ 38C13/HER2 cells and i.p. treated with either 2.5 µg (FIG. 3A) or 1 µg (FIG. 3B) of the indicated proteins at days 1, 3, and 5 after tumor challenge. The tumor volume of each mouse is measured. Animals were observed until the diameter of the s.c. tumor reached 15 mm.
Figure 3B:
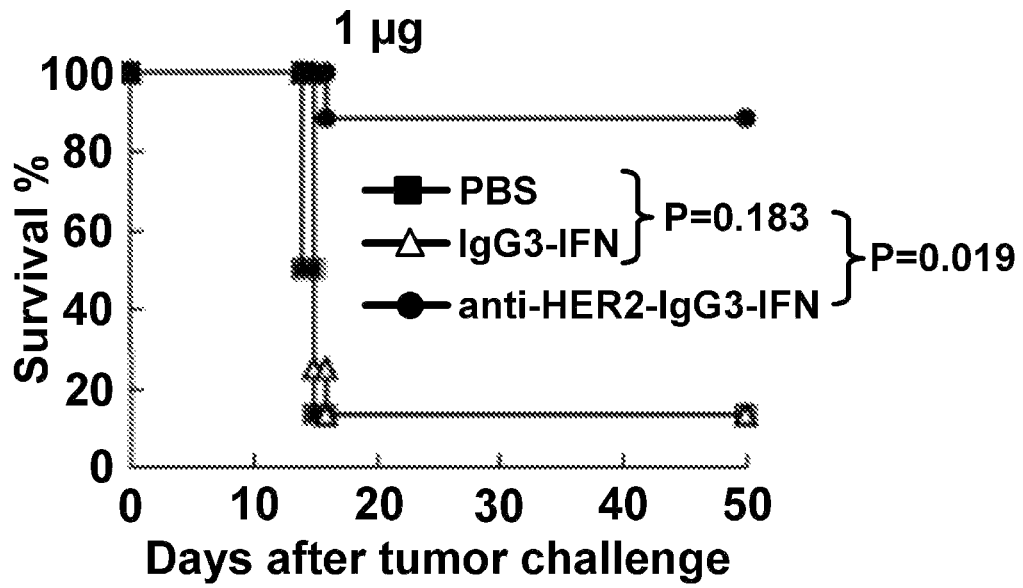

To determine the in vivo antitumor activity of anti-HER2/neu-IgG3-IFN-α, syngeneic mice were inoculated s.c. with $1\times10^3$ 38C13/HER2 tumor cells and treated on days 1, 3, and 5 after tumor challenge by i.p. administration of different doses of protein (FIG. 3A-3B). Mice treated with 2.5 µg of IgG3-IFN-α showed some regression of tumor growth, with one (13%) of eight mice alive after 50 days (FIG. 3A). However, in vivo targeting of IFN-α to tumors using a tumor-specific Ab dramatically improved its antitumor effect. All mice treated with 2.5 µg (FIG. 3A) of anti-HER2/neu-IgG3-IFN-α remained tumor free 50 days after tumor challenge (p=0.0048 compared with PBS control), and none of the treated mice showed evidence of toxicity. Thus, targeting of IFN-α to the tumor cell surface resulted in significant antitumor activity compared with IFN-α linked to a nonspecific Ab (p=0.007). Targeted anti-HER2/neu-IgG3-IFN-α continued to show potent antitumor activity when a lower dose was used. Seven (88%) of eight mice treated with 1 µg (FIG. 3B) of anti-HER2/neu-IgG3-IFN-α remained tumor free after 50 days. In marked contrast, at this lower dose mice treated with IgG3-IFN-α showed tumor growth similar to mice treated with PBS (p=0.183) and only one (13%) of eight mice survived. When the treatment was increased to three doses of 5 µg, both anti-HER2/neu-IgG3-IFN-α and IgG3-IFN-α were effective in preventing tumor growth (data not shown) undoubtedly reflecting the fact that 38C13 cells are sensitive to IFN-α treatment (21, 27, 28). Tumor growth in mice treated with 5 µg of anti-HER2/neu-IgG3 Ab was the same as the PBS control, suggesting that Ab alone has no antitumor effect in vivo (data not shown). These results indicated that targeting of IFN-α to the tumor cells by a tumor-specific Ab can dramatically potentiate its effectiveness which was most clearly seen when low doses were administered. Importantly, this antitumor activity can be achieved without any evident toxicity.

IFN-α Fused to an Ab Results in Improved Antitumor Activity Compared with Free IFN-α

Figure 4A:
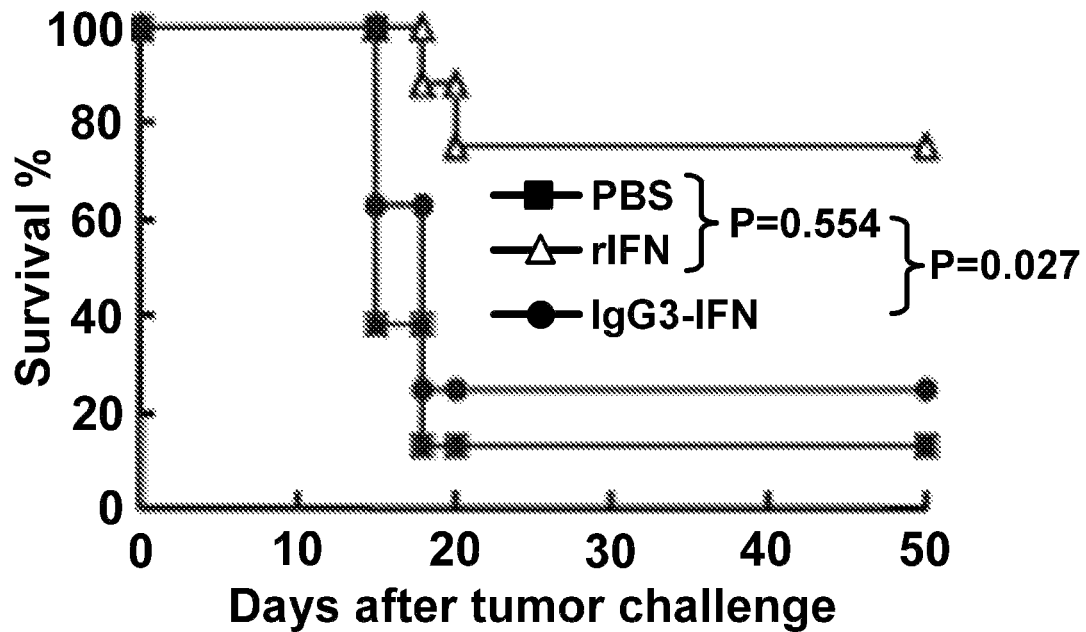
FIGS. 4A and 4B show that fusion of IgG3 to IFN-α improved its antitumor activity and increased its in vivo half-life.

As described above, we found that IFN-α fused to a non-tumorspecific Ab exhibited antitumor activity. To compare its antitumor activity with that of soluble rIFN-α, mice were inoculated s.c. with $1\times10^3$ 38C13/HER2 tumor cells and treated 1 and 3 days after tumor challenge by i.p. administration of 9600 U (4 µg) of IgG3-IFN-α or 9600 U of rIFN-α (FIG. 4A). All mice treated with 9600 U of IgG3-IFN-α showed delayed tumor growth and 75% of the mice remained tumor free 50 days after tumor challenge (p=0.027). In contrast, mice treated with the same number of units of rIFN-α were not statistically different from PBS controls in their tumor growth pattern.

Figure 4B:
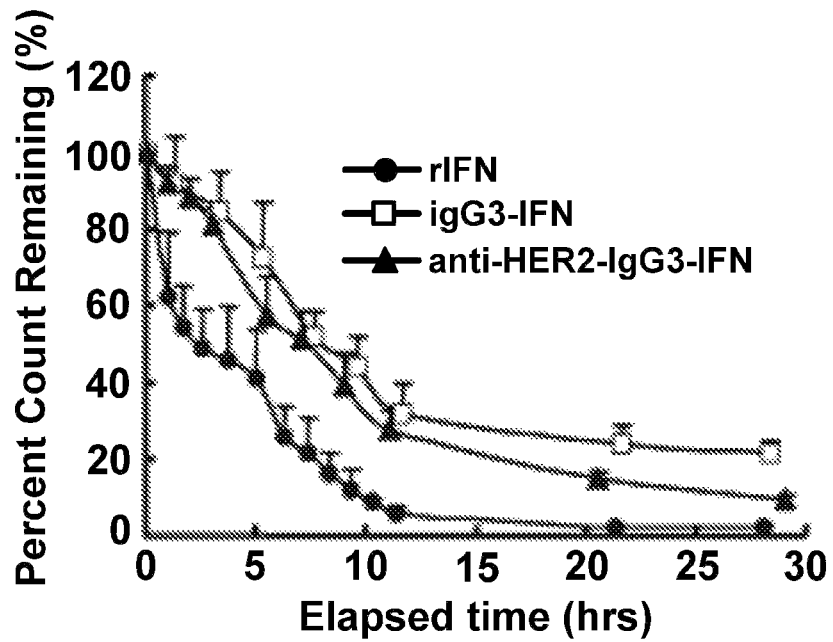

IFN-α has a very short in vivo half-life (29). In previous study, fusion of Abs to cytokines has been shown to increase their halflife (6). The clearance of $^{125}$I-labeled rIFN-α, IgG3-IFN-α, or anti-HER2/neu-IgG3-IFN-α was examined in C3H/HeN mice. Mice were injected i.p. with 66 µCi of $^{125}$I-labeled proteins and the residual radioactivity was measured using a mouse whole body counter. rIFN-α was cleared rapidly with 50% eliminated by ~2.5 h (FIG. 4B). In contrast, both anti-HER2/neu-IgG3-IFN-α and IgG3-IFN-α exhibited significantly increased in vivo half-life with ~8 h required for elimination of 50% of the injected radioactivity. This increased half-life may contribute to the antitumor efficacy of the IFN-α fusion proteins. Thus, fusion of an IgG3 Ab to IFN-α can significantly improve its in vivo antitumor activity. However, this antitumor activity can be further improved by targeting the IFN-α to the tumor, making it effective at lower doses.

Anti-HER2/Neu-IgG3-IFN-α Inhibited Proliferation of Tumor Cells In Vitro

IFN-α has multiple activities including activation of the immune response and direct cytotoxicity against tumors. To investigate potential mechanisms of the antitumor effects seen using either anti-HER2/neu-IgG3-IFN-α or IgG3-IFN-α, the eight mice remaining tumor free (see FIG. 3A) were challenged with $1\times10^3$ 38C13/HER2 tumor cells. Surprisingly, all mice resembled untreated mice and quickly developed bulky tumors (data not shown). These results imply that under these experimental conditions of low tumor burden the IFN-α fusion proteins did not initiate a protective adaptive immune response, but instead the potent antitumor activity of the IFN-α fusion proteins is mediated either by the innate immune system or by a direct cytotoxic effect on tumor cells.

Figure 5A:
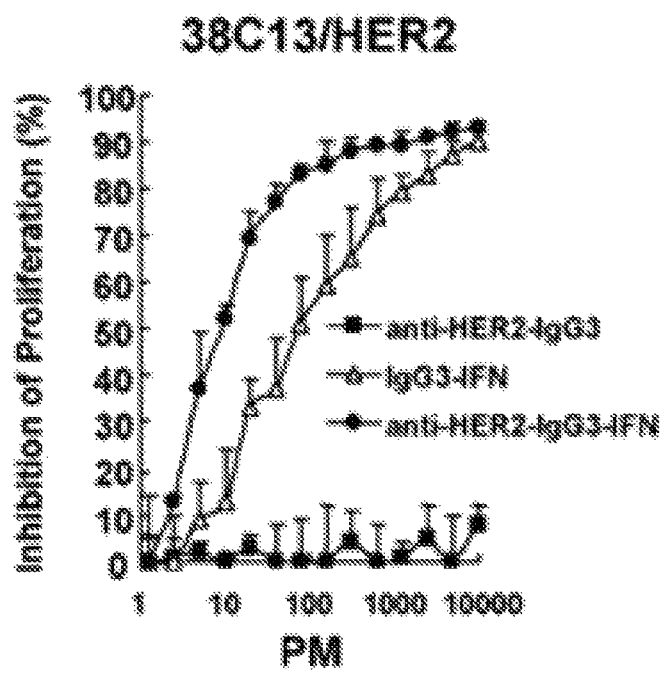
FIGS. 5A, 5B, 5C, and 5D show that IFN-α fusion proteins inhibited cell proliferation and induced apoptosis in 38C13/HER2 cells in vitro. IFN-α fusion proteins inhibited tumor cell proliferation. After incubation for 48 h with different doses of the different fusion proteins, viable 38C13/HER2 (FIG. 5A) or 38C13 (FIG. 5B) cells were measured using the MTS assay. These experiments were performed three times in triplicate; error bars, SD of the measurements.
Figure 5B:
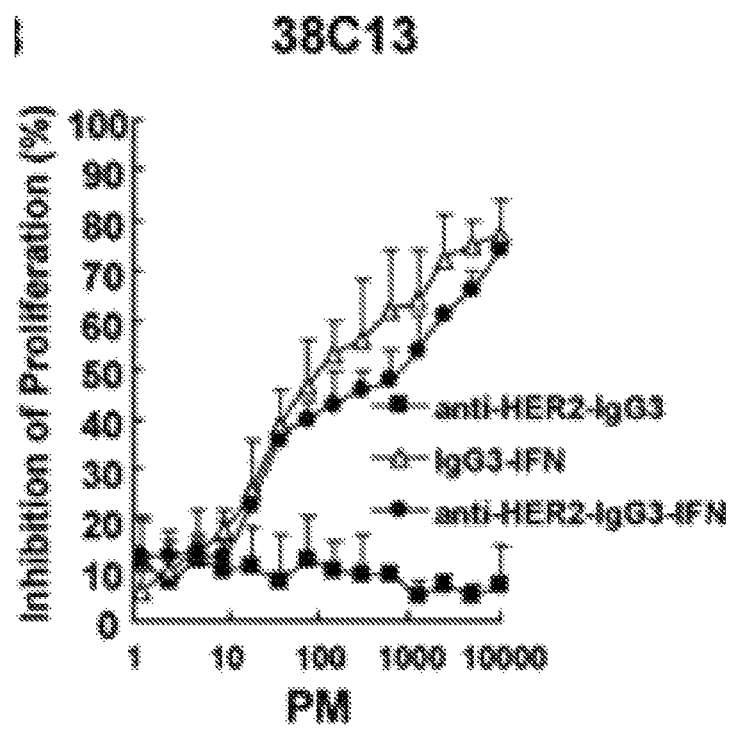

To determine whether IFN-α fusion proteins are directly cytotoxic to tumor cells, the 38C13/HER2 or parental 38C13 tumor cells were incubated with different proteins for 48 h and cell proliferation measured using the MTS assay. Treatment with anti-HER2/neu-IgG3 did not significantly inhibit the proliferation of either 38C13/HER2 or parental 38C13 tumor cells (FIGS. 5A and 5B). Although both anti-HER2/neu-IgG3-IFN-α and IgG3-IFN-α inhibited the proliferation of 38C13/HER2 tumor cells, anti-HER2/neu-IgG3-IFN-α was more effective than IgG3-IFN-α with IP50 values of 10 and 100 pM for anti-HER2/neu-IgG3-IFN-α and IgG3-IFN-α, respectively (FIG. 5A). In contrast, anti-HER2/neu-IgG3-IFN-α and IgG3-IFN-α exhibited similar antiproliferative activity against parental 38C13 tumor cells. These results provided evidence that IFN-α fusion proteins can directly inhibit the proliferation of the B cell lymphoma 38C13, and targeting IFN-α to tumor cells potentiated this effect.

Anti-HER2/Neu-IgG3-IFN-α Induced Apoptosis in Tumor Cells In Vitro

Figure 5C:
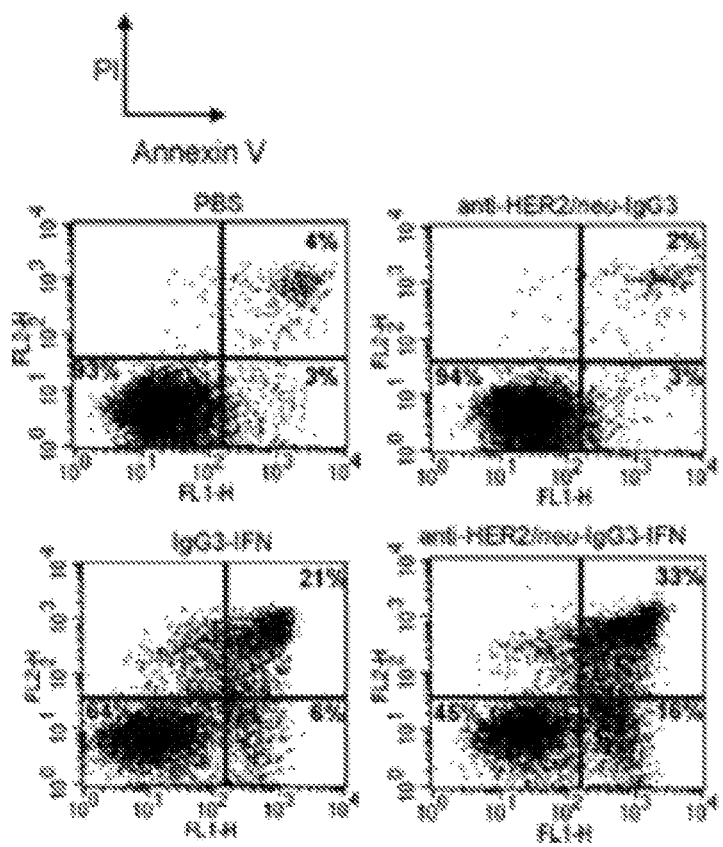

IFN-α signaling can induce apoptosis in some tumor cell lines. To determine whether apoptosis contributed to the antiproliferative effect we observed, 38C13/HER2 cells treated with different proteins were assayed for the translocation of phosphatidylserine from the inner to the outer leaflet of the plasma membrane using the annexin V-affinity assay (30). Dead cells were stained by PI, which enters cells with a disrupted plasma membrane and binds to DNA. Compared with the PBS control, there was no increase in the number of dead cells (annexin V/PI bright, 2%) or early apoptotic cells (annexin V bright, 3%) following treatment with anti-HER2/neu-IgG3 (FIG. 5C). In contrast, when cells were treated with IgG$_3$-IFN-α, there was a significant increase in the number of dead cells (21%) and early apoptotic cells (6%). Treatment with anti-HER2/neu-IgG3-IFN-α resulted in a further increase in both the number of dead cells (33%) and early apoptotic cells (16%). These results indicated that IFN-α can induce apoptosis in 38C13/HER2 tumor cells, and that targeting IFN-α to tumor cells can markedly increase this effect.

Figure 5D:
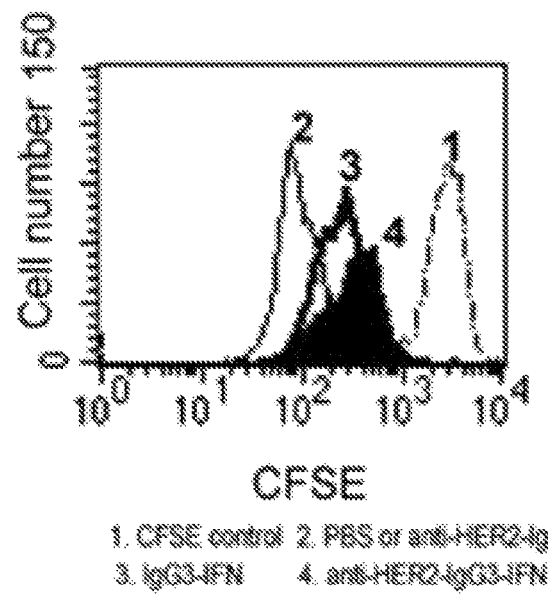

In addition to inducing apoptosis, IFN-α can directly inhibit the proliferation of tumor cells (31). To determine whether both inhibition of proliferation and apoptosis were taking place in treated tumor cells, CFSE-labeled 38C13/HER2 cells were treated with different proteins for 48 h, the live cells were gated, and the level of CFSE was determined by flow cytometry. The CFSE signal in anti-HER2/neu-IgG3-treated cells (FIG. 5D, thin line) overlapped with the PBS-treated cells and was significantly less than that of cells fixed immediately after CFSE labeling (FIG. 5D, dotted line), indicating that anti-HER2/neu-IgG3 did not inhibit the proliferation of the 38C13/HER2. In contrast, IgG3-IFN-α significantly inhibited the proliferation of the surviving 38C13/HER2 cells (FIG. 5D, thick line), and targeting IFN-α to 38C13/HER2 cells by anti-HER2/neu-IgG3-IFN-α potentiated this effect (FIG. 5D, black area). These results indicated that although anti-HER2/neu-IgG3-IFN-α treatment did not result in complete cell death by 48 h, the surviving cells had a reduced ability to proliferate.

IFN-α Fusion Proteins Induce STAT1 Activation in Tumor Cells

Figure 6A:
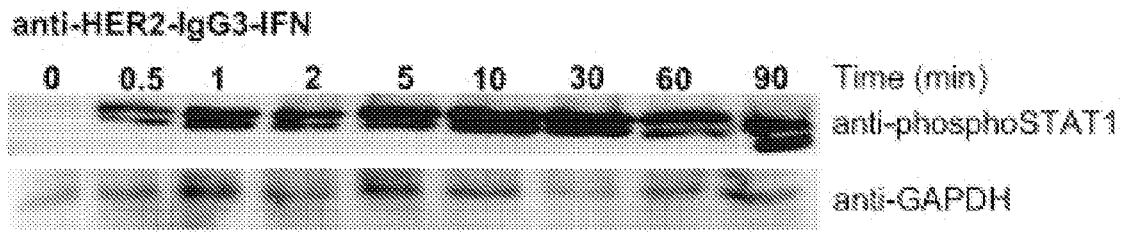
FIGS. 6A, 6B, and 6C show that IFN-α fusion proteins induced STAT1 activation in 38C13/HER2 cells. In brief, 1×10⁷ 38C13/HER2 cells were treated with 1000 U/ml of either anti-HER2/neu-IgG3-IFN-α (FIG. 6A) or IgG3-IFN-α (FIG. 6B) for the indicated times. The cell lysates were separated by SDS-PAGE and analyzed by Western blot using a polyclonal rabbit anti-phosphoSTAT1. To confirm equal loading of protein samples, blots were probed with a HRP-conjugated rabbit polyclonal Ab against GAPDH.
Figure 6B:
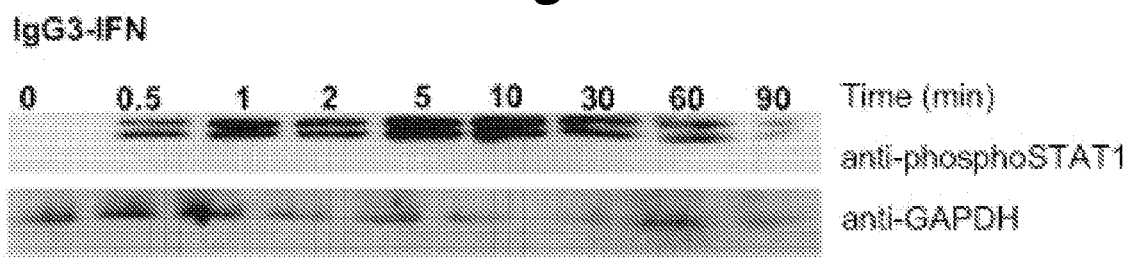
Figure 6C:
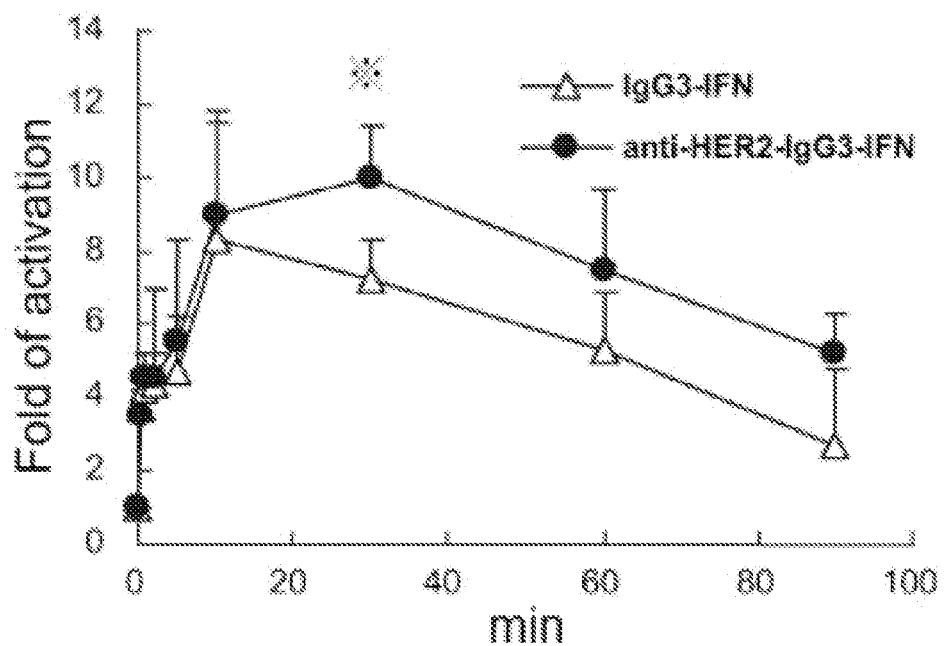

Although engagement of the IFN-α receptor can initiate activation of multiple STAT proteins, STAT1 plays an obligate role in mediating IFN-α-dependent signaling (32). To investigate whether IFN-α fusion proteins initiate IFN-α signaling in 38C13/HER2 and that targeting IFN-α to tumor cells augments this effect, the phosphorylation of STAT1 following treatment was examined. As shown in FIG. 6A-6C, both anti-HER2/neu-IgG3-IFN-α and IgG3-IFN-α initiated robust STAT1 phosphorylation in 38C13/HER2 with STAT1 phosphorylation increasing 8-fold by 10 min. However, the phosphorylation of STAT1 induced by anti-HER2/neu-IgG3-IFN-α persisted for a longer period of time and greater STAT1 phosphorylation was seen at 30, 60, and 90 min in cells treated with anti-HER2/neu-IgG3-IFN-α. These results indicated that IFN-α fusion proteins can induce IFN-α signaling in 38C13 lymphoma cells and targeting IFN-α to tumor cells augments this effect.

Anti-HER2/Neu-IgG3-IFN-α Exhibited Potent Activity Against Established Tumors

Figure 7:
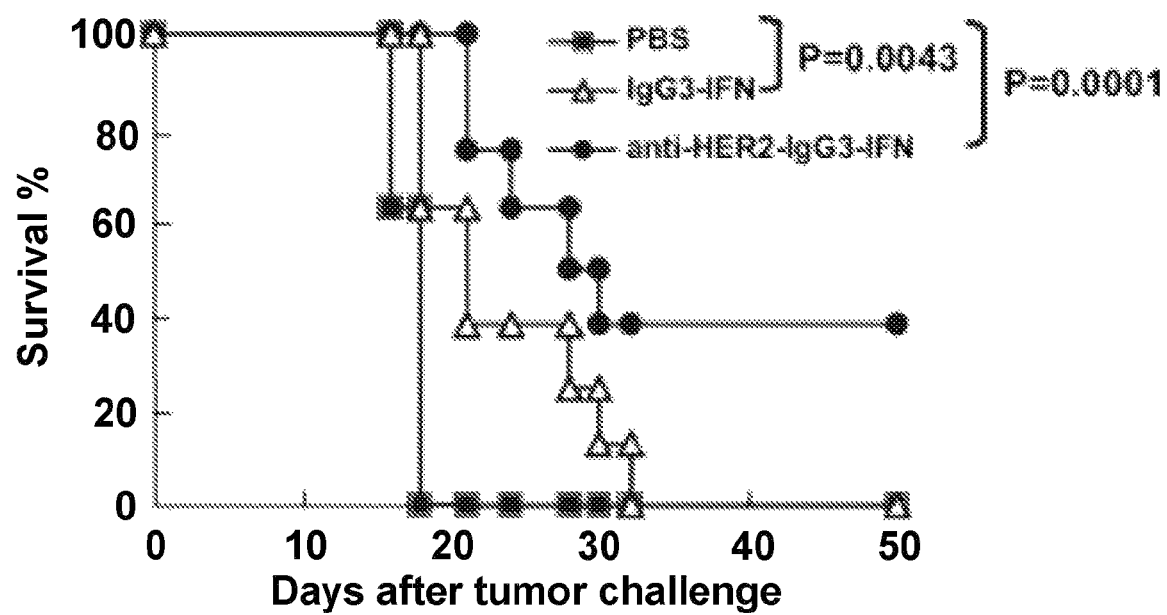
FIG. 7 IFN-α fusion proteins inhibit the growth of established tumor. C3H/HeN mice were injected s.c. with 1×10³ 38C13/HER2 cells. After 12 days, mice were treated i.p. with 5 µg of the indicated protein for 3 consecutive days. The tumor volume of each mouse is measured. Animals were sacrificed when the diameter of the s.c. tumor reached 15 mm.

Because anti-HER2/neu-IgG3-IFN-α exhibited potent cytotoxicity against 38C13/HER2 tumor cells, we investigated whether anti-HER2/neu-IgG3-IFN-α would be effective against established 38C13/HER2 tumors. Syngeneic mice were inoculated s.c. with $1 \times 10^3$ 38C13/HER2 tumor cells and i.p. treated with 5 μg (FIG. 7) of the indicated proteins on days 12, 13, and 14 after tumor challenge. The average tumor size on day 12 is 100 mm3 and treatment with PBS or 10 μg of anti-HER2/neu-IgG3 (data not shown) did not inhibit tumor growth. Treatment with 5 μg of IgG3-IFN-α showed some effect in inhibiting tumor growth; however, all mice developed bulky tumors and none of them survived 32 days after tumor challenge. In contrast all mice treated with 5 μg of anti-HER2/neu-IgG3-IFN-α had delayed tumor growth, and three of eight mice had complete tumor regression and remained tumor free 50 days after tumor challenge (anti-HER2/neu-IgG3-IFN-α vs PBS, p=0.0001; anti-HER2/neu-IgG3-IFN-α vs IgG3-IFN-α, p=0.063). Thus, both IgG3-IFN-α and anti-HER2/neu-IgG3-IFN-α showed antitumor activity but anti-HER2/neu-IgG3-IFN-α was more effective in delaying tumor growth and complete tumor remission was observed only in mice treated with anti-HER2/neu-IgG3-IFN-α. When the treatment dose was increased to 10 μg of the fusion proteins, almost all mice treated with either anti-HER2/neu-IgG3-IFN-α or IgG3-IFN-α had complete tumor regression and remained tumor free after 50 days.

The mice that remained tumor free following treatment with three doses of 10 μg of fusion proteins were rechallenged with $1 \times 10^3$ 38C13/HER2 tumor cells on day 50. All mice remained tumor free (data not shown). These results suggest that an adaptive immune response with immunologic memory is initiated when larger, established tumors are treated with IFN-α fused to an Ab.

Discussion

Although rIFN-α has shown activity against B cell lymphoma and multiple myeloma, inconsistent efficacy and systemic toxicity have limited its usefulness (33). The present work demonstrates that fusing IFN-α to an Ab improves its efficacy against tumors with further improvement seen when IFN-α is targeted to tumor cells by a tumor-specific Ab. This antitumor efficacy is seen without any apparent toxicity. These studies suggest that fusion of IFN-α with tumor-specific Ab may yield an effective biologic agent for the treatment of B cell lymphoma.

To test the hypothesis that directing IFN-α to tumor sites with Ab would result in improved efficacy, we chose a well-characterized murine B cell lymphoma engineered to express a common TAA, HER2/neu, to which Abs are available. Anti-HER2/neu-IgG3-IFN-α appears to be more effective in the treatment of the 38C13 B cell lymphoma than previously described immunotherapeutics, although in the present study a foreign Ag introduced by gene transduction was the target. Treatment with three 1 μg doses of anti-HER2/neu-IgG3-IFN-α beginning 1 day after tumor challenge appeared to be as effective in inhibiting tumor growth as treatment with 10 μg of anti-Id IgG1-IL-2 fusion protein for 5 days beginning 1 day after tumor challenge (34). In addition, anti-HER2/neu-IgG3-IFN-α was effective against established tumors (FIG. 7) while anti-Id IgG1-IL-2 had little antitumor activity when treatment was begun either 3 or 7 days after tumor challenge (34). The ability to cure established tumors also suggests that Ab-targeted IFN-α is a more powerful therapeutic agent than GM-CSF (35), CTLA-4 (36), or CD40 ligand (37) fused to the Id Ag since none of these vaccine strategies was effective against established tumors. Therefore, targeting IFN-α to tumor cells could be a promising approach for treating B cell lymphoma.

Targeting IFN-α to tumor cells with a tumor-specific Ab increases the antitumor efficacy of IFN-α. Anti-HER2/neu-IgG3-IFN-α is more effective in inhibiting proliferation and inducing apoptosis (FIG. 5A-5D) in 38C13/HER2 than IgG3-IFN-α and treatment with either 2.5 or 1 μg of anti-HER2/neu-IgG3-IFN-α was more effective in inhibiting growth of small tumors in vivo than the same doses of IgG3-IFN-α (FIGS. 3A and 3B). These results suggest that the tumor-specific Ab directs IFN-α to the tumor, thereby improving its therapeutic index with decreased systemic toxicity.

Remarkably, IgG3-IFN-α exhibits a more potent antitumor activity than rIFN-α (FIG. 4A). Although rIFN-α is effective in treatment of a variety of tumors (38-40), prolonged treatment with high doses is required to see effective antitumor activity in part because of the very short half-life of the cytokine. In this study, we demonstrated that fusion of an IgG3 Ab to IFN-α significantly increased its half-life (FIG. 4B), and this increased half-life may contribute to the increased in vivo antitumor activity of the fusion protein (FIG. 4A). In addition, the Fc region of the IgG3-IFN-α may help to target IFN-α to the Fc receptors present on B lymphoma cells and consequently increase the antitumor activity. Therefore, fusion of IFN-α to an IgG3 Ab may provide multiple advantages in improving the antitumor efficacy of IFN-α.

Although IFN-α has multiple activities, including activation of the immune response, it appears that direct cytotoxicity plays an important role in the potent antitumor activity of anti-HER2/neu-IgG3-IFN-α. Both IFN-α fusion proteins exhibited apoptotic and antiproliferative activities against 38C13/HER2 with tumor targeting significantly increasing these effects (FIG. 5A-5D). Although the IFN-α fusion proteins were very effective in treating small tumors (FIGS. 3A and 3B), none of the survivors developed an immune response that protected against second tumor challenge, suggesting that the direct cytotoxicity of the IFN-α fusion proteins was very effective in killing the tumor cells and that the adaptive immunity did not play a role when there was a small tumor burden. Because 38C13 is an extremely malignant B lymphoma cell line and mice injected with as few as 200 cells can develop bulky tumors within 20 days (36), the IFN-α fusion proteins must be very effective in killing most of the inoculated tumor cells to result in long-term survivors. Multiple mechanisms, including down-regulation of NF-κB (41), induction of apoptosis by activating caspase-3 (42), and up-regulation of both TRAIL and TRAIL receptors (43), have been shown to be involved in IFN-α-mediated cytotoxicity against tumor cells, and we would expect these mechanisms to contribute to the direct cytotoxicity against tumor cells seen with Ab-IFN-α fusion proteins. Consistent with this, we observed STAT1 activation following treatment of tumor cells with the fusion proteins (FIG. 6A-6C).

Although IFN-α fusion proteins failed to initiate a memory immune response when mice were treated beginning 1 day after tumor inoculation, IFN-α fusion proteins initiated an immune response that protected against second tumor challenge when mice were treated beginning 12 days after tumor inoculation. Therefore, IFN-α fusion proteins can activate protective adaptive immunity in the presence of a sizable tumor burden. Because IFN-α is capable of activating adaptive immunity via stimulation of DC differentiation and maturation (9), it is possible that the established tumors provide more TAAs for DC activation in the presence of IFN-α. In addition, the foreign Ag human HER2/neu may contribute to the antitumor immunity by increasing the immunogenicity of the tumor cells in this model.

CD20, an Ag expressed by B cells, is expressed in most B cell lymphomas (44), and anti-CD20 (rituximab, Genentech;) is one of the most successful cancer therapeutics, having tremendous efficacy against lymphoma with little toxicity (45). Although anti-HER2/neu IgG3-IFN-α is very effective against 38C13/HER2, HER2/neu is not normally expressed in lymphoma cells and therefore, it probably has limited therapeutic application in the treatment of lymphoma but should be effective in the treatments of cancers that express HER2/neu. In contrast, fusion of IFN-α to anti-CD20 is expected to yield a fusion protein effective against lymphoma with even greater antitumor activity by combining the anti-lymphoma activity of anti-CD20 and the potent immunostimulatory and cytotoxic activity of IFN-α in one protein. Additionally, IFN-α may further up-regulate CD20 expression as was seen in patients with B cell lymphoma following IFN-α treatment (46). We are currently studying the effects of anti-CD20-IFN-α fusion proteins in murine models of B cell lymphoma.

In summary, we have constructed and characterized a novel fusion protein in which IFN-α was linked to an antibody recognizing a TAA. Our results indicate that fusion of IFN-α to a tumor-specific antibody can dramatically increase the efficacy of IFN-α with antitumor activity observed without any apparent toxicity. Remarkably, the Ab-IFN-α fusion protein was effective against established tumors. Therefore, IFN (e.g., IFN-α) fused to a tumor-specific antibody shows promise for the treatment of B cell lymphoma.

REFERENCES

1. Disis, M. L., S. M. Pupa, J. R. Gralow, R. Dittadi, S. Menard, and M. A. Cheever. 1997. High-titer HER-2/neu protein-specific antibody can be detected in patients with early-stage breast cancer. *J. Clin. Oncol.* 15: 3363-3367.
2. Dranoff, G., and R. C. Mulligan. 1995. Gene transfer as cancer therapy. *Adv. Immunol.* 58: 417-454.
3. Hrouda, D., M. Perry, and A. G. Dalgleish. 1999. Gene therapy for prostate cancer. *Semin. Oncol.* 26: 455-471.
4. Hurford, R. K., Jr., G. Dranoff, R. C. Mulligan, and R. I. Tepper. 1995. Gene therapy of metastatic cancer by in vivo retroviral gene targeting. *Nat. Genet.* 10: 430-435.
5. Peng, L. S., M. L. Penichet, and S. L. Morrison. 1999. A single-chain IL-12 IgG3 antibody fusion protein retains antibody specificity and IL-12 bioactivity and demonstrates antitumor activity. *J. Immunol.* 163: 250-258.
6. Dela Cruz, J. S., K. R. Trinh, S. L. Morrison, and M. L. Penichet. 2000. Recombinant anti-human HER2/neu IgG3-(GM-CSF) fusion protein retains antigen specificity and cytokine function and demonstrates antitumor activity. *J. Immunol.* 165: 5112-5121.
7. Osenga, K. L., J. A. Hank, M. R. Albertini, J. Gan, A. G. Sternberg, J. Eickhoff, R. C. Seeger, K. K. Matthay, C. P. Reynolds, C. Twist, et al. 2006. A phase I clinical trial of the hu14.18-IL2 (EMD 273063) as a treatment for children with refractory or recurrent neuroblastoma and melanoma: a study of the Children's Oncology Group. *Clin. Cancer Res.* 12: 1750-1759.
8. Belardelli, F., and M. Ferrantini. 2002. Cytokines as a link between innate and adaptive antitumor immunity. *Trends Immunol.* 23: 201-208.
9. Santini, S. M., C. Lapenta, M. Logozzi, S. Parlato, M. Spada, T. Di Pucchio, and F. Belardelli. 2000. Type I interferon as a powerful adjuvant for monocyte-derived dendritic cell development and activity in vitro and in Hu-PBL-SCID mice. *J. Exp. Med.* 191: 1777-1788.
10. Theofilopoulos, A. N., R. Baccala, B. Beutler, and D. H. Kono. 2005. Type I interferons (α/β) in immunity and autoimmunity. *Annu. Rev. Immunol.* 23: 307-336.
11. Finkelman, F. D., A. Svetic, I. Gresser, C. Snapper, J. Holmes, P. P. Trotta, I. M. Katona, and W. C. Gause. 1991. Regulation by interferon_of immunoglobulin isotype selection and lymphokine production in mice. *J. Exp. Med.* 174: 1179-1188.
12. Tough, D. F., P. Borrow, and J. Sprent. 1996. Induction of bystander T cell proliferation by viruses and type I interferon in vivo. *Science* 272: 1947-1950.
13. Ferrantini, M., M. Giovarelli, A. Modesti, P. Musiani, A. Modica, M. Venditti, E. Peretti, P. L. Lollini, P. Nanni, G. Forni, et al. 1994. IFN-α1 gene expression into a metastatic murine adenocarcinoma (TS/A) results in CD8_T cell-mediated tumor rejection and development of antitumor immunity: comparative studies with IFN-α-producing TS/A cells. *J. Immunol.* 153: 4604-4615.
14. Gutterman, J. U., G. R. Blumenschein, R. Alexanian, H. Y. Yap, A. U. Buzdar, F. Cabanillas, G. N. Hortobagyi, E. M. Hersh, S. L. Rasmussen, M. Harmon, et al. 1980. Leukocyte interferon-induced tumor regression in human metastatic breast cancer, multiple myeloma, and malignant lymphoma. *Ann. Intern. Med.* 93: 399-406.
15. Takaoka, A., S. Hayakawa, H. Yanai, D. Stoiber, H. Negishi, H. Kikuchi, S. Sasaki, K. Imai, T. Shibue, K. Honda, and T. Taniguchi. 2003. Integration of interferon- α/β signalling to p53 responses in tumour suppression and antiviral defence. *Nature* 424: 516-523.

16. Sidky, Y. A., and E. C. Borden. 1987. Inhibition of angiogenesis by interferons: effects on tumor- and lymphocyte-induced vascular responses. *Cancer Res.* 47: 5155-5161.

17. Rodriguez-Villanueva, J., and T. J. McDonnell. 1995. Induction of apoptotic cell death in non-melanoma skin cancer by interferon-__. *Int. J. Cancer* 61: 110-114.

18. Akiyama, T., C. Sudo, H. Ogawara, K. Toyoshima, and T. Yamamoto. 1986. The product of the human c-erbB-2 gene: a 185-kilodalton glycoprotein with tyrosine kinase activity. *Science* 232: 1644-1646.

19. Baselga, J., D. Tripathy, J. Mendelsohn, S. Baughman, C. C. Benz, L. Dantis, N. T. Sklarin, A. D. Seidman, C. A. Hudis, J. Moore, et al. 1996. Phase II study of weekly intravenous recombinant humanized anti-p185HER2 monoclonal antibody in patients with HER2/neu-overexpressing metastatic breast cancer. *J. Clin. Oncol.* 14: 737-744.

20. Schier, R., A. McCall, G. P. Adams, K. W. Marshall, H. Merritt, M. Yim, R. S. Crawford, L. M. Weiner, C. Marks, and J. D. Marks. 1996. Isolation of picomolar affinity anti-c-erbB-2 single-chain Fv by molecular evolution of the complementarity determining regions in the center of the antibody binding site. *J. Mol. Biol.* 263: 551-567.

21. Reid, T. R., E. R. Race, B. H. Wolff, R. M. Friedman, T. C. Merigan, and T. Y. Basham. 1989. Enhanced in vivo therapeutic response to interferon in mice with an in vitro interferon-resistant B-cell lymphoma. *Cancer Res.* 49: 4163-4169.

22. Coloma, M. J., A. Hastings, L. A. Wims, and S. L. Morrison. 1992. Novel vectors for the expression of antibody molecules using variable regions generated by polymerase chain reaction. *J. Immunol. Methods* 152: 89-104.

23. Huang, T. H., and S. L. Morrison. 2005. A trimeric anti-HER2/neu ScFv and TNF-α fusion protein induces HER2/neu signaling and facilitates repair of injured epithelia. *J. Pharmacol. Exp. Ther.* 316: 983-991.

24. Carlsson, G., B. Gullberg, and L. Hafstrom. 1983. Estimation of liver tumor volume using different formulas: an experimental study in rats. *J. Cancer Res. Clin. Oncol.* 105: 20-23.

25. Ramsden, L., and C. C. Rider. 1992. Selective and differential binding of interleukin (IL)-1α, IL-1β, IL-2 and IL-6 to glycosaminoglycans. *Eur. J. Immunol.* 22: 3027-3031.

26. Fernandez-Botran, R., J. Yan, and D. E. Justus. 1999. Binding of interferon α by glycosaminoglycans: a strategy for localization and/or inhibition of its activity. *Cytokine* 11: 313-325.

27. Basham, T. Y., M. S. Kaminski, K. Kitamura, R. Levy, and T. C. Merigan. 1986. Synergistic antitumor effect of interferon and anti-idiotype monoclonal antibody in murine lymphoma. *J. Immunol.* 137: 3019-3024.

28. Basham, T. Y., E. R. Race, M. J. Campbell, T. R. Reid, R. Levy, and T. C. Merigan. 1988. Synergistic antitumor activity with IFN and monoclonal anti-idiotype for murine B cell lymphoma. Mechanism of action. *J. Immunol.* 141: 2855-2860.

29. Bailon, P., A. Palleroni, C. A. Schaffer, C. L. Spence, W. J. Fung, J. E. Porter, G. K. Ehrlich, W. Pan, Z. X. Xu, M. W. Modi, et al. 2001. Rational design of a potent, long-lasting form of interferon: a 40 kDa branched polyethylene glycolconjugated interferon α-2a for the treatment of hepatitis C. *Bioconjugate Chem.* 12: 195-202.

30. Koopman, G., C. P. Reutelingsperger, G. A. Kuijten, R. M. Keehnen, S. T. Pals, and M. H. van Oers. 1994. Annexin V for flow cytometric detection of phosphatidylserine expression on B cells undergoing apoptosis. *Blood* 84: 1415-1420.

31. Tiefenbrun, N., D. Melamed, N. Levy, D. Resnitzky, I. Hoffman, S. I. Reed, and A. Kimchi. 1996._Interferon suppresses the cyclin D3 and cdc25A genes, leading to a reversible G0-like arrest. *Mol. Cell. Biol.* 16: 3934-3944.

32. Meraz, M. A., J. M. White, K. C. Sheehan, E. A. Bach, S. J. Rodig, A. S. Dighe, D. H. Kaplan, J. K. Riley, A. C. Greenlund, D. Campbell, et al. 1996. Targeted disruption of the Stat1 gene in mice reveals unexpected physiologic specificity in the JAK-STAT signaling pathway. *Cell* 84: 431-442.

33. Oken, M. M. 1992. New agents for the treatment of multiple myeloma and non-Hodgkin lymphoma. *Cancer* 70: 946-948.

34. Liu, S. J., Y. P. Sher, C. C. Ting, K. W. Liao, C. P. Yu, and M. H. Tao. 1998. Treatment of B-cell lymphoma with chimeric IgG and single-chain Fv antibodyinterleukin-2 fusion proteins. *Blood* 92: 2103-2112.

35. Tao, M. H., and R. Levy. 1993. Idiotype/granulocyte-macrophage colony-stimulating factor fusion protein as a vaccine for B-cell lymphoma. *Nature* 362: 755-758.

36. Huang, T. H., P. Y. Wu, C. N. Lee, H. I. Huang, S. L. Hsieh, J. Kung, and M. H. Tao. 2000. Enhanced antitumor immunity by fusion of CTLA-4 to a self tumor antigen. *Blood* 96: 3663-3670.

37. Huang, H. I., P. Y. Wu, C. Y. Teo, M. N. Chen, Y. C. Chen, D. Silin, and M. H. Tao. 2004. Improved immunogenicity of a self tumor antigen by covalent linkage to CD40 ligand. *Int. J. Cancer* 108: 696-703.

38. Gastl, G., H. Denz, C. Abbrederis, H. Huber, J. Troppmair, J. Wiegele, D. Niederwieser, R. Flener, and C. Huber. 1985. Treatment with low dose human recombinant interferon-_-2-ARG induces complete remission in patients with hairy cell leukemia. *Onkologie* 8: 143-144.

39. Atzpodien, J., H. Poliwoda, and H. Kirchner. 1991._-Interferon and interleukin-2 in renal cell carcinoma: studies in nonhospitalized patients. *Semin Oncol.* 18: 108-112.

40. Krown, S. E., J. Paredes, D. Bundow, B. Polsky, J. W. Gold, and N. Flomenberg. 1992. Interferon-_, zidovudine, and granulocyte-macrophage colony-stimulating factor: a phase I AIDS clinical trials group study in patients with Kaposi's sarcoma associated with AIDS. *J. Clin. Oncol.* 10: 1344-1351.

41. Rath, P. C., and B. B. Aggarwal. 2001. Antiproliferative effects of IFN-α correlate with the downregulation of nuclear factor-_B in human Burkitt lymphoma Daudi cells. *J. Interferon Cytokine Res.* 21: 523-528.

42. Yanase, N., K. Ohshima, H. Ikegami, and J. Mizuguchi. 2000. Cytochrome c release, mitochondrial membrane depolarization, caspase-3 activation, and Bax-α cleavage during IFN-α-induced apoptosis in Daudi B lymphoma cells. *J. Interferon Cytokine Res.* 20: 1121-1129.

43. Oshima, K., N. Yanase, C. Ibukiyama, A. Yamashina, N. Kayagaki, H. Yagita, and J. Mizuguchi. 2001. Involvement of TRAIL/TRAIL-R interaction in IFN-α-induced apoptosis of Daudi B lymphoma cells. *Cytokine* 14: 193-201.

44. Riley, J. K., and M. X. Sliwkowski. 2000. CD20: a gene in search of a function. *Semin. Oncol.* 27: 17-24.

45. McLaughlin, P., A. J. Grillo-Lopez, B. K. Link, R. Levy, M. S. Czuczman, M. E. Williams, M. R. Heyman, I. Bence-Bruckler, C. A. White, F. Cabanillas, et al. 1998. Rituximab chimeric anti-CD20 monoclonal antibody therapy for relapsed indolent lymphoma: half of patients respond to a four-dose treatment program. *J. Clin. Oncol.* 16: 2825-2833.

46. Sivaraman, S., P. Venugopal, R. Ranganathan, C. G. Deshpande, X. Huang, A. Jajeh, S. A. Gregory, T. O'Brien, and H. D. Preisler. 2000. Effect of interferon-α on CD20 antigen expression of B-cell chronic lymphocytic leukemia. *Cytokines Cell Mol. Ther.* 6: 81-87.

Example 2

Anti-CD20-IFNα Fusion Proteins

Introduction

Out initials studies had indicated that a fusion protein with anti-HER2/neu joined to IFN-α was an effective therapeutic for the treatment of HER2/neu expressing lymphoma. We sought to extend these studies to show that fusion of IFN-α with anti-CD20 would be an effective therapeutic for treating CD20 expressing lymphomas. CD20 is present on virtually all lymphomas. However, it should be noted that HER2/neu is expressed on many cancers and it would be expected that the anti-HER2/neu fusion protein would be effective in treating these. In the anti-CD20 fusion protein, we would expect the IFN-α in the fusion protein to both exert a direct cytotoxic effect against the tumor cells and to help elicit an anti-tumor immune response.

Produce Recombinant Antibodies Specific for CD20.

Figure 8:
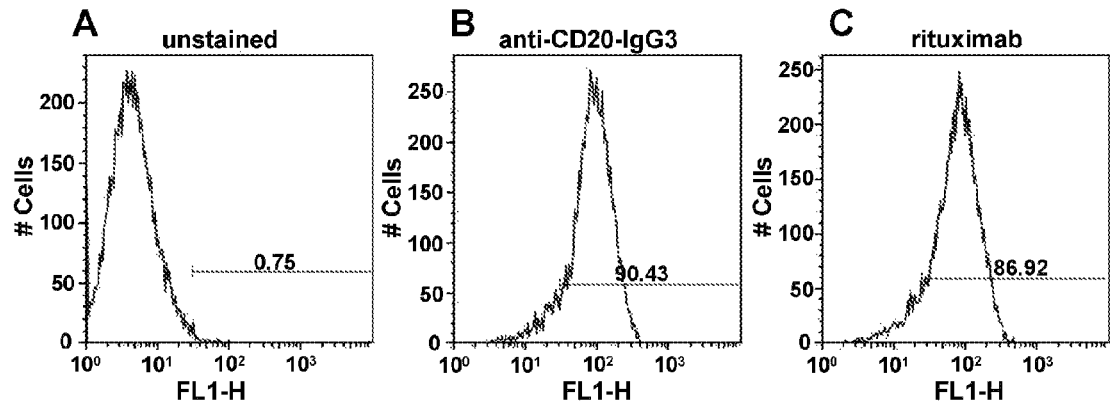
FIG. 8 shows binding of recombinant antibodies to human cells expressing CD20. Daudi cells were incubated with either recombinant IgG3 or Rituximab followed bybiotinylated rat anti-human IgG and PE-labeled strepavidin and analyzed by flow-cytometry. A, cells with only the secondary antibody; B, cells with recombinant IgG3; C, cells with Rituximab

The variable regions for anti-CD20 (Rituximab) were amplified and cloned into expression vectors for the production of chimeric antibodies with human kappa light chains and gamma 3 heavy chains. Protein was produced and its ability to recognize CD20 examined using flow-cytometry and the human B-cell line Daudi. As shown in FIG. 8, the recombinant protein binds as well as Rituximab a recombinant IgG1.

Produce Antibody Fusion Proteins with Human Interferon Joined to Antibodies Specific for CD20 a. Design of Fusion Protein

Figure 9:
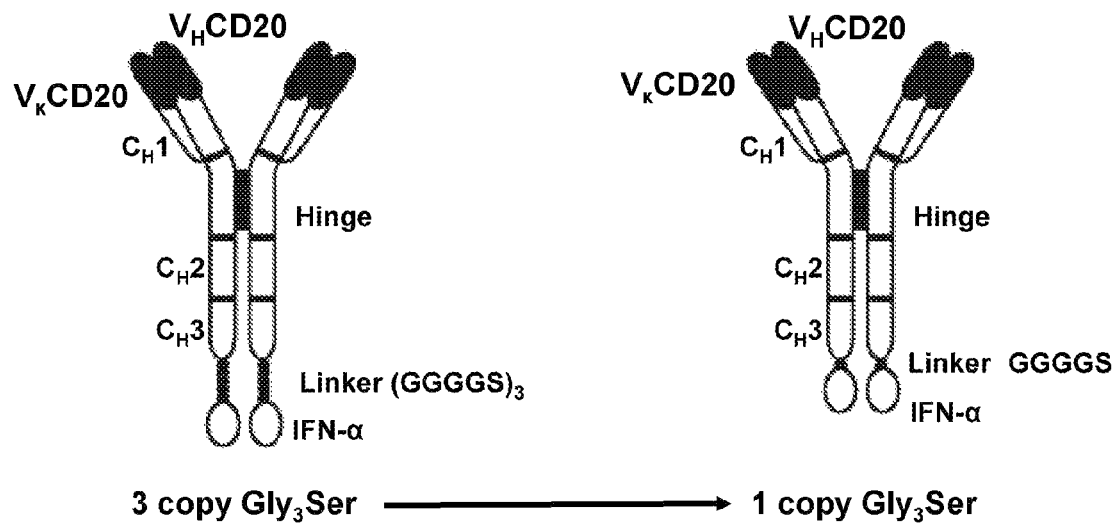
FIG. 9 shows a diagram of the heavy chain of the antibody-IFN-α fusion protein. In particular, the figure illustrates shortening of the (Gly₄Ser)₃ (SEQ ID NO:31) to a Gly₄Ser (SEQ ID NO:32) linker enables production of full-length αCD20-IgG3-mIFNα.

In our initial attempt to make a fusion protein we joined IFN-α to the carboxy-terminus of the human IgG3 gene using a flexible glycine-serine linker consisting of $(Gly_4Ser)_3$ (SEQ ID NO:31). The heavy chain is shown diagrammatically in FIG. 9.

After verifying that the fusion protein vector had the correct nucleotide sequence, it was transfected with the chimeric anti-CD20 light chain into NS0 cells. Transfectants were screened by ELISA for the production of IgG. The clone giving the highest signal was expanded and following subcloning was grown in roller bottles. Supernatants were then passed through protein A Sepharose columns, and the bound proteins eluted and analyzed by SDS-PAGE both unreduced and following reduction (see, FIG. 10). Although the isolated protein was assembled into $H_2L_2$ molecules, most of the isolated protein was smaller than expected. Following reduction, most of the heavy chains were smaller than expected and ran at the same position as a gamma-3 heavy chain lacking a fusion protein. It appeared that the interferon was being removed from the fusion protein by proteolysis. Western blot analysis using anti-Fc and anti-interferon, confirmed that both of the upper bands were heavy chains, but only the largest contained interferon.

Figure 11:
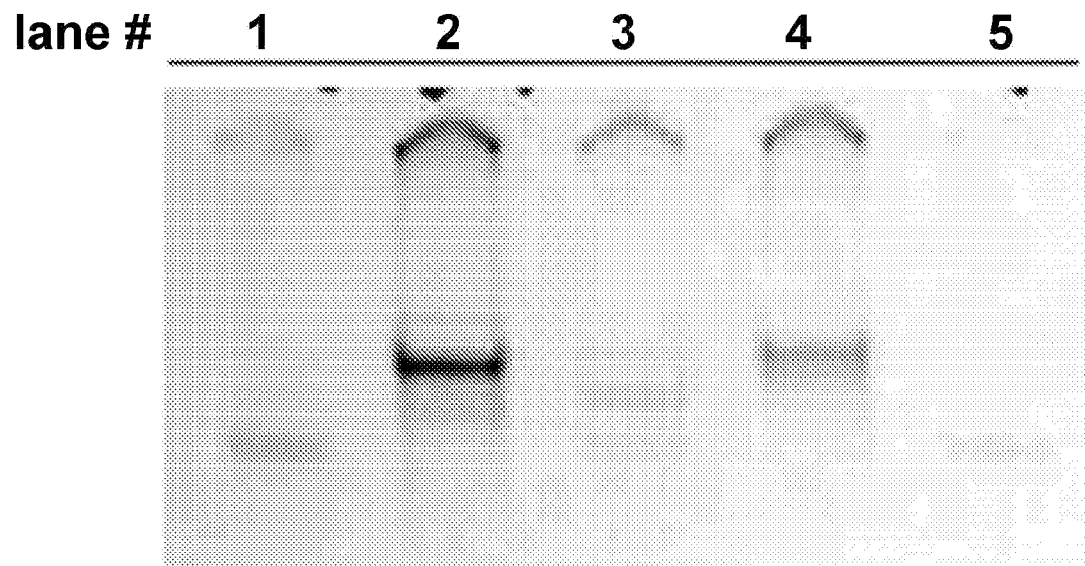
FIG. 11 shows SDS-PAGE analysis of proteins made by transient expression in HEK293T cells. Lane 1, anti-CD20-IgG3-huIFNα with extended (Gly₄Ser)₃ (SEQ ID NO:31) linker; Lane 2, anti-CD20-IgG3 huIFNα with shortened Gly₄Ser (SEQ ID NO:32) linker; Lane 3, anti-CD20-IgG3-muIFNα with extended (Gly₄Ser)₃ (SEQ ID NO:31) linker; Lane 4, anti-CD20-IgG3-muIFNα with shortened Gly₃Ser linker; Lane 5, anti-CD20 IgG3.

Flexible linkers can be a target of proteolytic cleavage. Therefore, we shortened the linker to only one copy of $Gly_4Ser$ (SEQ ID NO:32). These vectors and vectors with the extended linker were transiently transfected along with the appropriate light chain into HEK293T-cells. Cells were radiolabeled by growth in $^{35}$S-methionine, immunoglobulins precipitated with protein A and analyzed by SDS-PAGE (FIG. 11). Whereas cleavage of fusion proteins with extended linkers is readily apparent, cleavage does not take place when the linker consists of only one $Gly_4Ser$ (SEQ ID NO:32). Therefore, the linker used to produce the fusion protein is important and can influence its stability.

b. Recognition of CD20 by the Fusion Proteins

Figure 12:
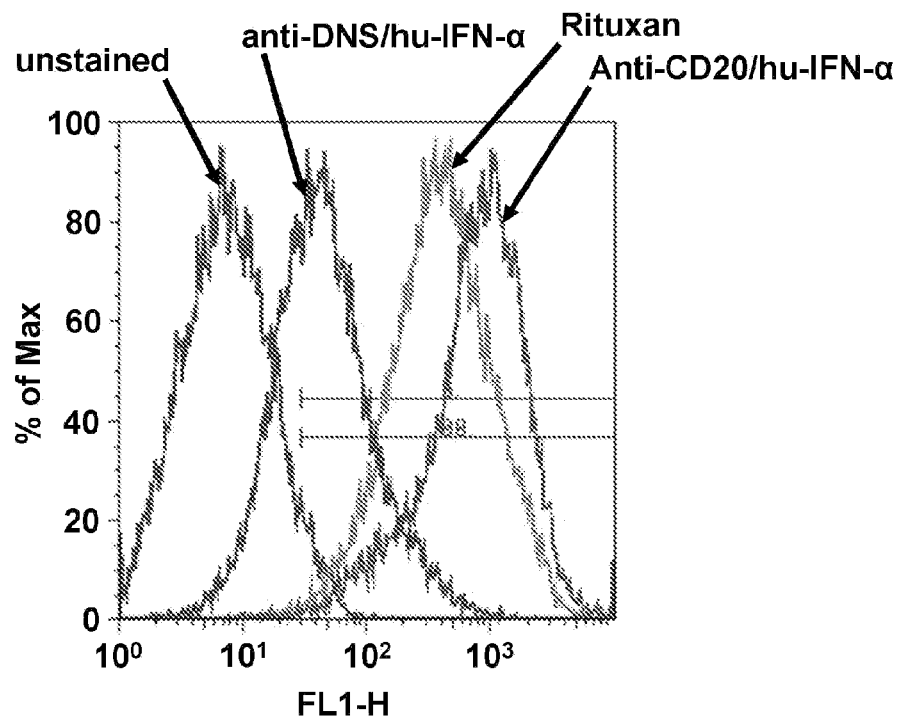
FIG. 12 was shows an analysis of protein binding to Daudi cells using FLOW cytometry. 1×10⁶ Daudi cells were stained with 1 µg of fusion protein containing human IFN-α or Rituxan.
Figure 13:
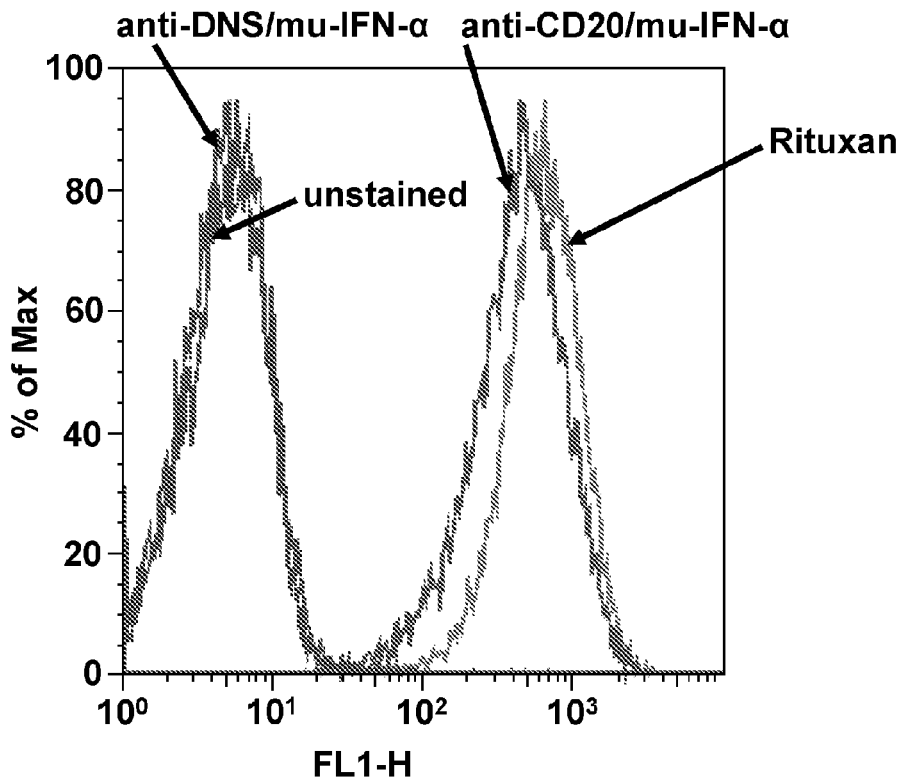
FIG. 13 shows an analysis of protein binding to 38C13/CD20 by FLOW cytometry.

To determine if the fusion protein recognizes CD20, the human cell line Daudi which expresses CD20 was incubated with Rituxan, anti-DNS/IgG3-hu-IFN-α or anti-CD20/IgG3-hu-IFN-α. The anti-CD20/IgG3-hu-IFN-α bound better than Rituxan (FIG. 12). The anti-DNS/IgG3-hu-IFN-α fusion also showed some binding, although less than either CD20 specific protein. We hypothesize that the binding of the anti-DNS/IgG3-hu-IFN-α and the enhanced binding of anti-CD20/IgG3-hu-IFN-α compared to Rituxan is because the hu-IFN-α moiety binds to IFN receptors expressed on the Daudi cells The Timmerman laboratory has produced a transfectant of the murine lymphoma 38C13 that expresses human CD20. Both Rituxan and anti-CD20/IgG3-mu-IFN-α bound the transfectant. Anti-DNS/IgG3-mu-IFN-α showed no binding (FIG. 13).

c. Anti-Viral Activity of the Fusion Proteins

To assess the anti-viral activity of the hu-IFN-α fusion proteins, HeLa cells were seeded at $2 \times 10^5$ cells/ml and treated with two-fold serial dilutions of fusion protein or Roferon (recombinant human interferon 2a) for 24 hrs. Cells were then infected with VSV (vesicular stomatitis virus) at a concentration of 4000 pfu/100 μl. After 72 hrs, cells were stained with 0.1% crystal violet. Protection against viral infection was determined either by quantitating the cells surviving the infection by staining with 0.1% crystal violet and determing the amount of dye in each well using a a spot densitometer of by counting the number of plaques. In both assays the fusion protein had significant IFN-α activity but was about 100-fold reduced in activity compared to Roferon.

Growth Inhibition and Killing of Daudi Lymphoma Cells with the Fusion Proteins.

Figure 14:
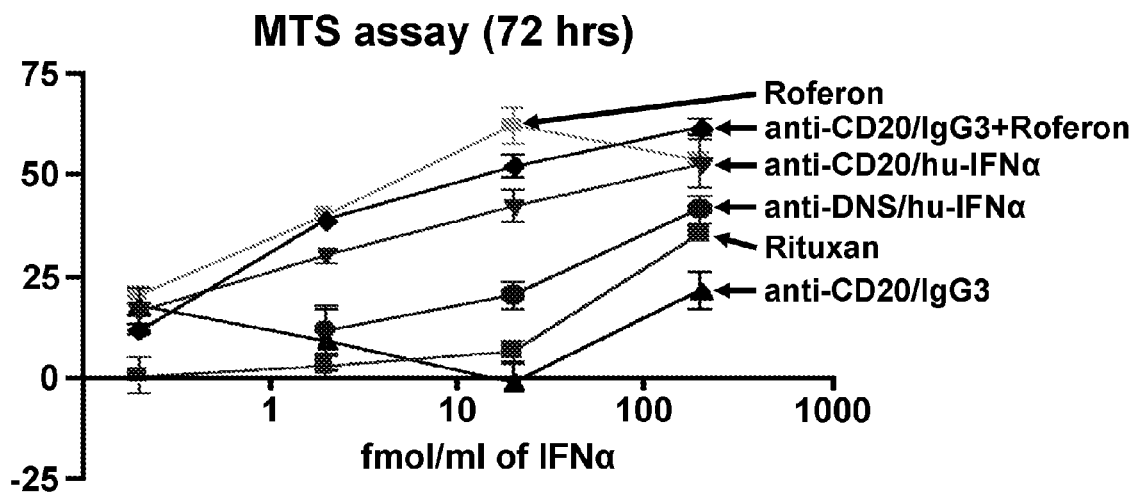
FIG. 14. Daudi cells were incubated with various concentrations of IFN-α, antibody or fusion protein for 72 hrs. Growth inhibition was assessed using the CellTiter 96 AQueous cell proliferation assay.

Two methods were used to assess the growth inhibition/killing of lymphoma cells expressing CD20 by the fusion proteins. It should be noted that for these experiments a human cell line, Daudi, that naturally expresses CD20 was used. In the first approach Daudi cells were incubated with various concentrations of IFN-α, antibody or fusion protein for 72 hrs and growth inhibition assessed using the CellTiter 96 AQueous cell proliferation assay (FIG. 14). Although showing less IFN-α activity in the anti-viral assay, anti-CD20/IgG3-hu-IFN-α and Roferon showed a similar ability to inhibit lymphoma growth suggesting that targeting the IFN-α enhances its cytotoxic effect. Anti-CD20/IgG3+ Roferon did not show enhanced activity compared to Roferon alone. Anti-DNS/IgG3-hIFN-α, Rituxan and anti-CD20/IgG3 only showed some growth inhibition at the highest concentration used. It should be noted that fusion protein was more active than Rituxan in preventing cell growth in this assay.

Figure 15:
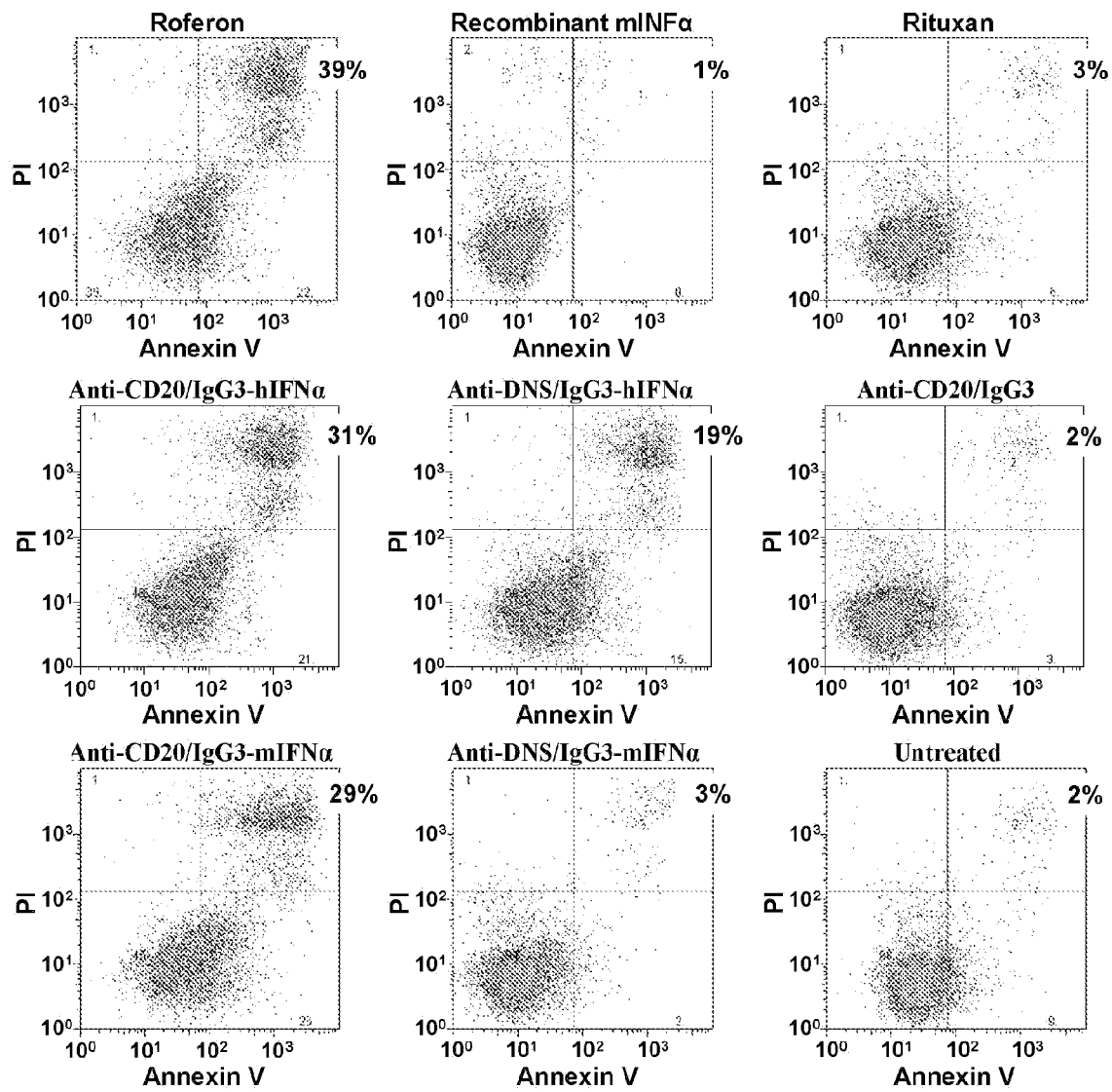
FIG. 15. Daudi cells were treated with 10 pM of the indicated proteins for 72 hors. Cell viability and apoptosis was determined following staining with Annexin V and PI and analysis by FLOW cytometry.

In the second approach, Daudi cells were incubated with various concentrations of IFN-α, antibody or fusion protein for 72 hrs and then stained with Annexin V and propidium iodide (PI) analyzed by FLOW cytometry. Shown in FIG. 15 are the results obtained when 10 pM of the various proteins was used. Cells in the early phases of apoptosis are Annexin $V^+PI^-$; late apoptotic and dead cells are Annexin $V^+PI^+$.

These experiments demonstrate several things. Rituxan and anti-CD20/IgG3 both induce little to no apoptosis, even at the highest concentrations tested. As would be expected, murine IFN-α is less effective against the human cell line than is human recombinant IFN-α (Roferon) and anti-DNS/IgG3- mIFN α which would not target the tumor cells is approximately as effective as recombinant murine IFN-α. However, targeting murine IFN-α to tumor cells using anti-CD20/IgG3-mIFNα results in effective induction of cell death. Anti-CD20/IgG3-hIFNα is more effective than anti-DNS/IgG3-hIFN α, again demonstrating the contribution of cell targeting to cell killing. In this in vitro assay, Roferon and anti-CD20/IgG3-hIFNα exhibit similar activity causing cell death at concentrations as low as 1 pM (data not shown). However, it should be pointed out that in vivo CD20/IgG3-hIFNα will target and accumulate at the site of the tumor while Roferon will exhibit its activity throughout the body.

Figure 16:
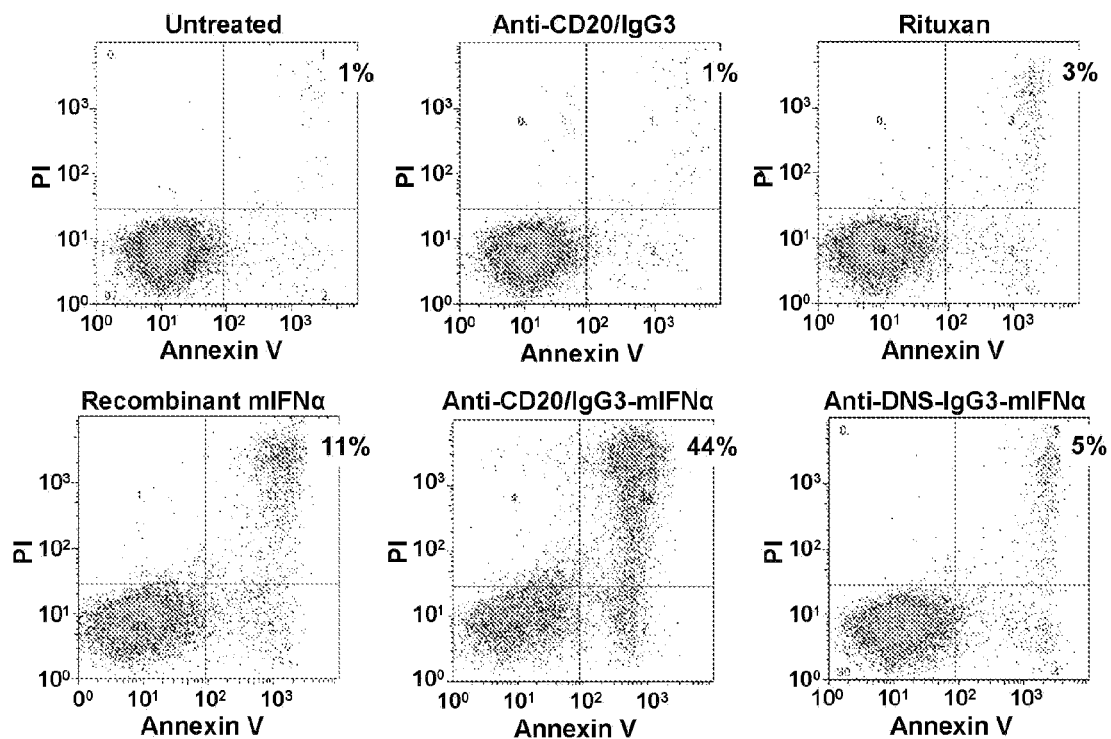
FIG. 16. 38C13/CD20 cells were treated with 10 pM of the indicated proteins for 48 hours. Cell viability and apoptosis was determined following staining with Annexin V and PI and analysis by FLOW cytometry.

Growth Inhibition and Killing of 38C13-CD20 Lymphoma Cells with the Fusion Proteins As briefly mentioned above, the laboratory of Dr. John Timmerman has developed a murine lymphoma, 38C13-CD20, that expresses human CD20 and will grow in syngenic C3H/HeJ mice. The availability of this cell line makes it possible to examine the in vivo efficacy of our fusion proteins. 38C13-CD20 cells were incubated for 48 hours with various antibodies and fusion proteins. Killing and apoptosis were then determined by staining cells with Annexin V and PI and examining them using FLOW cytometry. When proteins were used at a concentration of 100 pM (data not shown) both recombinant mIFN-α and anti-CD20-IgG3-mIFN-α were very effective in causing apoptosis, with anti-CD20-IgG3-mIFN-α somewhat more effective that recombinant mIFN-α. Some apoptosis was induced by treating 38C13-CD20 cells with anti-DNS-IgG3-mIFN-α or Rituxan. Treatment with anti-CD20/IgG3 at this concentration had no effect on cell viability. When the treatment concentration was lowered to 10 pM (FIG. 16), recombinant mIFN-α and anti-CD20/IgG3-mIFN-α continued to be effective in causing apoptosis, with anti-CD20/IgG3-mIFN-α more effective that recombinant mIFN-α. Only a small amount of apoptosis was seen following treatment with anti-DNS-IgG3-mIFN-α indicating that targeting of IFN-α using anti-CD20-IgG3-mIFN-α resulted in a more effective therapeutic agent. At this concentation Rituxan caused little apoptosis, indicating the superiority of the anti-CD20-IgG3/mIFN-α fusion protein over the unfused anti-CD20 antibody. Again, treatment with anti-CD20/IgG3 had no effect on cell viability. At a treatment dose of 1 pM, only anti-CD20-IgG3-mIFN-α induced apoptosis in 38C13-CD20 (data not shown). At a dose of 0.1 pM, none of the treatments induced apoptosis (data not shown).

Figure 17:
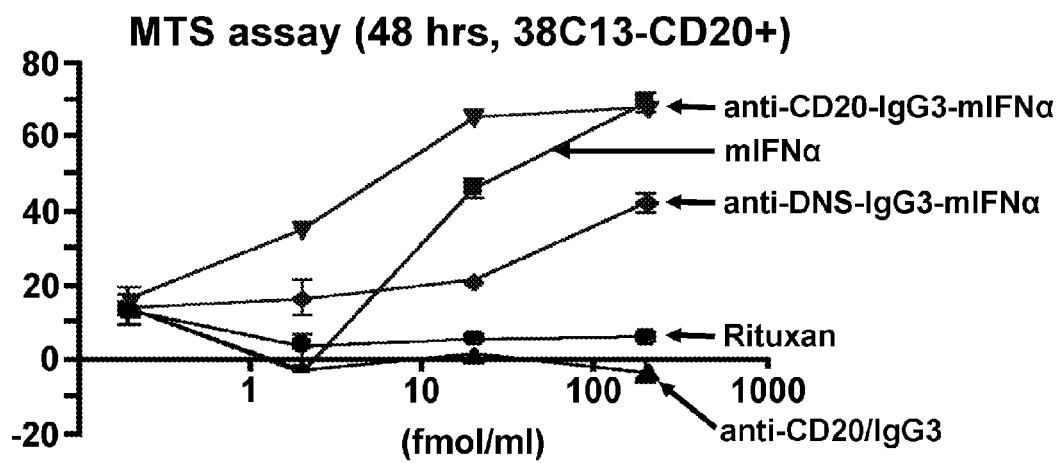
FIG. 17. Inhibition of cell proliferation following treatment with different proteins at varying concentrations. 38C13-CD20 cells were treated with the indicated proteins at varying concentrations for 48 hours. After treatment the extent of proliferation was monitored using the MTS assay.

As an alternative approach, 38C13-CD20 cells were treated with the various proteins at different concentrations and inhibition of growth monitored using the MTS assay (FIG. 17). Anti-CD20/IgG3-mIFN-α was most effective in inhibiting cell growth, followed by recombinant mIFN-α. Some growth inhibition was observed with anti-DNS/IgG3-mIFN-α. Anti-CD20/IgG3 and Rituxan had little effect on cell growth. Thus, the results obtained in this assay mirrored what was observed when apoptosis was monitored.

Production and Characterization of Additional IgG-IFNα Fusion Proteins a. Anti-CD20-IgG1-mIFNα and Anti-CD20-IgG1-hIFNα

The initial proteins were made with IFN-α fused to a human IgG3 backbone. Rituxan is an IgG1. To determine if the immunoglobulin backbone influenced the properties of the fusion proteins, fusion proteins with m-IFN-α and hu-IFN-α fused to IgG1 have now been produced. They were of the expected molecular weight.

Figure 18:
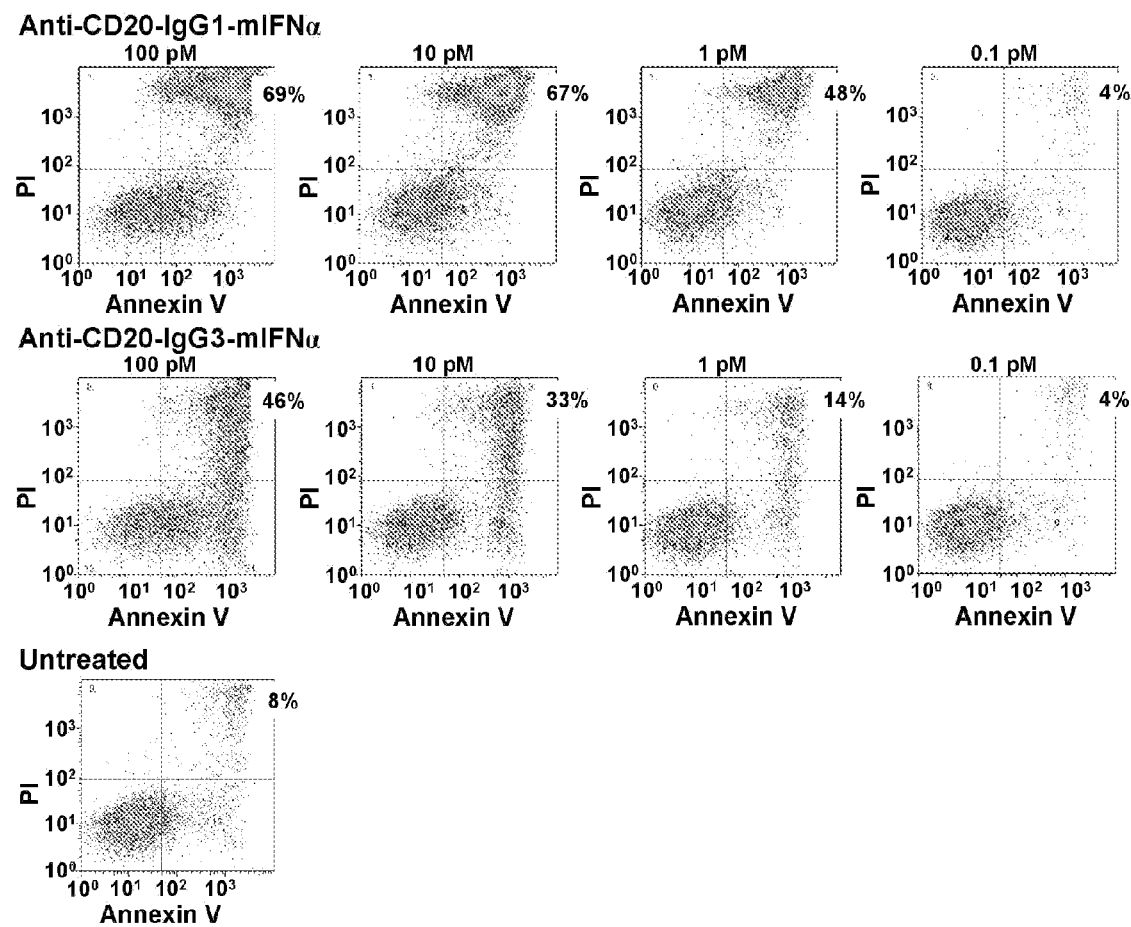
FIG. 18. 38C13/CD20 cells were treated with the different concentrations of the indicated proteins for 48 hours. Cell viability and apoptosis was determined following staining with Annexin V and PI and analysis by FLOW cytometry.

Anti-CD20/IgG1-mIFNα was evaluated for its ability to induce apoptosis of 38C13-CD20 (FIG. 18). The studies showed it to be effective, possibly even more effective than the IgG3 fusion protein.

Figure 19:
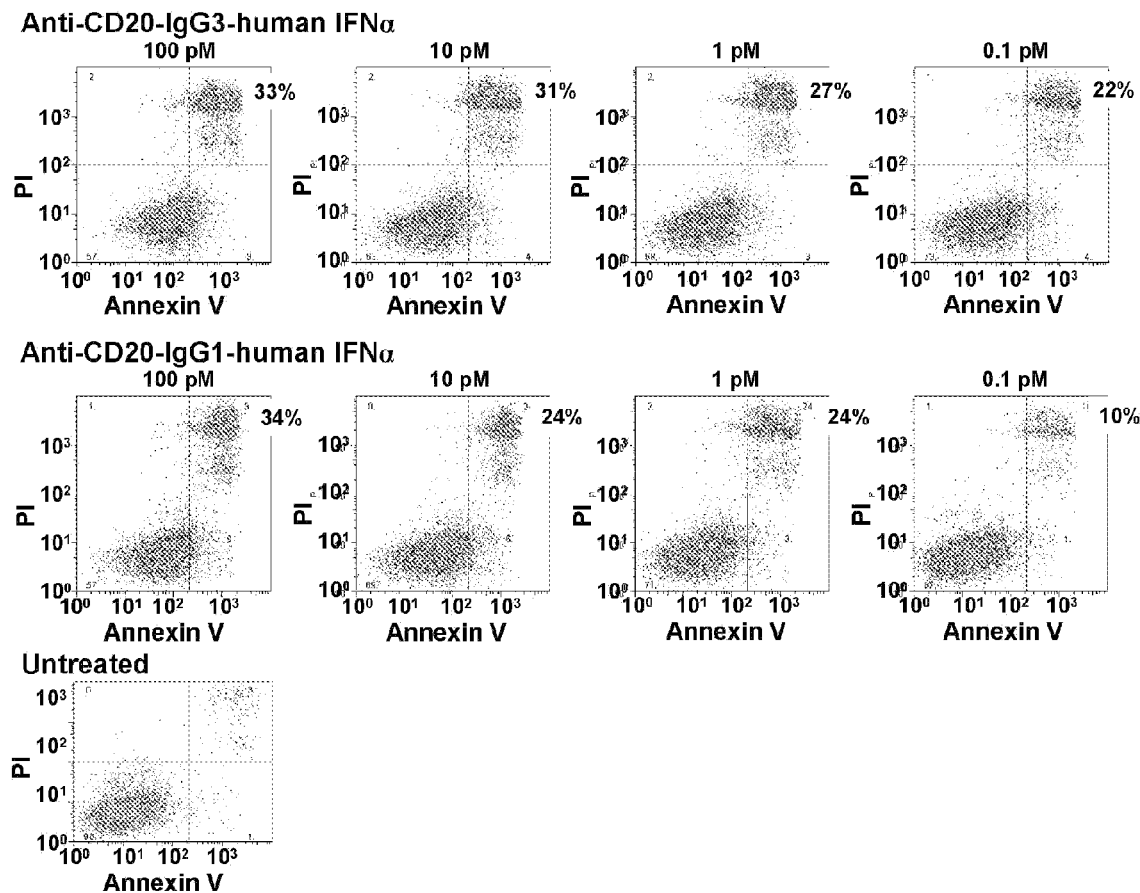
FIG. 19. Daudi cells were incubated for 72 hours with different concentrations of the fusion protein. Cell viability and apoptosis was determined following staining with Annexin V and PI and analysis by FLOW cytometry.

Anti-CD20/IgG1-hIFNα was evaluated for its ability to induce apoptosis of Daudi cells. The studies showed it exhibit activity similar to anti-CD20/IgG3-hIFNα (FIG. 19

Figure 20:
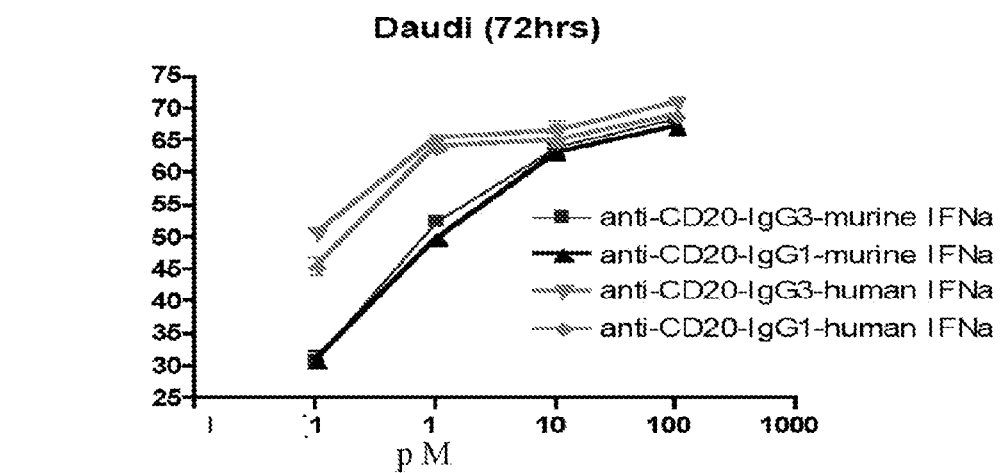
FIG. 20. Daudi cells were treated for 72 hours with various concentrations of fusion proteins. MTS solution was added to quantitate cell viability.

The fusion proteins were evaluated for their ability to inhibit the growth of Daudi cells as shown in FIG. 20. IgG1 fusions with both murine and human IFNα resembled the IgG3 fusions in their ability to inhibit the growth of Daudi cells.

b. Fusion Proteins with IFN-α Joined to the IgG Backbone with an Alpha Helical Linker.

Fusion proteins were produced in which the GlySer linker was replaced with linker with the sequence A(EAAAK)$_2$A (SEQ ID NO:33). This sequence is proposed to fold as an alpha helix.

Protein was produced by transient expression in 293T cells and evaluated by SDS-PAGE. The protein assembled and was of the expected molecular weight. No cleavage of the linker was observed.

The fusion protein, anti-CD20-IgG3-hIFNα (α-helical linker) when used at the same concentration as the fusion protein with the Gly$_4$Ser (SEQ ID NO:32) linker, was found to effectively induce apoptosis of Daudi cells (FIG. 21).

In Vivo Treatment of Tumors

The 38C13 lymphoma that had been transduced by the Timmerman laboratory to express human CD20 was used for these studies. 38C13 is an aggressive lymphoma that grows in syngenic C3H/HeJ mice. The transductant, 38C13-CD20, exhibits the same growth characteristic. Thus it is possible to investigate fusion protein mediated protection in immune competent animals.

a. Treatment of Early Tumors

Figure 23:
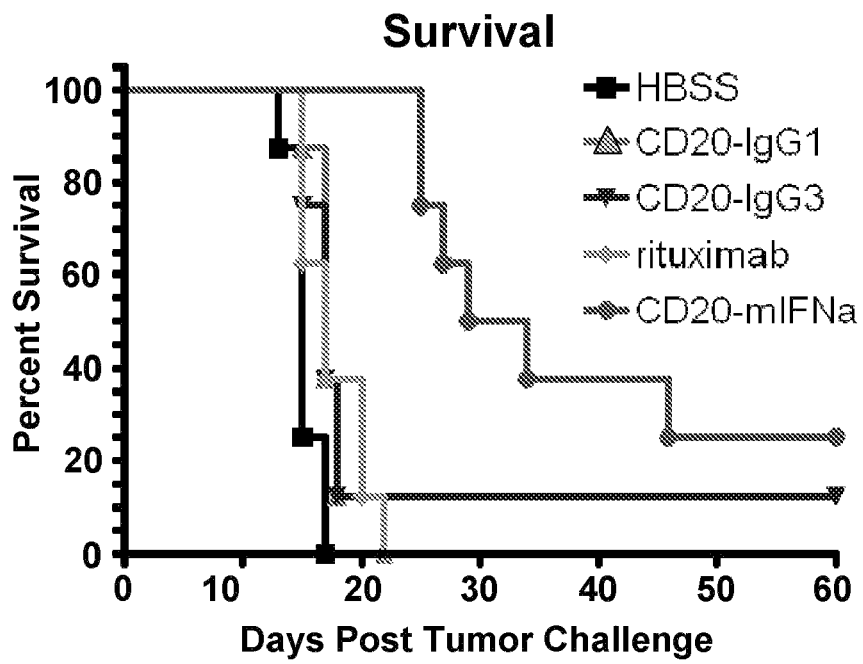
FIG. 23 shows survival of mice inoculated with 5000 38C13-CD20 cells and treated on days 5, 6 and 7 with 10 µg of anti-CD20-IgG1, anti-CD20-IgG3, Rituximab or anti-CD20-IgG3-mIFNα.

Mice (groups of 4) were injected subcutaneously with 5000 38C13-CD20 cells on day zero. On days 1, 2 and 3 they were treated intravenously with hepes buffered saline solution (HBSS) or 0.4 µg, 2 µg, or 10 µg of anti-CD20-m-IFN-α and tumor growth monitored. By day 20 all of the animals treated with HBSS had large tumors and had to be sacrificed. In contrast, no tumor growth was seen in animals treated with 10 µg of the fusion protein; after day 20 tumors began to grow in 3 of the four animals treated with 0.4 µg of the fusion protein and 1 of the mice treated with 2 µg. The results showed that the anti-CD20/IFN-α fusion proteins are very effective in inhibiting in vivo tumor growth and in increasing survival (see, e.g., FIG. 22).

b. The Anti-CD20-mIFNα Fusion Protein is More Effective than Either Rituximab or Anti-CD20/IgG3 in Treating Moderate Sized Tumors C3H/HeJ mice were inoculated with 5000 38C13-CD20 cells on day 0. On days 5, 6 and 7 they were treated with HBSS or 10 µg of anti-CD20-IgG1 (produced in 293T cells), anti-CD20-IgG3, Rituximab or anti-CD20-IgG3-mIFNα. They were monitored for tumor growth and survival (see, e.g., FIG. 23). Anti-CD20/IgG3-mIFNα was much more effective than Rituximab, anti-CD20/IgG3 or anti-CD20/IgG1 in preventing the growth of moderate sized tumors.

The Tumor Targeting Ability of the Fusion Protein Significantly Enhances its Efficacy in Vivo.

Figure 24:
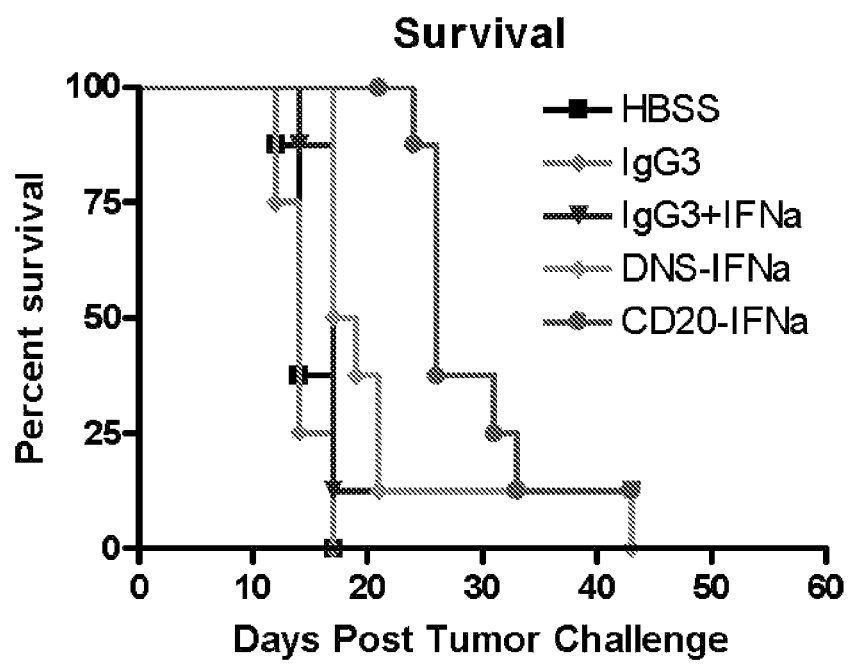
FIG. 24. Survival of mice inoculated with 5000 38C13-CD20 cells and treated on days 5, 6 and 7 with 10 µg of anti-CD20-IgG3, anti-CD20-IgG3 +IFNα, anti-DNS-IgG3, or anti-CD20-IgG3-mIFFNα.

C3H/H3J mice were inoculated with 5000 38C13-CD20 cells on day 0 and treated on days 5, 6 and 7 with 10 µg of anti-CD20-IgG3, 10 µg of anti-CD20-IgG3+mIFN-α (dose chosen to be same moles as in fusion protein), anti-DNS-IgG3-IFNα, or anti-CD20-IgG3-mIFNα and followed for tumor growth and survival (see, e.g., FIG. 24). Anti-CD20-IgG3-IFNα significantly delayed tumor growth and promoted survival indicating that targeting the IFNα to the tumor using the antibody combining site makes it a more effective therapeutic than either a fusion protein that does not target the fused IFNα (anti-DNS-IgG3-IFNα) or the injection of anti-CD20 along with IFNα that is not covalently associated (anti-CD20-IgG3+mIFN-α).

Fusion Protein Treatment is Effective Against Established Tumors

Figure 25:
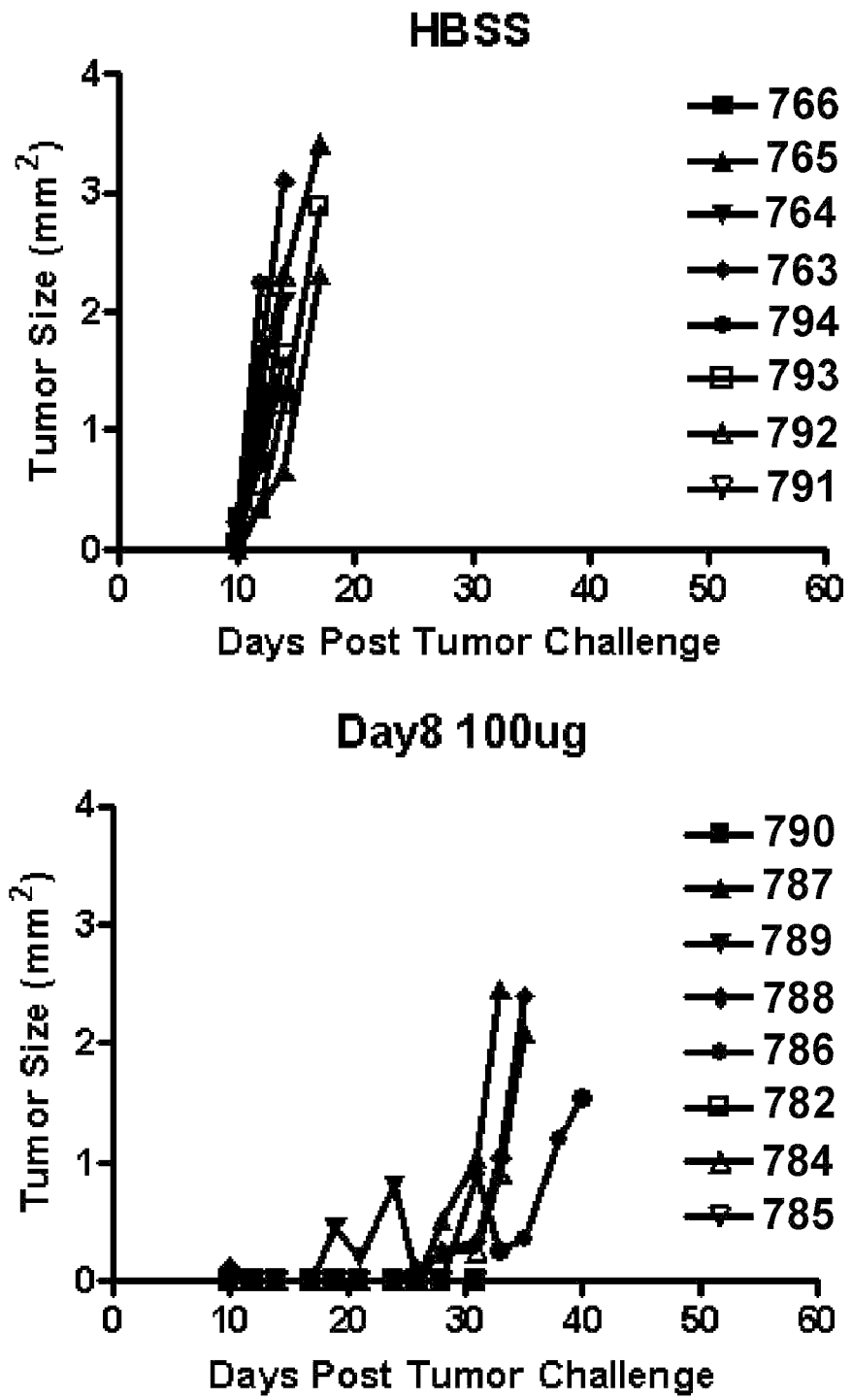
FIG. 25. Groups of eight mice were injected with 5000 38C13-CD20 cells on days 0. One days 8, 9 and 10 they were treated with HBSS or 100 µg of anti-CD20-IgG3-mIFNα. Tumor growth was monitored over time.
Figure 26:
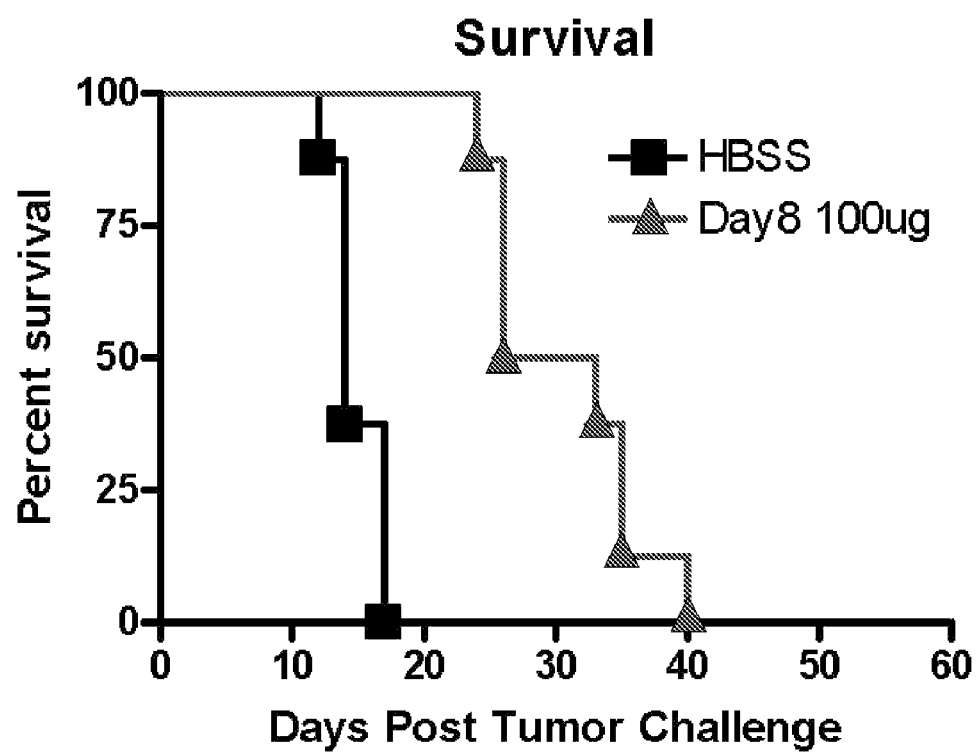
FIG. 26. Groups of eight mice were injected with 5000 38C13-CD20 cells on days 0. One days 8, 9 and 10 they were treated with HBSS or 100 µg of anti-CD20-IgG3-mIFNα. Survival was monitored over time.

Groups of eight C3H/HeJ mice were inoculated with 5000 38C13-CD20 cells and treated on days 8, 9 and 10 with 100 μg of anti-CD20-mIFNα or HBSS. Mice were monitored for tumor growth (see FIG. 25) and survival (see, FIG. 26). Mice inoculated with anti-CD20-mIFNα shows improved survival (FIG. 26).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting growth and/or proliferation of a cancer cell, said method comprising contacting said cancer cell with a chimeric construct comprising a type I interferon attached to a full-length antibody that binds to a tumor-associated antigen, wherein said antibody is attached to said interferon by a peptide linker that is resistant to proteolysis, wherein the amino acid sequence of said peptide linker is SGGGGS (SEQ ID NO:62) or AEAAAKEAAAKAGS (SEQ ID NO:63).

2. The method of claim 1, wherein said cancer cell is selected from the group consisting of a cell in a solid tumor, a metastatic cell, a breast cancer cell, and a B cell lymphoma.

3. The method of claim 1, wherein said cancer cell is cell produced by a cancer selected from the group consisting of a B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

4. The method of claim 1, wherein said contacting comprises administration via a route selected from the group consisting of systemic administration, administration directly into a tumor site, and intravenous administration.

5. The method of claim 1, wherein said cancer cell is a cancer cell in a human.

6. The method of claim 1, wherein said cancer cell is a cancer cell in a non-human mammal.

7. The method of claim 1, wherein said antibody is attached to said interferon by a peptide linker wherein the amino acid sequence of said linker is SGGGGS (SEQ ID NO:62).

8. The method of claim 1, wherein said antibody specifically binds a tumor associated antigen selected from the group consisting of CD20, HER3, HER2/neu, mucin 1 (MUC-1), G250, mesothelin, gp100, tyrosinase, and melanoma-associated antigen (MAGE).

9. The method of claim 1, wherein said antibody is an antibody that binds CD20.

10. The method of claim 1, wherein said antibody is an antibody that comprises the variable regions for anti-CD20 (Rituximab).

11. The method of claim 1, wherein said antibody is an antibody selected form the group consisting of rituximab, IF5, B1, 1H4, CD19, B4, B43, FVS191, hLL2, LL2, RFB4, M195, HuM195, AT13/5, trastuzumab, 4D5, HuCC49, HUCC39ΔCH2 B72.3, 12C10, IG5, H23, BM-2, BM-7, 12H12, MAM-6, HMFG-1.

12. The method of claim 7, wherein said antibody is an antibody that binds to CD20.

13. The method of claim 7, wherein said antibody is an antibody that binds to HER2.

14. The method according to any one of claim 12 or 13, wherein said interferon is IFN-α.

15. The method according to any one of claim 12 or 13, wherein said interferon is IFN-β.

16. The method of claim 1, wherein said antibody is attached to said interferon by a peptide linker wherein the amino acid sequence of said linker is AEAAAKEAAAKAGS (SEQ ID NO:63).

* * * * *